US012383536B2

(12) United States Patent
Smith et al.

(10) Patent No.: US 12,383,536 B2
(45) Date of Patent: Aug. 12, 2025

(54) CRF RECEPTOR ANTAGONISTS AND METHODS OF USE

(71) Applicant: Neurocrine Biosciences, Inc., San Diego, CA (US)

(72) Inventors: Evan Smith, San Diego, CA (US); Sha Luo, San Diego, CA (US); Gordon Raphael Loewen, San Diego, CA (US); Neil J. Ashweek, San Diego, CA (US); John P. Williams, San Diego, CA (US)

(73) Assignee: Neurocrine Biosciences, Inc., San Diego, CA (US)

( * ) Notice: Subject to any disclaimer, the term of this patent is extended or adjusted under 35 U.S.C. 154(b) by 477 days.

(21) Appl. No.: 17/764,050

(22) PCT Filed: Sep. 25, 2020

(86) PCT No.: PCT/US2020/052851
§ 371 (c)(1),
(2) Date: Mar. 25, 2022

(87) PCT Pub. No.: WO2021/062246
PCT Pub. Date: Apr. 1, 2021

(65) Prior Publication Data
US 2022/0409592 A1 Dec. 29, 2022

Related U.S. Application Data

(60) Provisional application No. 62/906,967, filed on Sep. 27, 2019.

(51) Int. Cl.
*A61K 31/427* (2006.01)

(52) U.S. Cl.
CPC ................................ *A61K 31/427* (2013.01)

(58) Field of Classification Search
CPC ................................ A61K 31/427; A61P 5/00
See application file for complete search history.

(56) References Cited

U.S. PATENT DOCUMENTS

| | | | |
|---|---|---|---|
| 5,464,847 A | 11/1995 | Courtemanche et al. |
| 6,344,470 B1 | 2/2002 | Fontaine et al. |
| 6,365,180 B1 | 4/2002 | Meyer et al. |
| 6,531,475 B1 | 3/2003 | Haddach et al. |
| 6,586,456 B1 | 7/2003 | Fontaine et al. |
| 6,610,678 B2 | 8/2003 | Huang et al. |
| 6,664,261 B2 | 12/2003 | Chen et al. |
| 6,806,282 B2 | 10/2004 | Geslin et al. |
| 7,276,526 B2 | 10/2007 | Termin et al. |
| 7,297,708 B2 | 11/2007 | Termin et al. |
| 7,951,803 B2 | 5/2011 | Cole et al. |
| 8,030,304 B2 | 10/2011 | Chen et al. |
| 8,153,127 B2 | 4/2012 | Paez-Pereda et al. |
| 8,314,249 B2 | 11/2012 | Fazekas et al. |
| 8,420,679 B2 | 4/2013 | Fontaine et al. |
| 9,351,517 B2 | 5/2016 | Bromley |
| 10,849,908 B2 | 12/2020 | Howerton et al. |
| 10,905,690 B2 | 2/2021 | Grigoriadis |
| 11,007,201 B2 | 5/2021 | Howerton et al. |
| 11,304,950 B2 | 4/2022 | Howerton et al. |
| 11,311,544 B2 | 4/2022 | Grigoriadis |
| 11,730,739 B2 | 8/2023 | Grigoriadis |
| 11,858,932 B2 | 1/2024 | Barnes et al. |
| 12,128,033 B2 | 10/2024 | Becker et al. |
| 2005/0209250 A1 | 9/2005 | Romano |
| 2006/0078623 A1 | 4/2006 | Dhoot et al. |
| 2007/0281919 A1 | 12/2007 | Fontaine et al. |
| 2009/0203755 A1 | 8/2009 | Richard |
| 2010/0216751 A1 | 8/2010 | Jacob et al. |
| 2010/0222339 A1 | 9/2010 | Chen et al. |
| 2013/0183383 A1 | 7/2013 | Phang et al. |
| 2015/0094310 A1 | 4/2015 | Holsboer |
| 2015/0284362 A1 | 10/2015 | Bersot et al. |
| 2017/0020877 A1 | 1/2017 | Grigoriadis |
| 2019/0231781 A1 | 8/2019 | Grigoriadis |
| 2021/0137926 A1 | 5/2021 | Grigoriadis |
| 2021/0361659 A1 | 11/2021 | Grigoriadis |
| 2022/0023266 A1 | 1/2022 | Farber et al. |
| 2022/0133742 A1 | 5/2022 | Ghosh et al. |
| 2022/0211711 A1 | 7/2022 | Howerton et al. |
| 2023/0065034 A1 | 3/2023 | Ashweek et al. |
| 2023/0233534 A1 | 7/2023 | Palmer et al. |
| 2023/0255942 A1 | 8/2023 | Farber et al. |
| 2023/0286932 A1 | 9/2023 | Palmer et al. |
| 2023/0295161 A1 | 9/2023 | Barnes et al. |
| 2024/0024330 A1 | 1/2024 | Loewen et al. |
| 2024/0058342 A1 | 2/2024 | Grigoriadis |

(Continued)

FOREIGN PATENT DOCUMENTS

| | | |
|---|---|---|
| CN | 1370154 | 9/2002 |
| CN | 101381314 A | 3/2009 |
| CN | 102414185 | 4/2012 |

(Continued)

OTHER PUBLICATIONS

[No Author], "Guidance for Industry: Q3A Impurities in New Drug Substances," U.S. Department of Health and Human Services, Jun. 2008, 17 pages.
Auchus et al., "Crinecerfont Lowers Elevated Biomarkers of Disease Control in Adults with Congenital Adrenal Hyperplasia Due to 21-Hydroxylase Deficiency," submitted to Lancet Apr. 30, 2021, 33 pages.
Auchus et al., "Phase 3 Trial of Crinecerfont in Adult Congenital Adrenal Hyperplasia," The New England Journal of Medicine, Jun. 1, 2024, 11 pages.
Bastin et al., "Salt Selection and Optimisation Procedures for Pharmaceutical New Chemical Entities," Organic Process Research & Development, 2000, 4:427-435.

(Continued)

*Primary Examiner* — Kamal A Saeed
(74) *Attorney, Agent, or Firm* — Fish & Richardson P.C.

(57) ABSTRACT

Compounds are provided herein, as well as related preparations, compositions and methods for treating diseases and/or disorders that would benefit from the same such as congenital adrenal hyperplasia (CAH).

4 Claims, No Drawings

(56) References Cited

U.S. PATENT DOCUMENTS

2024/0238257 A1  7/2024  Becker et al.

FOREIGN PATENT DOCUMENTS

| | | |
|---|---|---|
| CN | 106102740 | 11/2016 |
| CN | 107438606 | 12/2017 |
| JP | 2002-030048 A | 1/2002 |
| JP | 4949582 | 3/2012 |
| JP | 2012-525368 A | 10/2012 |
| JP | 2013-231063 | 11/2013 |
| JP | 2015-516979 A | 6/2015 |
| JP | 2018-516231 A | 6/2018 |
| RU | 2523793 C2 | 7/2014 |
| RU | 2667977 C2 | 9/2018 |
| WO | WO 1987/005297 | 9/1987 |
| WO | WO 1998/008846 | 3/1998 |
| WO | WO 1998/011075 | 3/1998 |
| WO | WO 1999/010350 | 3/1999 |
| WO | WO 2000/059888 | 10/2000 |
| WO | WO 2001/005776 | 1/2001 |
| WO | WO 2003/006015 | 1/2003 |
| WO | WO 2003/022820 A1 | 3/2003 |
| WO | WO 2006/044821 | 4/2006 |
| WO | WO 2006/044958 | 4/2006 |
| WO | WO 2006/102194 | 9/2006 |
| WO | WO 2006/107784 | 10/2006 |
| WO | WO 2006/116412 | 11/2006 |
| WO | WO 2006/126718 | 11/2006 |
| WO | WO 2007/069565 | 6/2007 |
| WO | WO 2007/069671 | 6/2007 |
| WO | WO 2007/090631 | 8/2007 |
| WO | WO 2007/104053 A2 | 9/2007 |
| WO | WO 2007/105113 | 9/2007 |
| WO | WO 2007/137227 | 11/2007 |
| WO | WO 2008/036541 | 3/2008 |
| WO | WO 2008/036579 | 3/2008 |
| WO | WO 2008/051533 | 5/2008 |
| WO | WO 2008/082003 | 7/2008 |
| WO | WO 2008/083070 | 7/2008 |
| WO | WO 2008/136377 | 11/2008 |
| WO | WO 2009/008552 | 1/2009 |
| WO | WO 2009/144632 | 12/2009 |
| WO | WO 2010/014280 | 2/2010 |
| WO | WO 2010/014687 | 2/2010 |
| WO | WO 2010/015628 | 2/2010 |
| WO | WO 2010/015655 | 2/2010 |
| WO | WO 2010/062718 | 6/2010 |
| WO | WO 2010/096426 | 8/2010 |
| WO | WO 2010/125414 | 11/2010 |
| WO | WO 2011/043381 | 4/2011 |
| WO | WO 2011/043387 | 4/2011 |
| WO | WO 2011/092290 | 8/2011 |
| WO | WO 2011/092293 | 8/2011 |
| WO | WO 2011/095450 | 8/2011 |
| WO | WO 2011/128783 A2 | 10/2011 |
| WO | WO 2013/155464 | 10/2013 |
| WO | WO 2013/160315 | 10/2013 |
| WO | WO 2013/160317 | 10/2013 |
| WO | WO 2014/151109 A1 | 9/2014 |
| WO | WO 2015/112642 | 7/2015 |
| WO | WO 2015/159170 A2 | 10/2015 |
| WO | WO 2016/065177 | 4/2016 |
| WO | WO 2016/127133 | 8/2016 |
| WO | WO 2016/156575 A2 | 10/2016 |
| WO | WO 2016/156576 | 10/2016 |
| WO | WO 2017/031325 A1 | 2/2017 |
| WO | WO 2018/102552 | 6/2018 |
| WO | WO 2018/219804 | 12/2018 |
| WO | WO 2019/036472 | 2/2019 |
| WO | WO 2019/036503 | 2/2019 |
| WO | WO 2019/210266 | 10/2019 |
| WO | WO 2020/115555 | 6/2020 |
| WO | WO 2021/016208 | 1/2021 |
| WO | WO 2021/062246 | 4/2021 |
| WO | WO 2021/111179 A1 | 6/2021 |
| WO | WO 2021/113263 | 6/2021 |
| WO | WO 2021/250468 | 12/2021 |
| WO | WO 2021/252669 | 12/2021 |
| WO | WO 2022/036123 A1 | 2/2022 |
| WO | WO 2022/046905 | 3/2022 |
| WO | WO 2022/153062 A1 | 7/2022 |
| WO | WO 2022/184549 A1 | 9/2022 |

OTHER PUBLICATIONS

Boston University, "InterQuartile Range (IQR)," available on or before Oct. 31, 2013, via Internet Archive: Wayback Machine URL<https://web.archive.org/web/20131031075431/https://sphweb.bumc.bu.edu/otlt/mph-modules/bs/bs704_summarizingdata/bs704_summarizingdata7.html>, retrieved on Feb. 17, 2024, retrieved from URL<https://sphweb.bumc.bu.edu/otlt/mph-modules/bs/bs704_summarizingdata/bs704_summarizingdata7.html>, 3 pages.

Byrn et al., "Pharmaceutical Solids: A Strategic Approach to Regulatory Considerations," Pharmaceutical Research, 1995, 12(7):945-954.

Ceramella et al., "A Look at the Importance of Chirality in Drug Activity: Some Significative Examples," Applied Sciences, Oct. 27, 2022, 12:10909, 22 pages.

Croce et al., "A Simple Procedure for N-Propenylation and N-Propynylation of Secondary Amines," Gazetta Chimica Italiana, 1996, 126(2):107-109.

De Villiers, "Pharmaceutical solvents and solubilizing agents," Pharmaceutical Excipients, Part 4, 2009, 15 pages.

De Villiers, "Vehicles for Liquid Preparations," A Practical Guide to Contemporary Pharmacy Practice, 3rd Editions, Jan. 2009, 22:267-276 pages.

Gupta al., "Formulation strategies to improve the bioavailability of poorly absorbed drugs with special emphasis on self-emulsifying systems," ISRN Pharmaceutics, 2013, pp. 1-16.

Habibzadeh, "Statistical Data Editing in Scientific Articles," Journal of Korean Medical Science, Jul. 2017, 32(7):1072-1076.

Hirayama, "[Handbook for manufacturing crystal of organic compound—principle and know-how]," Maruzen, Jul. 2008, 57-84 (with English translation).

Kamrath et al., "CRH receptor antagonist crinecerfont—a promising new treatment option for patients with congenital adrenal hyperplasia due to 21-hydroxylase deficiency," J Pediatric Endocrinology and Metabolism, Nov. 25, 2024, 6 pages.

Kojima, "[Effective solid form selection for the pharmaceutical development," Journal of Pharmaceutical Science and Technology, Sep. 1, 2008, 68(5):344-349 (with English translation).

Kumbhar et al., "D-α-tocopheryl polyethylene glycol succinate: A review of multifarious applications in nanomedicines," OpenNano, Mar. 2022, 6:100036, 13 pages.

Lee et al., "Standard deviation and standard error of the mean," Korean Journal of Anesthesiology, Jun. 2015, 68(3):220-223.

Li et al., "Use of Spray-Dried Dispersions in Early Pharmaceutical Development: Theoretical and Practical Challenges," AAPS J, Mar. 2017, 19:321-333.

Mercado-Asis et al., "Acute Effects of Bromocriptine, Cyproheptadine, and Valproic Acid on Plasma Adrenocorticotropin Secretion in Nelson's Syndrome," Journal of Clinical Endocrinology & Metabolism, 1997, 82(2):514-517.

*Neurocrine Biosciences, Inc.*, Petitioner, v. *Spruce Biosciences, Inc.*, Patent Owner, Case No. PGR2021-00088, U.S. Pat. No. 10,849,908, Decision Denying Institution of Post-Grant Review 35 U.S.C. § 324, filed Dec. 10, 2021, 36 pages.

*Neurocrine Biosciences, Inc.*, Petitioner, v. *Spruce Biosciences, Inc.*, Patent Owner, Case No. PGR2021-00088, U.S. Pat. No. 10,849,908, Decision Granting Institution of Post-Grant Review 35 U.S.C. § 324, filed Dec. 1, 2023, 57 pages.

*Neurocrine Biosciences, Inc.*, Petitioner, v. *Spruce Biosciences, Inc.*, Patent Owner, Case No. PGR2021-00088, U.S. Pat. No. 10,849,908, Decision Vacating the Decision Denying Institution and Remanding to the Patent Trial and Appeal Board Panel for Further Proceedings, filed Aug. 4, 2023, 16 pages.

(56) References Cited

OTHER PUBLICATIONS

*Neurocrine Biosciences, Inc.*, Petitioner, v. *Spruce Biosciences, Inc.*, Patent Owner, Case No. PGR2021-00088, U.S. Pat. No. 10,849,908, Declaration of Adrian Dobs, M.D., M.H.S., filed Mar. 12, 2024, 68 pages.
*Neurocrine Biosciences, Inc.*, Petitioner, v. *Spruce Biosciences, Inc.*, Patent Owner, Case No. PGR2021-00088, U.S. Pat. No. 10,849,908, Declaration of Gordon B. Cutler, Jr., M.D. in Support of Petition for Post Grant Review of U.S. Pat. No. 10,849,908, filed Jan. 5, 2024, 228 pages.
*Neurocrine Biosciences, Inc.*, Petitioner, v. *Spruce Biosciences, Inc.*, Patent Owner, Case No. PGR2021-00088, U.S. Pat. No. 10,849,908, Deposition of Dr. Gordon B. Cutler, Jr., Washington, D.C., Thursday, Jul. 25, 2024, 207 pages.
*Neurocrine Biosciences, Inc.*, Petitioner, v. *Spruce Biosciences, Inc.*, Patent Owner, Case No. PGR2021-00088, U.S. Pat. No. 10,849,908, Patent Owner Spruce Biosciences' Motion To Exclude 37 C.F.R. §42.64(c), filed Aug. 14, 2024, 10 pages.
*Neurocrine Biosciences, Inc.*, Petitioner, v. *Spruce Biosciences, Inc.*, Patent Owner, Case No. PGR2021-00088, U.S. Pat. No. 10,849,908, Patent Owner's Objections To Evidence, filed on Jun. 27, 2024, 9 pages.
*Neurocrine Biosciences, Inc.*, Petitioner, v. *Spruce Biosciences, Inc.*, Patent Owner, Case No. PGR2021-00088, U.S. Pat. No. 10,849,908, Patent Owner's Opposition To Petitioner's Motion To Exclude Evidence 37 C.F.R. §42.64, filed Aug. 20, 2024, 15 pages.
*Neurocrine Biosciences, Inc.*, Petitioner, v. *Spruce Biosciences, Inc.*, Patent Owner, Case No. PGR2021-00088, U.S. Pat. No. 10,849,908, Patent Owner's Opposition To Petitioner's Motion To Strike, filed Aug. 28, 2024, 8 pages.
*Neurocrine Biosciences, Inc.*, Petitioner, v. *Spruce Biosciences, Inc.*, Patent Owner, Case No. PGR2021-00088, U.S. Pat. No. 10,849,908, Patent Owner's Preliminary Response, filed Sep. 15, 2021, 57 pages.
*Neurocrine Biosciences, Inc.*, Petitioner, v. *Spruce Biosciences, Inc.*, Patent Owner, Case No. PGR2021-00088, U.S. Pat. No. 10,849,908, Patent Owner's Reply in Support of Its Motion To Exclude, filed Aug. 23, 2024, 8 pages.
*Neurocrine Biosciences, Inc.*, Petitioner, v. *Spruce Biosciences, Inc.*, Patent Owner, Case No. PGR2021-00088, U.S. Pat. No. 10,849,908, Patent Owner's Response, filed Mar. 12, 2024, 91 pages.
*Neurocrine Biosciences, Inc.*, Petitioner, v. *Spruce Biosciences, Inc.*, Patent Owner, Case No. PGR2021-00088, U.S. Pat. No. 10,849,908, Patent Owner's Sur-Reply, filed Aug. 12, 2024, 36 pages.
*Neurocrine Biosciences, Inc.*, Petitioner, v. *Spruce Biosciences, Inc.*, Patent Owner, Case No. PGR2021-00088, U.S. Pat. No. 10,849,908, Petition for Post Grant Review of U.S. Pat. No. 10,849,908, filed May 28, 2021, 90 pages.
*Neurocrine Biosciences, Inc.*, Petitioner, v. *Spruce Biosciences, Inc.*, Patent Owner, Case No. PGR2021-00088, U.S. Pat. No. 10,849,908, Petitioner's Motion To Exclude Evidence, filed Aug. 14, 2024, 16 pages.
*Neurocrine Biosciences, Inc.*, Petitioner, v. *Spruce Biosciences, Inc.*, Patent Owner, Case No. PGR2021-00088, U.S. Pat. No. 10,849,908, Petitioner's Motion To Strike, filed Aug. 22, 2024, 13 pages.
*Neurocrine Biosciences, Inc.*, Petitioner, v. *Spruce Biosciences, Inc.*, Patent Owner, Case No. PGR2021-00088, U.S. Pat. No. 10,849,908, Petitioner's Opposition To Patent Owner's Motion To Exclude Evidence, filed Aug. 20, 2024, 19 pages.
*Neurocrine Biosciences, Inc.*, Petitioner, v. *Spruce Biosciences, Inc.*, Patent Owner, Case No. PGR2021-00088, U.S. Pat. No. 10,849,908, Petitioner's Reply in Support of its Motion to Exclude Evidence, filed Aug. 23, 2024, 9 pages.
*Neurocrine Biosciences, Inc.*, Petitioner, v. *Spruce Biosciences, Inc.*, Patent Owner, Case No. PGR2021-00088, U.S. Pat. No. 10,849,908, Petitioner's Request for Rehearing, filed Jan. 10, 2022, 18 pages.
*Neurocrine Biosciences, Inc.*, Petitioner, v. *Spruce Biosciences, Inc.*, Patent Owner, Case No. PGR2021-00088, U.S. Pat. No. 10,849,908, Petitioner's Reply To Patent Owner's Response, filed on Jun. 20, 2024, 38 pages.
*Neurocrine Biosciences, Inc.*, Petitioner, v. *Spruce Biosciences, Inc.*, Patent Owner, Case No. PGR2021-00088, U.S. Pat. No. 10,849,908, Reply Declaration of Gordon B. Cutler, Jr., M.D., filed Jun. 20, 2024, 64 pages.
*Neurocrine Biosciences, Inc.*, Petitioner, v. *Spruce Biosciences, Inc.*, Patent Owner, Case No. PGR2022-00025, U.S. Pat. No. 11,007,201, Decision Denying Institution of Post-Grant Review 35 U.S.C. § 324(a), filed Sep. 15, 2022, 35 pages.
*Neurocrine Biosciences, Inc.*, Petitioner, v. *Spruce Biosciences, Inc.*, Patent Owner, Case No. PGR2022-00025, U.S. Pat. No. 11,007,201, Decision Granting Institution of Post-Grant Review 35 U.S.C. § 324(a), filed Dec. 1, 2023, 38 pages.
*Neurocrine Biosciences, Inc.*, Petitioner, v. *Spruce Biosciences, Inc.*, Patent Owner, Case No. PGR2022-00025, U.S. Pat. No. 11,007,201, Declaration of Adrian Dobs, M.D., M.H.S., filed Mar. 12, 2024, 63 pages.
*Neurocrine Biosciences, Inc.*, Petitioner, v. *Spruce Biosciences, Inc.*, Patent Owner, Case No. PGR2022-00025, U.S. Pat. No. 11,007,201, Declaration of Gordon B. Cutler, Jr., M.D. in Support of Petition for Post Grant Review of U.S. Pat. No. 11,007,201, filed Jan. 5, 2024, 224 pages.
*Neurocrine Biosciences, Inc.*, Petitioner, v. *Spruce Biosciences, Inc.*, Patent Owner, Case No. PGR2022-00025, U.S. Pat. No. 11,007,201, Patent Owner Spruce Biosciences' Motion To Exclude 37 C.F.R. §42.64(c), filed Aug. 14, 2024, 9 pages.
*Neurocrine Biosciences, Inc.*, Petitioner, v. *Spruce Biosciences, Inc.*, Patent Owner, Case No. PGR2022-00025, U.S. Pat. No. 11,007,201, Patent Owner's Objections To Evidence, filed Jun. 27, 2024, 8 pages.
*Neurocrine Biosciences, Inc.*, Petitioner, v. *Spruce Biosciences, Inc.*, Patent Owner, Case No. PGR2022-00025, U.S. Pat. No. 11,007,201, Patent Owner's Objections To Evidence, filed on Dec. 15, 2023, 7 pages.
*Neurocrine Biosciences, Inc.*, Petitioner, v. *Spruce Biosciences, Inc.*, Patent Owner, Case No. PGR2022-00025, U.S. Pat. No. 11,007,201, Patent Owner's Opposition To Petitioner's Motion To Exclude Evidence 37 C.F.R. §42.64, filed Aug. 20, 2024, 15 pages.
*Neurocrine Biosciences, Inc.*, Petitioner, v. *Spruce Biosciences, Inc.*, Patent Owner, Case No. PGR2022-00025, U.S. Pat. No. 11,007,201, Patent Owner's Opposition To Petitioner's Motion To Strike, filed Aug. 28, 2024, 8 pages.
*Neurocrine Biosciences, Inc.*, Petitioner, v. *Spruce Biosciences, Inc.*, Patent Owner, Case No. PGR2022-00025, U.S. Pat. No. 11,007,201, Patent Owner's Pre-Institution Sur-Reply, filed Jul. 28, 2022, 8 pages.
*Neurocrine Biosciences, Inc.*, Petitioner, v. *Spruce Biosciences, Inc.*, Patent Owner, Case No. PGR2022-00025, U.S. Pat. No. 11,007,201, Patent Owner's Preliminary Response, filed Jun. 17, 2022, 72 pages.
*Neurocrine Biosciences, Inc.*, Petitioner, v. *Spruce Biosciences, Inc.*, Patent Owner, Case No. PGR2022-00025, U.S. Pat. No. 11,007,201, Patent Owner's Reply in Support of Its Motion To Exclude, filed Aug. 23, 2024, 7 pages.
*Neurocrine Biosciences, Inc.*, Petitioner, v. *Spruce Biosciences, Inc.*, Patent Owner, Case No. PGR2022-00025, U.S. Pat. No. 11,007,201, Patent Owner's Response, filed Mar. 12, 2024, 93 pages.
*Neurocrine Biosciences, Inc.*, Petitioner, v. *Spruce Biosciences, Inc.*, Patent Owner, Case No. PGR2022-00025, U.S. Pat. No. 11,007,201, Patent Owner's Sur-Reply, filed Aug. 12, 2024, 33 pages.
*Neurocrine Biosciences, Inc.*, Petitioner, v. *Spruce Biosciences, Inc.*, Patent Owner, Case No. PGR2022-00025, U.S. Pat. No. 11,007,201, Petition for Post Grant Review of U.S. Pat. No. 11,007,201, filed Feb. 18, 2022, 92 pages.
*Neurocrine Biosciences, Inc.*, Petitioner, v. *Spruce Biosciences, Inc.*, Patent Owner, Case No. PGR2022-00025, U.S. Pat. No. 11,007,201, Petitioner's Motion To Exclude Evidence, filed Aug. 14, 2024, 16 pages.
*Neurocrine Biosciences, Inc.*, Petitioner, v. *Spruce Biosciences, Inc.*, Patent Owner, Case No. PGR2022-00025, U.S. Pat. No. 11,007,201, Petitioner's Motion To Strike, filed Aug. 22, 2024, 14 pages.
*Neurocrine Biosciences, Inc.*, Petitioner, v. *Spruce Biosciences, Inc.*, Patent Owner, Case No. PGR2022-00025, U.S. Pat. No. 11,007,201, Petitioner's Objections To Evidence, filed Aug. 19, 2024, 4 pages.

(56) References Cited

OTHER PUBLICATIONS

*Neurocrine Biosciences, Inc.*, Petitioner, v. *Spruce Biosciences, Inc.*, Patent Owner, Case No. PGR2022-00025, U.S. Pat. No. 11,007,201, Petitioner's Objections To Evidence, filed Mar. 19, 2024, 6 pages.
*Neurocrine Biosciences, Inc.*, Petitioner, v. *Spruce Biosciences, Inc.*, Patent Owner, Case No. PGR2022-00025, U.S. Pat. No. 11,007,201, Petitioner's Opposition To Patent Owner's Motion To Exclude Evidence, filed Aug. 20, 2024, 15 pages.
*Neurocrine Biosciences, Inc.*, Petitioner, v. *Spruce Biosciences, Inc.*, Patent Owner, Case No. PGR2022-00025, U.S. Pat. No. 11,007,201, Petitioner's Reply in Support of Its Motion To Exclude Evidence, filed Aug. 23, 2024, 9 pages.
*Neurocrine Biosciences, Inc.*, Petitioner, v. *Spruce Biosciences, Inc.*, Patent Owner, Case No. PGR2022-00025, U.S. Pat. No. 11,007,201, Petitioner's Reply To Patent Owner's Preliminary Response, filed Jul. 14, 2022, 9 pages.
*Neurocrine Biosciences, Inc.*, Petitioner, v. *Spruce Biosciences, Inc.*, Patent Owner, Case No. PGR2022-00025, U.S. Pat. No. 11,007,201, Petitioner's Reply To Patent Owner's Response, filed Jun. 20, 2024, 36 pages.
*Neurocrine Biosciences, Inc.*, Petitioner, v. *Spruce Biosciences, Inc.*, Patent Owner, Case No. PGR2022-00025, U.S. Pat. No. 11,007,201, Petitioner's Request for Rehearing, filed Oct. 13, 2022, 17 pages.
*Neurocrine Biosciences, Inc.*, Petitioner, v. *Spruce Biosciences, Inc.*, Patent Owner, Case No. PGR2022-00025, U.S. Pat. No. 11,007,201, Reply Declaration of Gordon B. Cutler, Jr., M.D., filed Jun. 20, 2024, 60 pages.
*Neurocrine Biosciences, Inc.*, Petitioner, v. *Spruce Biosciences, Inc.*, Patent Owner, Case Nos. PGR2021-00088 and PGR2022-00025, U.S. Pat. Nos. 10,849,908 and 11,007,201, "Transcript of Feb. 29, 2024 Deposition of Gordon B. Cutler, Jr., M.D.," filed on Mar. 12, 2024, 147 pages.
*Neurocrine Biosciences, Inc.*, Petitioner, v. *Spruce Biosciences, Inc.*, Patent Owner, Case Nos. PGR2021-00088 and PGR2022-00025, U.S. Pat. Nos. 10,849,908 and 11,007,201, "Transcript of Jun. 5, 2024 Deposition of Dr. Adrian Dobs," filed on Jun. 20, 2024, 169 pages.
Newfield et al., "ACTH receptor blockade: A novel approach to treat congenital adrenal hyperplasia, or Cushing's disease," Medical Hypotheses, Apr. 2010, 74(4):705-706.
Recto II et al., "Comparison of the Efficacy and Tolerability of Simvastatin and Atorvastatin in the Treatment of Hypercholesterolemia," Clinical Cardiology, 2000, 23(9):682-688.
Saal et al., "Pharmaceutical salts: A summary on doses of salt formers from the Orange Book," European Journal of Pharmaceutical Sciences, Jul. 16, 2013, 49(4):614-623.
Souron, "New Introduction of Pharmacology," Nanzando Co., 3rd edition, 1987, p. 414-416 (with English translation).
Yanovski et al., "Etiology of the Differences in Corticotropin-Releasing Hormone-Induced Adrenocorticotropin Secretion of Black and White Women," Journal of Clinical Endocrinology & Metabolism, 1996, 81(9):3307-3311.
Dwivedi et al., "Evergreening: a deceptive device in patent rights," Technology in Society, Nov. 1, 2010, 32(4):324-30.
Feldman, "Understanding 'Evergreening': Making Minor Modifications of Existing Medications To Extend Protections," Health Affairs, Jun. 1, 2022, 41(6):801-4.
Gupta et al., "Salts of therapeutic agents: chemical, physicochemical, and biological considerations," Molecules, Jul. 14, 2018, 23(7):1719.
[No Author Listed], "Assessing the Effects of Food on Drugs in INDs and NDAs—Clinical Pharmacology Considerations Guidance for Industry," U.S. Department of Health and Human Services, Food and Drug Administration, Center for Drug Evaluation and Research (CDER), Feb. 2019, Clinical Pharmacology, 17 pages.
[No Author Listed], "Form 8-K: Current Report," Securities and Exchange Commission, Washington, D.C., Apr. 5, 2000, 4 pages.
[No Author Listed], "IUPAC-IUB, Commission on Biochemical Nomenclature—Abbreviated Nomenclature of Synthetic Polypeptides (Polymerized Amino Acids)*—Revised Recommendations (1971)," Biochemistry, 1972, 11(5):942-944.

[No Author Listed], "Neurocrine announces top-line results of corticotropin releasing factor antagonist GSK561679 for treatment of major depressive disorder," Neurocrine Biosciences, Inc., Sep. 14, 2010, 1 page.
[No Author Listed], "Sanofi-Aventis: strong performance of growth platforms in Q1 2011," Sanofi Press Release, Apr. 28, 2011, 13 pages.
[No Author Listed], "Neurocrine Biosciences Reports Positive Phase II Data for Crinecerfont in Adults with Congenital Adrenal Hyperplasia at ENDO Online 2020," Neurocrine Biosciences Inc., Jun. 8, 2020, 3 pages.
[No Author Listed], "Neurocrine Biosciences to Present New Data Analyses for Crinecerfont in Adults with Classical Congenital Adrenal Hyperplasia at Endo 2021," Neurocrine Biosciences Inc., Mar. 20, 2021, 5 pages.
[No Author Listed], "Spruce Biosciences Presents Phase 1 and 2 Data for Tildacerfont in Adults with Congenital Adrenal Hyperplasia from Endocrine Society's 2021 Annual Meeting," Spruce Biosciences, Mar. 17, 2021, 2 pages.
Abdellatif, "Microparticles Formulation as a Targeting Drug Delivery System," J Nanomed Res., 2017, 6(2):00151.
Alejandro et al., "Behavioral, Adrenal, and Sympathetic Responses to Long-Term Administration of an Oral Corticotropin-Releasing Hormone Receptor Antagonist in a Primate Stress Paradigm," The Journal of Clinical Endocrinology & Metabolism, Nov. 1, 2004, 89(11):5729-5737.
Allen et al., "Psychometric evaluation and tests of validity of the Medical Outcomes Study 12-item Sleep Scale (MOS sleep)," Sleep Medicine, May 1, 2009;10(5):531-9.
Ambroziak et al., "Congenital adrenal hyperplasia due to 21-hydroxylase deficiency-management in adults," Polish Journal of Endocrinology, 2010, 61:142-155.
Anthenelli et al., "Sex Differences in the ACTH and Cortisol Response to Pharmacological Probes are Stressor-Specific and Occur Regardless of Alcohol Dependence History," Psychoneuroendocrinology, Aug. 2018, 94:72-82.
Arlt et al., "Health status of adults with congenital adrenal hyperplasia: a cohort study of 203 patients," J Clin Endocrinol Metab., Nov. 2010, 95(11):5110-21.
Arvanitis, AG., et al., "Non-Peptide Corticotropin-Releasing Hormone Antagonists: Syntheses and Structure—Activity Relationships of 2-Anilinopyrimidines and -triazines," J. Med. Chem., 1999, 42(5): 805-818.
Auchus et al., "A pharmacokinetic and biomarker study of the corticotropin-releasing factor receptor antagonist NBI-77860 in adult females with classic, 21-hydroxylase deficiency, congenital adrenal hyperplasia (CAH)," OR06 HPA Axis and Adrenal: Receptors To Clinical Impact, Platform presentation at the 97th annual meeting of the Endocrine Society (Endo 2015), Mar. 2015, 1 page.
Auchus et al., "Approach to the patient: the adult with congenital adrenal hyperplasia," J Clin Endocrinol Metab., Jul. 2013, 98(7):2645-55.
Auchus et al., "Crinecerfont (NBI-74788), a novel CRFI receptor antagonist, reduces adrenal androgens and precursors in patients with classic congenital adrenal hyperplasia: Results from a phase 2, multiple-dose study," Poster Presentation, Presented Virtually at The 22nd European Congress of Endocrinology, Sep. 5-9, 2020, 1 page.
Auchus et al., "Crinecerfont lowers elevated hormone markers in adults with 21-hydroxylase deficiency congenital adrenal hyperplasia," The Journal of Clinical Endocrinology & Metabolism, 2022, 107(3):801-812.
Auchus et al., "OR18-4 Crinecerfont (NBI-74788), a Novel CRFI Receptor Antagonist, Lowers Adrenal Androgens and Precursors in Adolescents with Classic Congenital Adrenal Hyperplasia," Journal of the Endocrine Society, 2022, 6(Supplement 1):A618.
Auchus et al., "Response to Crinecerfont Treatment in Adults with Classic Congenital Adrenal Hyperplasia Is Correlated with Elevated Baseline Hormone Levels But Not Glucocorticoid Dose," Abstract submitted to ECE for consideration at 2023 annual meeting, prepared on Mar. 2023, 2 pages.
Auchus et al., "The Effects of Crinecerfont (NBI-74788), a Novel CRFI Receptor Antagonist, on Adrenal Androgens and Precursors in

(56) References Cited

OTHER PUBLICATIONS

Patients with Classic Congenital Adrenal Hyperplasia: Results from A Multiple-Dose Phase 2 Study," J Endocrin Soc., 2020, 4(Supplement 1):OR25-03.
Auchus et al., "The effects of crinecerfont (NBI-74788), a novel CRFI receptor antagonist, on adrenal androgens and precursors in patients with classic congenital adrenal hyperplasia: Results from a multiple-dose phase 2 study," Journal of the Endocrine Society, 2020, 4(Abstract Supplement):A111.
Auchus RJ, et al., "Management of the adult with congenital adrenal hyperplasia," Int J Ped Endocrinol., 2010, Article ID 614107: 1-9.
Bachelot A, et al., "Bone health should be an important concern in the care of patients affected by 21 hydroxylase deficiency," Int J Ped Endocrinol., 2010, Article ID 326275: 1-7.
Bakshi VP, et al., "Reduction of Stress-Induced Behavior by Antagonism of Corticotropin-Releasing Hormone 2 (CRH2) Receptors in Lateral Septum or CRH1 Receptors in Amygdala", J. Neurosci., 2002, 22(7): 2926-2935.
Bale et al., "Overview on Therapeutic Applications of Microparticulate Drug Delivery Systems," Crit Rev Ther Drug Carrier Syst., 2016, 33(4):309-361.
Barreau F. et al., "Pathways involved in gut mucosal barrier dysfunction induced in adult rats by maternal deprivation: corticotrophin-releasing factor and nerve growth factor interplay," Journal of Physiology-London, 2007, 580(1):347-356.
Behan DP et al., "Neurobiology of corticotropin releasing factor (CRF) receptors and CRF-binding protein: implications for the treatment of CNS disorders," Molecular Psychiatry, 1996, 1(4):265-277.
Belza et al., "A systematic review of studies using the multidimensional assessment of fatigue scale," Journal of Nursing Measurement, May 1, 2018;26(1):36-74.
Belza, "Comparison of self-reported fatigue in rheumatoid arthritis and controls," J Rheumatol., Apr. 1995, 22(4):639-643.
Benedetti et al., "The Biochemical and Neuroendocrine Bases of the Hyperalgesic Nocebo Effect," J Neurosci., Nov. 15, 2006, 26(46):12014-12022.
Berge et al., "Pharmaceutical salts," Journal of Pharmaceutical Sciences, 1977, 66(1):1-9.
Bleicken B, et al., "Improvement of health-related quality of life in adult women with 21-hydroxylase deficiency over a seven-year period," Endocr J., 2012, 59(10):931-939.
Blume et al., "Oral medicine acceptance in infants and toddlers: measurement properties of the caregiver-administered Children's acceptance tool (CareCAT)," BMC pediatrics, 2018, 18:117.
Bonfig et al., "Reduced final height outcome in congenital adrenal hyperplasia under prednisone treatment: deceleration of growth velocity during puberty," J Clin Endocrinol Metab., May 2007, 92(5):1635-1639.
Bonfig W. et al., "Hydrocortisone Dosing During Puberty in Patients With Classical Congenital Adrenal Hyperplasia: An Evidence-Based Recommendation," J Clin Endocrinol Metab., 2009, 94(10):3882-3888.
Bornstein et al., "Chronic effects of a nonpeptide corticotropin-releasing hormone type I receptor antagonist on pituitary-adrenal function, body weight, and metabolic regulation," Endocrinology, 1998, 139(4):1546-1555.
Brazier et al., "Validating the SF-36 health survey questionnaire: new outcome measure for primary care," BMJ, Jul. 18, 1992, 305(6846):160-164.
Brunson KL, et al., "Corticotropin-Releasing Hormone (CRH) Downregulates the Function of Its Receptor (CRF1) and Induces CRF1 Expression in Hippocampal and Cortical Regions of the Immature Rat Brain," Experimental Neurology, 2002, 176(1):75-86.
Buxton et al., "Pharmacokinetics: The Dynamics of Drug Absorption, Distribution, Metabolism, and Elimination," Goodman & Gilman's The Pharmacological Basis of Therapeutics., Brunton L.L. ed., 12th ed. 2011, Chapter 2, 29 pages.

Caira, "Crystalline polymorphism of organic compounds," Design of Organic Solids, 1998, pp. 163-208.
Caresfoundation.org [Online], "Emergency Instructions—Treatment for Congenital Adrenal Hyperplasia in times of stress," 2014, [retrieved on Mar. 6, 2023], retrieved from: URL<https://caresfoundation.org/wp-content/uploads/2014/08/EmergencyBrochure2014.pdf>, 2 pages.
CAS Registry No. 321839-75-2, Feb. 15, 2001, 1 page.
Chakhtoura Z. et al., "Impact of total cumulative glucocorticoid dose on bone mineral density in patients with 21-hydroxylase deficiency," Eur J Endocrinol., 2008, 158(6):879-887.
Charmandari et al., "Bioavailability of oral hydrocortisone in patients with congenital adrenal hyperplasia due to 21-hydroxylase deficiency," J Endocrinol, Apr. 2001, 169(1):65-70.
Chatzaki, E, et al., "CRF receptor type 1 and 2 expression and anatomical distribution in the rat colon," Journal of Neurochemistry, 2004, 90: 309-316.
Chen C, et al., "NBI 30775 (R121919), an Orally Active Antagonist of the Corticotropin-releasing Factor (CRF) Type-1 Receptor for the Treatment of Anxiety and Depression," Drug Development Research, 2005, 65(4):216-226.
Chen C, et al., "1-Alkyl-3-amino-5-aryl-1H-[1,2,4]triazoles: novel synthesis via cyclization of N-Acyl-S-methylisothioureas with alkylhydrazines and their potent corticotropin-Releasing factor-1 (CRF1) receptor antagonist activities," Bioorganic & Medicinal Chemistry Letters, 2001, 11(24): 3165-3168.
Chen C, et al., "Design and Synthesis of a Series of Non-Peptide High-Affinity Human Corticotropin-Releasing Factor1 Receptor Antagonists," J. Med. Chem., 1996, 39(22): 4358-4360.
Chen C, et al., "Optimization of 3-phenylpyrazolo[1,5-a]pyrimidines as potent corticotropin-releasing factor-1 antagonists with adequate lipophilicity and water solubility" Bioorganic & Medicinal Chemistry Letters, 2004, 14(14): 3669-3673.
Chen et al., "Design of 2,5-dimethyl-3-(6-dimethyl-4-methylpyridin-3-yl)-7-dipropylaminopyrazolo[1,5-a] pyrimidine (NBI 30775/R121919) and structure-activity relationships of a series of potent and orally active corticotropin-releasing factor receptor antagonists," Journal of Medicinal Chemistry, 2004, 47(19):4787-4798.
Chen Y, et al., "Cellular and molecular mechanisms of hippocampal activation by acute stress are age-dependent," Molecular Psychiatry, 2006, 11: 992-1002.
Chen Y, et al., "Modulation of dendritic differentiation by corticotropin-releasing factor in the developing hippocampus," Proceedings of the National Academy of Sciences, 2004, 101(44): 15782-15787.
Cheng and Speiser, "Treatment outcomes in congenital adrenal hyperplasia," Adv Pediatr., 2012, 59(1):269-281.
Claahsen-van der Grinten et al., "Prevalence of testicular adrenal rest tumours in male children with congenital adrenal hyperplasia due to 21-hydroxylase deficiency," Eur J Endocrinol., Sep. 2007, 157(3):339-344.
Claustre et al., "Effects of the Vasopressin ($V_{1b}$) Receptor Antagonist, SSR149415, and the Corticotropin-Releasing Factor 1 Receptor Antagonist, SSR125543, on FG 7142-induced Increase in Acetylcholine and Norepinephrine Release in the Rat," Neuroscience, 2006, 141:1481-1488.
Clinicaltrials.gov [Online], "Safety, Tolerability, Pharmacokinetics, and Pharmacodynamics of NBI-74788 in Pediatric Subjects With Congenital Adrenal Hyperplasia," First Posted Aug. 5, 2019, [Retrieved on Nov. 30, 2022], retrieved from: URL<https://clinicaltrials.gov/ct2/show/NCT04045145>, 7 pages.
Clinicaltrials.gov, "A study in patients with irritable bowel syndrome to measure hormone response after dosing with GW876008 and Gsk561679," U.S. National Library of Medicine, Aug. 6, 2007, retrieved on Jun. 11, 2020, retrieved from URL: https://clinicaltrials.gov/ct2/show/NCT00511563?term=NCT00511563&draw=1&rank=1, 5 pages.
Clinicaltrials.gov, "A study of the effects of a new antidepressant treatment (GSK561679) in females with major depressive disorder," U.S. National Library of Medicine, Aug. 13, 2008, retrieved on Jun. 11, 2020, retrieved from URL: https://clinicaltrials.gov/ct2/show/NCT00733980?term=NCT00733980&draw=2&rank=1, 14 pages.
Clinicaltrials.gov, "A study to compare the putative anxiolytic effect of 2 new drugs in subjects with social anxiety disorder," U.S.

(56) References Cited

OTHER PUBLICATIONS

National Library of Medicine, Nov. 7, 2007, retrieved on Jun. 11, 2020, retrieved from URL: https://clinicaltrials.gov/ct2/show/NCT00555139?term=NCT00555139&draw=2&rank=1, 10 pages.
Clinicaltrials.gov, "CRFI antagonist GSK561679 in alcoholism," U.S. National Library of Medicine, Aug. 24, 2010, retrieved on Sep. 25, 2020, retrieved from URL: https://clinicaltrials.gov/ct2/show/NCT01187511?term=NCT01187511&draw=2&rank=1, 20 pages.
Clinicaltrials.gov, "Evaluation of GSK561679 in women with post-traumatic stress disorder," U.S. National Library of Medicine, Nov. 25, 2009, retrieved on Jun. 11, 2020, retrieved from URL: https://clinicaltrials.gov/ct2/show/NCT01018992?term=NCT01018992&draw=2&rank=1, 9 pages.
Collier et al., "Radiosynthesis and In-Vivo Evaluation of the Pseudopeptide 8-Opioid Antagonist [$^{125}$I]-ITIPP($\Psi$)," XIIIth International Symposium on Radiopharmaceutical Chemistry, J. Labelled Cpd. Radiopharm., 1999, 42(Suppl. 1):S264-S266.
Cottone P, et al., "CRF system recruitment mediates dark side of compulsive eating," Proceedings of the National Academy of Sciences, 2009, 106(47): 20016-20020.
Cui et al., "Modification of sample size in group sequential clinical trials," Biometrics, 1999, 55(3):853-857.
Curtis AL, et al., "Pharmacological comparison of two corticotropin-releasing factor antagonists: in vivo and in vitro studies," Journal of Pharmacology and Experimental Therapeutics, 1994, 268(1): 359-365.
Dai et al., "A Generic Headspace GC Method for Residual Solvents in Pharmaceuticals: Benefits, Rationale, and Adaptations for New Chemical Entities," LCGC North America, 2010, 28(1):54-66.
Dauber et al., "Nocturnal dexamethasone versus Hydrocortisone for the treatment of children with congenital adrenal hyperplasia," Int. J. of Pediatric Endocrinology, 2010, 2010(1):347636.
De Vries et al., "Mental health of a large group of adults with disorders of sex development in six European countries," Psychosomatic Medicine, 2019, 81(7):629-640.
Deak et al., "The impact of the nonpeptide corticotropin-releasing hormone antagonist antalarmin on behavioral and endocrine responses to stress," Endocrinology, 1999, 140(1):79-86.
Derendorf et al., "Pharmacokinetics and oral bioavailability of hydrocortisone," J Clin Pharmacol. May 1991, 31(5):473-476.
Douma et al., "CRF1 receptor antagonists do not reverse pharmacological disruption of prepulse inhibition in rodents," Psychopharmacology, 2014, 231:1289-1303.
Dournes et al., "Deep brain stimulation in treatment-resistant depression in mice: comparison with the $CRF_1$ antagonist, SSR125543," Progress in Neuro-Psychopharmacology & Biological Psychiatry, 2013, 40:213-220.
Doyon et al., "Effects of the $CRF_1$ receptor antagonist SSR125543 on energy balance and food deprivation-induced in neuronal activation in obese Zucker rats," J. of Endocrinology, 2007, 193:11-19.
Dudzinska B, et al., "Sexual Well-Being in Adult Male Patients with Congenital Adrenal Hyperplasia," Int J Endocrinol., 2014, ID 469289: 1-9.
Dunn et al., "Physiological and behavioral responses to corticotropin-releasing factor administration: is CRF a mediator of anxiety or stress responses?" Brain Res Brain Res Rev., May-Aug. 1990, 15(2):71-100.
Dyck B, et al., "Potent, Orally Active Corticotropin-Releasing Factor Receptor-1 Antagonists Containing a Tricyclic Pyrrolopyridine or Pyrazolopyridine Core," J. Med. Chem., 2005, 48(12): 4100-4110.
Elder et al., "The utility of sulfonate salts in drug development," Journal of Pharmaceutical Sciences, Jan. 1, 2010, 99(7):2948-2961.
El-Maouche et al., "Adrenal morphology and associated comorbidities in congenital adrenal hyperplasia," Clinical Endocrinology, 2019, 91(2):247-255.
El-Maouche et al., "Longitudinal assessment of illnesses, stress dosing, and illness sequelae in patients with congenital adrenal hyperplasia," The Journal of Clinical Endocrinology & Metabolism, 2018, 103(6):2336-2345.
El-Maouche et al., "Congenital Adrenal Hyperplasia," Lancet., Nov. 11, 2017, 390:2194-2210.
Elnecave et al., "Bone mineral density in girls with classical congenital adrenal hyperplasia due to CYP21 deficiency," J Pediatr Endocrinol Metab., Dec. 2008, 21(12):1155-62.
Esteban et al., "Daily cortisol production rate in man determined by stable isotope dilution/mass spectrometry," J Clin Endocrinol Metab., Jan. 1991, 72(1):39-45.
EU Clinical Trials Register, "Abbreviated Style Clinical Study Report," Sanofi-Aventis Group, Sep. 5, 2011, 4 pages.
Fahmy et al., "Structure and Function of Small Non-Peptide CRF Antagonists and their Potential Clinical Use," Curr Mol Pharmacol., 2017, 10(4):270-281.
Falhammar et al., "Fertility, sexuality and testicular adrenal rest tumors in adult males with congenital adrenal hyperplasia," Eur J Endocrinol., Mar. 2012, 166(3):441-449.
Falhammar et al., "Fractures and bone mineral density in adult women with 21-hydroxylase deficiency," J Clin Endocrinol Metab. Dec. 2007; 92(12):4643-4649.
Falhammar et al., "Increased mortality in patients with congenital adrenal hyperplasia due to 21-hydroxylase deficiency," J Clin Endocrinol Metab., Dec. 2014, 99(12):E2715-21.
Falhammar et al., "Quality of life, social situation, and sexual satisfaction, in adult males with congenital adrenal hyperplasia," Endocrine, 2014, 47:299-307.
Finkielstain et al., "Clinical Characteristics of a Cohort of 244 Patients with Congenital Adrenal Hyperplasia," J Clin Endocrinol Metab, 2012, 97(12):4429-4438.
Fleck et al., "Binding Kinetics Redefine the Antagonist Pharmacology of the Corticotropin-Releasing Factor Type 1 Receptor," The Journal of Pharmacology and Experimental Therapeutics, 2012, 341(2):518-531.
Forest, "Recent advances in the diagnosis and management of congenital adrenal hyperplasia due to 21-hydroxylase deficiency," Human Reproduction Update, 2004, 10(6): 469-485.
Frederic et al., "Radiosynthesis of [C-11]SSR126374, a new selective CRF1 antagonist," Journal of Labelled Compounds & Radiopharmaceuticals, 2011, 54(1):273.
Fuqua et al., "Duration of suppression of adrenal steroids after glucocorticoid administration," International Journal of Pediatric Endocrinology, 2010, 2010:1-8.
Gilban D, et al., "Health related quality of life of children and adolescents with congenital hyperplasia in Brazil," Health Qual Life Outcomes, 2014, 12:107 (9 pages).
Gilligan et al., "Corticotropin-releasing factor antagonists: recent advances and exciting prospects for the treatment of human diseases," Curr. Opin. In Drug Discov. & Develop., 2004, 7(4)487-497.
Grammatopoulos et al., Functional characteristics of CRH receptors and potential clinical applications of CRH-receptor antagonists, Trends in Endocrinology & Metabolism, 2002, 13(10):436-444.
Griebel et al., "4-(2-Chloro-4-methoxy-5-methylphenyl)-N-[(1S)-2-cyclopropyl-1-(3-fluoro-4-methylphenyl)ethyl]5-methyl-N-(2-propynyl)-1,3-thiazol-2-amine Hydrochloride (SSR125543A), a Potent and Selective Corticotrophin-Releasing factor(1) Receptor Antagonist. II. Characterization in Rodent Models of Stress-Related Disorders," J. Pharmacol. Exp. Ther., 2002, 301(1):333-345.
Grigoriadis DE, "Corticotropin-Releasing Factor Receptor Antagonists: Potential Novel Therapies for Human Disease," Celltransmissions, 2003, 19(4): 3-10.
Grigoriadis DE, "The corticotropin-releasing factor receptor: a novel target for the treatment of depression and anxiety-related disorders," Expert Opin. Ther. Targets, 2005, 9(4): 651-684.
Grigoriadis DE, et al., "$^{125}$I-Tyr$^0$-Sauvagine: A Novel High Affinity Radioligand for the Pharmacological and Biochemical Study of Human Corticotropin-Releasing Factor $_{2\alpha}$ Receptors," Molecular Pharmacology, 1996, 50:679-686.
Grigoriadis DE, et al., "Drugability of Extracellular Targets: Discovery of Small Molecule Drugs Targeting Allosteric, Functional, and Subunit-Selective Sites on GPCRs and Ion Channels," Neuropsychopharmacology, 2009, 34: 106-125.
Grigoriadis, DE, et al., "The CRF Receptor Structure, Function and Potential for Therapeutic Intervention," Current Medicinal Chemistry—Central Nervous System Agents, 2001, 1(1): 63-97.

(56) References Cited

OTHER PUBLICATIONS

Gross RS, et al., "Design and Synthesis of Tricyclic Corticotropin-Releasing Factor-1 Antagonists," J. Med. Chem., 2005, 48(18): 5780-5793.

Grossi et al., "Development and validation of the short version of the Psychological General Well-Being Index (PGWB-S)," Health and Quality of Life Outcomes, 2006, 4(1):1-8.

Gully et al., "4-(2-Chloro-4-methoxy-5-methylphenyl)-N-[(1S)-2-cyclopropyl-1-(3-fluoro-4-methylphenyl)ethyl]5-methyl-N-(2-propynyl)-1,3-thiazol-2-amine hydrochloride (SSR125543A): A potent and selective corticotrophin-releasing factor$_1$ receptor antagonist. I. Biochemical and Pharmacological Characterization," Journal of Pharmacology and Experimental Therapeutics, 2002, 301(1):322-332.

Guo Z, et al., "Design and Synthesis of Tricyclic Imidazo[4,5-b]pyridin-2-ones as Corticotropin-Releasing Factor-1 Antagonists," J. Med. Chem., 2005, 48(16): 5104-5107.

Habib et al., "Oral administration of a corticotropin-releasing hormone receptor antagonist significantly attenuates behavioral, neuroendocrine, and autonomic responses to stress in primates," Proceedings of the National Academy of Sciences, 2000, 97(11):6079-6084.

Halper et al., "Health-related quality of life in children with congenital adrenal hyperplasia," Health Qual. Life Outcomes, 2017, 15(1):194.

Hamilton, "Needle Phobia: A Neglected Diagnosis," J Fam Pract., Aug. 1995, 41(2):169-175.

Han et al., "Quality of life in adults with congenital adrenal hyperplasia relates to glucocorticoid treatment, adiposity and insulin resistance: United Kingdom Congenital Adrenal Hyperplasia Adult Study Executive (CaHASE)" Eur J Endocrinol., May 3, 2013, 168(6):887-893.

Han TS, et al., "Glucocorticoid treatment regimen and health outcomes in adults with congenital adrenal hyperplasia," Clin Endocrinol, 2013, 8:197-203.

Han TS, et al., "Relationship Between Final Height and Health Outcomes in Adults with Congenital Adrenal Hyperplasia: United Kingdom Congenital Adrenal Hyperplasia Adult Study Executive (CaHASE)," J Clin Endocrinol Metab., 2014, 99(8):E1547-E1555.

Han TS, et al., "Treatment and health outcomes in adults with congenital adrenal hyperplasia," Nat Rev Endocrinol., 2014, 10:115-124.

Hannah-Shmouni et al., "Genetics of Congenital Adrenal Hyperplasia," Best Pract Res Clin Endocrinol Metab., Apr. 2009, 23(2):181-192.

Hauger RL, et al., "International Union of Pharmacology. XXXVI. Current Status of the Nomenclature for Receptors for Corticotropin-Releasing Factor and Their Ligands," Pharmacological Reviews, 2003, 55(1): 21-26.

He et al., "Changes in adrenal and gonadal androgens after 14-day treatment with a CRF1 receptor antagonist, crinecerfont (NBI-74788), in men with classic 21-hydroxylase deficiency," Journal of the Endocrine Society, 2021, 5(Supplement_1):A78.

Heike et al., "Treatment of depression with the CRH-1-receptor antagonist R121919: endocrine changes and side effects", J Psych Res., Nov. 1, 2003, 37(8):525-533.

Heinrichs SC, et al., "Brain Penetrance, Receptor Occupancy and Antistress In Vivo Efficacy of a Small Molecule Corticotropin Releasing Factor Type I Receptor Selective Antagonist," Neuropsychopharmacology, 2002, 27: 194-202.

Herdman et al., "Development and preliminary testing of the new five-level version of EQ-5D (EQ-SD-5L)," Qual Life Res., Dec. 2011, 20(10):1727-1736.

Hertzberg et al., "Birth prevalence rates of newborn screening disorders in relation to screening practices in the United States," J Pediatr., Oct. 2011, 159(4):555-560.

Hines et al., "Spatial abilities following prenatal androgen abnormality: targeting and mental rotations performance in individuals with congenital adrenal hyperplasia," Psychoneuroendocrinology, Nov. 2003, 28(8): 1010-1026.

Hoare et al., "Mechanism of Corticotropin-Releasing Factor Type I Receptor Regulation by Nonpeptide Antagonists," Molecular Pharmacology, 2003, 63(3):751-756.

Hoare SRJ, et al., "Allosteric Ligands for the Corticotropin Releasing Factor Type 1 Receptor Modulate Conformational States Involved in Receptor Activation," Molecular Pharmacology, 2008, 73(5): 1371-1380.

Hoare SRJ, et al., "Conformational states of the corticotropin releasing factor I (CRF1) receptor: detection, and pharmacological evaluation by peptide ligands," Peptides, 2003, 24(12): 1881-1897.

Hoare SRJ, et al., "Ligand Affinity for Amino-Terminal and Juxtamembrane Domains of the Corticotropin Releasing Factor Type I Receptor: Regulation by G-Protein and Nonpeptide Antagonists," Biochemistry, 2004, 43(13): 3996-4011.

Hoare SRJ, et al., "Single amino acid residue determinants of non-peptide antagonist binding to the corticotropin-releasing factor1 (CRF1) receptor," Biochemical Pharmacology, 2006, 72(2): 244-255.

Holm, "A simple sequentially rejective multiple test procedure," Scandinavian Journal of Statistics, 1979, 65-70.

Huang CQ, et al., "Design and synthesis of 3-(2-pyridyl)pyrazolo[1,5-a]pyrimidines as potent CRF1 receptor antagonists," Bioorganic & Medicinal Chemistry Letters, 2004, 14(15): 3943-3947.

Huang CQ, et al., "Design, synthesis, and SAR of 2-dialkylamino-4-arylpyrimidines as potent and selective corticotropin-releasing factor1 (CRF1) receptor antagonists," Bioorganic & Medicinal Chemistry Letters, 2004, 14(9): 2083-2086.

Huang CQ, et al., "Synthesis and SAR of 8-Arylquinolines as potent corticotropin-Releasing factor1 (CRF1) receptor antagonists," Bioorganic & Medicinal Chemistry Letters, 2003, 13(19): 3375-3379.

Huang CQ, et al., "Synthesis of 1-methyl-3-phenylpyrazolo[4,3-b]pyridines via a methylation of 4-phthalimino-3-phenylpyrazoles and optimization toward highly potent corticotropin-releasing factor type-1 antagonists," Bioorganic & Medicinal Chemistry Letters, 2003, 13(19): 3371-3374.

Iranmanesh et al., "Glucose Ingestion Selectively Amplifies ACTH and Cortisol Secretory-Burst Mass and Enhances Their Joint Synchrony in Healthy Men," J Endocrinol and Metab., Sep. 2011, 96(9):2882-2888.

Ising M, et al., "High-Affinity CRF1 Receptor Antagonist NBI-34041: Preclinical and Clinical Data Suggest Safety and Efficacy in Attenuating Elevated Stress Response," Neuropsychopharmacology, 2007, 32:1941-1949.

Ivy AS, et al., "Hippocampal Dysfunction and Cognitive Impairments Provoked by Chronic Early-Life Stress Involve Excessive Activation of CRH Receptors," J. Neurosci., 2010, 30(39):13005-13015.

Jain et al., "Spray Drying in Pharmaceutical Industry: A review," Research Journal of Pharmaceutical Dosage Forms and Technology, Apr. 10, 2012, 4(2):74-79.

Jenkins-Jones et al., "Poor compliance and increased mortality, depression and healthcare costs in patients with congenital adrenal hyperplasia," European Journal of Endocrinology, 2018, 178(4):309-320.

Jha et al., "SUN-371 Successful Induction of Fertility with Low-Dose Dexamethasone in a Patient with Congenital Adrenal Hyperplasia and Testicular Adrenal Rest Tumor," Journal of the Endocrine Society, 2019, 3(Supplement 1):SUN-371.

Johannsen et al., "Impaired cognitive function in women with congenital adrenal hyperplasia," J Clin Endocrinol Metab., Apr. 2006, 91(4):1376-1381.

Katkade et al., "Real world data: an opportunity to supplement existing evidence for the use of long-established medicines in health care decision making," J Multidiscip Healthc., 2018, 11:295-304.

Kebne et al., "Therapeutic Utility of Non-Peptidic CRF$_1$ Receptor Antagonists in Anxiety, Depression, and Stress-Related Disorders: Evidence from Animal Models," Pharmacol Ther., Dec. 2010; 128(3):460-487.

Kiddoo DA, et al., "Impact of state of arousal and stress neuropeptides on urodynamic function in freely moving rats," Am J Physiol Regul Integr Comp Physiol, 2006, 290:R1697-R1706.

(56) References Cited

OTHER PUBLICATIONS

Kim et al., "Cardiovascular Disease Risk in Adult Women with Congenital Adrenal Hyperplasia Due to 21-hydroxylase Deficiency," Semin Reprod Med, 2009, 27(4):316-321.

King et al., "Long-Term Corticosteroid Replacement and Bone Mineral Density in Adult Women with Classical Congenital Adrenal Hyperplasia," The Journal of Clinical Endocrinology & Metabolism, 2006, 91(3):865-869.

Kitagawa et al., "Basic Pharmaceutical Science Textbook Series 20," Pharmaceutical Science, 2nd print, Kagaku-Dojin Publishing Co., Inc., 2012, p. 16-19.

Koelsch et al., "The Impact of Acute Stress on Hormones and Cytokines, and How Their Recovery is Affected by Music-Evoked Positive Mood," Sci Reps., Mar. 2016, 6:1-11.

Koob et al., "Update on Corticotropin-Releasing Factor Pharmacotherapy for Psychiatric Disorders: A Revisionist View," Neuropsychopharmacology Reviews, 2012, 37:308-309.

Kosoyan HP, et al., "The $CRF_1$ receptor antagonist, NBI-35965, abolished the activation of locus coeruleus neurons induced by colorectal distension and intracisternal CRF in rats," Brain Research, 2005, 1056(1):85-96.

Kulshreshtha B, et al., "Pubertal development among girls with classical congenital adrenal hyperplasia initiated on treatment at different ages," Indian J Endocrinol Metab., 2012, 16(4):599-603.

Le Bas et al., "Radioiodinated analogs of EP 00652218 for the exploration of the tachykinin NK1 receptor by spect," Journal of Labelled Compounds and Radiopharmaceuticals, 2001, 44(S1):S280-S282.

Lehmacher et al., "Adaptive sample size calculations in group sequential trials," Biometrics, 1999, 55(4):1286-1290.

Lekarev et al., "Adrenal disease in pregnancy," Best Practice & Research, Clinical Endocrinology & Metabolism, Dec. 2011, 25(6):959-973.

Li et al., "The pharmacology of DMP696 and DMP904, non-peptidergic $CRF_1$ receptor antagonists," CNS Drug Reviews, 2005, 11(1):21-52.

Liapakis G, et al., "Members of CRF Family and their Receptors: From Past to Future," Current Medicinal Chemistry, 2011, 18(17):2583-2600.

Linder et al., "Cortisol production rate in childhood and adolescence," J Pediatr, Dec. 1990, 117(6):892-896.

Liu J, et al., "Corticotropin-Releasing Factor and Urocortin I Modulate Excitatory Glutamatergic Synaptic Transmission," Journal of Neuroscience, 2004, 24(16): 4020-4029.

Loechner et al., "Alternative Strategies for the Treatment of Classical Congenital Adrenal Hyperplasia: Pitfalls and Promises," International Journal of Pediatric Endocrinology, vol. 2010, No. 1, Jun. 8, 2010, Article ID 670960, 10 pages.

Logachev et al., "Congenital Adrenal Hyperplasia: Modern Problems of Terminology and Treatment," Pediatrics, Apr. 19, 2012, 91(3):130-135 pages (with English Translation).

Louis et al., "Antidepressant-like Effects of the Corticotropin-Releasing Factor 1 Receptor Antagonist, SSR125543, and the Vasopressin 1b Receptor Antagonist, SSR149415, in a DRL-72 S Schedule in the Rat," Neuropsychopharmacology, 2006, 31:2180-2187.

Lovenberg TW, et al., "Cloning and characterization of a functionally distinct corticotropin-releasing factor receptor subtype from rat brain," Proceedings of the National Academy of Sciences, 1995, 92(3): 836-840.

Lowe RF, et al., "Rational Design, Synthesis, and Structure-Activity Relationships of Aryltriazoles as Novel Corticotropin-Releasing Factor-1 Receptor Antagonists," J. Med. Chem., 2005, 48(5):1540-1549.

Maciejewski-Lenoir D, et al., "Selective Impairment of Corticotropin-Releasing Factor1 (CRF1) Receptor-Mediated Function Using CRF Coupled to Saporin," Endocrinology, 2000, 141(2):498-504.

Mackay, KB, et al., "Neuroprotective Effects of the CRF1 Antagonist R121920 after Permanent Focal Ischemia in the Rat," Journal of Cerebral Blood Flow & Metabolism, 2001, 21(10): 1208-1214.

Malouf et al., "Cognitive outcome in adult women affected by congenital adrenal hyperplasia due to 21-hydroxylase deficiency," Horm Res., 2006, 65(3):142-150.

Martínez V, et al., "Central CRF, urocortins and stress increase colonic transit via CRF1 receptors while activation of CRF2 receptors delays gastric transit in mice," J Physiol., 2004, 556.1: 221-234.

Martinez-Aguayo et al., "Testicular adrenal rest tumors and Leydig and Sertoli cell function in boys with classical congenital adrenal hyperplasia," J Clin Endocrinol Metab., Dec. 2007, 92(12):4583-9.

McCarthy JR, et al., "Chapter 2. Recent Progress in Corticotropin-Releasing Factor Receptor Agents," Annual Reports in Medicinal Chemistry, 1999, 34: 11-20.

McCarthy JR, et al., "Recent advances with the CRF1 receptor: design of small molecule inhibitors, receptor subtypes and clinical indications," Curr Pharm Des., 1999, 5(5):289-315.

Medlineplus.gov, "21-Hydroxylase Deficiency," NIH US National Library of Medicine, Updated Aug. 18, 2020 [retrieved Dec. 13, 2021], retrieved from URL<https://medlineplus.gov/genetics/condition/21-hydroxylase-deficiency/>, 6 pages.

Mehta et al., "Adaptive increase in sample size when interim results are promising: a practical guide with examples," Statistics in Medicine, 2011, 30(28):3267-3284.

Merke et al., "Congenital adrenal hyperplasia," Lancet, 2005, 365:2125-2136.

Merke et al., "Congenital adrenal hyperplasia: epidemiology, management and practical drug treatment," Paediatr Drugs., 2001, 3(8):599-611.

Merke et al., "Flutamide, testolactone, and reduced hydrocortisone dose maintain normal growth velocity and bone maturation despite elevated androgen levels in children with congenital adrenal hyperplasia," J Clin Endocrinol Metab., Mar. 2000, 85(3):1114-1120.

Merke et al., "Management of adolescents with congenital adrenal hyperplasia," Lancet Diabetes Endocrinol., Dec. 2013, 1(4):341-352.

Merke et al., "New ideas for medical treatment of congenital adrenal hyperplasia," Endocrinol. Metab. Clin. North. Am., 2001, 30(1):121-135.

Merke et al., "NIH conference: Future directions in the study and management of congenital adrenal hyperplasia due to 21-hydroxylase deficiency," Ann. Intern. Med., 2002, 136:320-334.

Merke et al., "Congenital Adrenal Hyperplasia Due to 21-Hydroxylase Deficiency," N Engl J Med., Sep. 24, 2020, 383(13):1248-1261.

Meslamani et al., "Computational profiling of bioactive compounds using a target-dependent composite workflow," J. Chem. Inf. Model., 2013, 2322-2333.

Migeon et al., "Congenital Adrenal Hyperplasia Owing to 21-Hydroxylase Deficiency," Endocrinology and Metabolism Clinics of North America, 2001, 30(1):193-206.

Miller et al., "Emergency management of adrenal insufficiency in children: advocating for treatment options in outpatient and field settings," Journal of Investigative Medicine, 2020, 68(1):16-25.

Million et al., "The newly developed CRF1-receptor antagonists, NGD 98-2 and NGD 9002, suppress acute stress-induced stimulation of colonic motor function and visceral hypersensitivity in rats," PLOS One, 2013, 8(9):e73749.

Million M, et al., "A novel water-soluble selective CRF1 receptor antagonist, NBI 35965, blunts stress-induced visceral hyperalgesia and colonic motor function in rats," Brain Research, 2003, 985(1):32-42.

Mims et al., "Plasma ACTH in Rats Following Medical Adrenalectomy," Journal of the National Medical Association 69(3):145-147, 1977.

Morikawa S, et al., "Results from 28 years of Newborn Screening for Congenital Adrenal Hyperplasia in Sapporo," Clin Pediatr Endocrinol., 2014, 23(2):35-43.

Mullins et al., "Brief psychiatric rating scale for children: quantitative scoring of medical records," Psychiatry Research, 1986, 19(1):43-49.

Muthusamy et al., "Clinical review: Adult height in patients with congenital adrenal hyperplasia: a systematic review and metaanalysis," J Clin Endocrinol Metab., Sep. 2010, 95(9):4161-4172.

(56) References Cited

OTHER PUBLICATIONS

Nebesio TD, et al., "Growth and Reproductive Outcomes in Congenital Adrenal Hyperplasia," Int J Pediatr Endocrinol., 2010, Article ID 298937, 1-10.

Nermoen et al., "Subjective health status in men and women with congenital adrenal hyperplasia: a population-based survey in Norway," Eur J Endocrinol., Sep. 2010, 163(3):453-459.

*Neurocrine Biosciences, Inc.*, Petitioner, v. *Spruce Biosciences, Inc.*, Patent Owner, Case No. PGR2021-00088, U.S. Pat. No. 10,849,908, Declaration of Robert M. Carey, M.D., dated May 28, 2021, 154 pages.

Newfield et al., "Crinecerfont (NBI-74788), a Novel $CRF_1$ Receptor Antagonist, Lowers Adrenal Androgens and Precursors in Adolescents with Classic Congenital Adrenal Hyperplasia," Abstract submitted to ECE for consideration at 2023 annual meeting, 2 pages.

Newfield et al., "Crinecerfont (NBI-74788), a novel $CRF_1$ receptor antagonist, lowers adrenal androgens and precursors in adolescents with classic congenital adrenal hyperplasia," Presentation Slides presented at the 104th annual meeting and expo of the Endocrine Society (Endo 2022), Atlanta, GA, Jun. 2022, 13 pages.

Newfield R.S., "ACTH receptor blockade: A novel approach to treat congenital adrenal hyperplasia, or Cushing's disease," Medical Hypotheses, 2010, 74:705-706.

Nieves-Remacha et al., "Scale-up of N-alkylation reaction using phase-transfer catalysis with integrated separation in flow," Reaction Chemistry & Engineering, 2019, 4(2):334-345.

Nokoff et al., "Sex differences in effects of obesity on reproductive hormones and glucose metabolism in early puberty," The Journal of Clinical Endocrinology & Metabolism, 2019, 104(10):4390-4397.

Okuyama et al., "Receptor Binding, Behavioral, and Electrophysiological Profiles of Nonpeptide Corticotropin-Releasing Factor Subtype 1 Receptor Antagonists CRA1000 and CRA1001," Journal of Pharmacology and Experimental Therapeutics, 1999, 289(2):926-935.

Oray et al., "Long-term effect of glucocorticoids," Expert Opinion on Drug Safety, 2016, 15(4):457-465.

Oster et al., "The functional and clinical significance of the 24-hour rhythm of circulating glucocorticoids," Endocrine Reviews, 2017, 38(1):3-45.

Overall et al., "The Brief Psychiatric Rating Scale (BPRS): recent developments in ascertainment and scaling," Psychopharmacology Bulletin, 1988, 24(1):97-99.

Overall et al., "The brief psychiatric rating scale," Psychological Reports, 1962, 10(3):799-812.

Overstreet et al., "Antidepressant-like effects of $CRF_1$ receptor antagonist SSR125543 in an animal model of depression," European Journal of Pharmacology, 2004, 497:49-53.

Owens et al., "Physiology and pharmacology of corticotropin-releasing factor," Pharmacol Rev., Dec. 1991, 43(4):425-473.

Pang et al., "Worldwide Experience in Newborn Screening for Classical Congenital Adrenal Hyperplasia due to 21-Hydroxylase Deficiency," Pediatrics, 1988, 81(6):866-874.

Pang S, et al., "Congenital adrenal hyperplasia due to 21-hydroxylase deficiency: newborn screening and its relationship to the diagnosis and treatment of the disorder," Screening, 1993, 2:105-139.

Pelleymounter MA, et al., "Role of Corticotropin-Releasing Factor (CRF) Receptors in the Anorexic Syndrome Induced by CRF," Journal of Pharmacology and Experimental Therapeutics, 2000, 293(3): 799-806.

Peplow et al., "Blood draws up to 3% of blood volume in clinical trials are safe in children," Acta Paediatrica, 2019, 108(5):940-944.

Perry SJ, et al., "Distinct Conformations of the Corticotropin Releasing Factor Type 1 Receptor Adopted following Agonist and Antagonist Binding Are Differentially Regulated," J. Biol. Chem., 2005, 280(12): 11560-11568.

Philbert et al., "The $CRF_1$ Receptor Antagonist SSR125543 Attenuates Long-Term Cognitive Deficit Induced by Acute Inescapable Stress in Mice, Independently From the Hypothalamic Pituitary Adrenal Axis," Pharmacology, Biochemistry, and Behavior, 2012, 10:415-422.

Philbert et al., "The CRF; Receptor Antagonist SSR125543 Prevents Stress-Induced Cognitive Deficit Associated With Hippocampal Dysfunction: Comparison With Paroxetine and D-cycloserine," Psychopharmacology, 2013, 228:97-107.

Purnell et al., "Association of 24-hour cortisol production rates, cortisol-binding globulin, and plasma-free cortisol levels with body composition, leptin levels, and aging in adult men and women," The Journal of Clinical Endocrinology & Metabolism, 2004, 89(1):281-287.

Ramos et al., "Drug-induced suppression of ACTH secretion does not promote anti-depressive or anxiolytic effects," Behavioral Brain Research, 2014, 265:69-75.

Ravens-Sieberer et al., "Feasibility, reliability, and validity of the EQ-5D-Y: results from a multinational study," Quality of Life Research, 2010, 19(6):887-897.

Reisch, "Substitution therapy in adult patients with congenital adrenal hyperplasia," Best Practice & Research Clinical Endocrinology & Metabolism, 2015, 29(1):33-45.

Rief et al., "Mechanisms involved in placebo and nocebo responses and implications for drug trials," Clinical Pharmacology & Therapeutics, 2011, 90(5):722-726.

Rivier CL, et al., "Role of Corticotropin-Releasing Factor Receptors Type 1 and 2 in Modulating the Rat Adrenocorticotropin Response to Stressors," Endocrinology, 2003, 144(6): 2396-2403.

Rivier JE, et al., "Constrained Corticotropin Releasing Factor Antagonists (Astressin Analogues) with Long Duration of Action in the Rat," J. Med. Chem. 1999, 42(16):3175-3182.

Rose & Hurst, "Plasma Cortisol and Growth Hormone Responses to Intravenous Catheterization," J Hum Stress., Mar. 1975, 1(1):22-36.

Ross et al., "Improved biochemical control with dose reduction in chronic glucocorticoid therapy: A phase III extension study of Chronocort (Efmody) in the treatment of Congenital Adrenal Hyperplasia (CAH)," Abstract submitted to Endo 2023 for consideration, prepared on Dec. 2022, 2 pages.

Ross et al., "Switching patients with Congenital Adrenal Hyperplasia to Modified release hydrocortisone capsules: relative bioavailability and disease control," Abstract submitted to European Congress of Endocrinology 2023 for consideration, prepared on Jan. 2023, 2 pages.

Sarafoglou et al., "Tildacerfont in adults with classic congenital adrenal hyperplasia: results from two phase 2 studies," Manuscript, The Journal of Clinical Endocrinology & Metabolism, 2021, 106(11):e4666-79.

Sarafoglou K, et al., "Impact of Hydrocortisone on Adult Height in Congenital Adrenal Hyperplasia—The Minnesota Cohort," J Pediatr., 2014, 164(5):1141-1146.

Science.nichd.nih.gov [Online], "Pediatric Endocrinology Training Program," 2020, [Retrieved on Mar. 6, 2023], retrieved from: URL<https://science.nichd.nih.gov/confluence/display/pe/Patient+Handouts+and+Support+Groups#PatientHandoutsandSupportGroups-CAHandAdrenalInsufficiency>, 3 pages.

Scott et al., "The use of the EQ-5D-Y health related quality of life outcome measure in children in the Western Cape, South Africa: psychometric properties, feasibility and usefulness—a longitudinal, analytical study," Health and Quality of Life Outcomes, 2017, 15:12.

Seymour et al., "The pharmacology of CP-154,526, a non-peptide antagonist of the CRH1 receptor: a review," CNS Drug Reviews, 2003, 9(1):57-96.

Shargel et al., "Multiple-Dosage Regiments," Applied Biopharmaceutics & Pharmacokinetics, 2012, 6th Edition, 31 pages.

Shargel et al., "Multiple-Dosage Regiments," Applied Biopharmaceutics & Pharmacokinetics, 2016, 7th Edition, 33 pages.

Silva IN, et al., "Randomised controlled trial of growth effect of hydrocortisone in congenital adrenal hyperplasia," Archives of Disease in Childhood, 1997, 77:214-218.

Smith et al., "Measures of sleep: the insomnia severity index, medical outcomes study (MOS) sleep scale, Pittsburgh sleep diary (PSD), and Pittsburgh sleep quality index (PSQI)," Arthritis Care & Research: Official Journal of the American College of Rheumatology, 2003, 49(S5):S184-S196.

(56) References Cited

OTHER PUBLICATIONS

Smith et al., "The role of the hypothalamic-pituitary-adrenal axis in neuroendocrine responses to stress," Dialogues Clin Neurosci., 2006, 8:383-395.
Soliman et al., "Congenital adrenal hyperplasia complicated by central precocious puberty: linear growth during infancy and treatment with gonadotropin-releasing hormone analog," Metabolism., May 1997, 46(5):513-517.
Somajni et al., "Neuropsychological assessment in prepubertal patients with congenital adrenal hyperplasia: preliminary study," Minerva Pediatr., Feb. 2011, 63(1):1-9.
Speiser et al., "Congenital adrenal hyperplasia due to steroid 21-hydroxylase deficiency: an Endocrine Society clinical practice guideline," J Clin Endocrinol Metab., Sep. 2010, 95(9):4133-60.
Speiser et al., "A Summary of the Endocrine Society Clinical Practice Guidelines on Congenital Adrenal Hyperplasia due to Steroid 21-Hydroxylase Deficiency," International Journal of Pediatric Endocrinology 2010, 2010:494173.
Speiser et al., "Congenital Adrenal Hyperplasia Due to Steroid 21-Hydroxylase Deficiency: An Endocrine Society Clinical Practice Guideline," J Clin Endocrinol Metab., 2018, 103(11):4043-4088.
Spierling et al., "Don't stress about CRF: assessing the translational failures of $CRF_1$ antagonists," Psychopharmacology, 2017, 234(9-10):1467-1481.
Steckler, "Developing small molecule nonpeptidergic drugs for the treatment of anxiety disorders: is the challenge still ahead?" Curr. Topics in Behav. Neurosciences, 2009, 415-428.
Stewart et al., "Development of a Biorelevant, Material-Sparing Membrane Flux Test for Rapid Screening of Bioavailability-Enhancing Drug Product Formulations," Mol Pharm., 2017, 14(6):2032-2046.
Stewart et al., "Exploring inpatient hospitalizations and morbidity in patients with adrenal insufficiency," The Journal of Clinical Endocrinology & Metabolism, 2016, 101(12):4843-4850.
Stikkelbroeck et al., "High prevalence of testicular adrenal rest tumors, impaired spermatogenesis, and Leydig cell failure in adolescent and adult males with congenital adrenal hyperplasia," J Clin Endocrinol Metab., Dec. 2001, 86(12):5721-5728.
Surget et al., "Corticolimbic transcriptome changes are state-dependent and region- specific in a rodent model of depression and of antidepressant reversal," Neuropsychopharmacology, 2009, 34:1363-1380.
Surget et al., "Drug-dependent requirement of hippocampal neurogenesis in a model of depression and of antidepressant reversal," Biol. Psychiatry, 2008, 64:293-301.
Teitelbaum, "Chronic peripheral administration of corticotropin-releasing factor causes colonic barrier dysfunction similar to psychological stress," Am J Physiol Gastrointest Liver Physiol, 2008, 295: G452-G459.
Tellew et al., "Discovery ofNBI-77860/GSK561679, a potent corticotropin-releasing factor ($CRF_1$) receptor antagonist with improved pharmacokinetic properties," Bioorganic & Medicinal Chemistry Letters, 2010, 20(24):7259-7264.
TheFreeDictionary.com, "Baseline," available on or before Nov. 7, 2016, via Internet Archive: Wayback Machine URL <https://web.archive.org/web/20161107132345/http:/medical-dictionary.thefreedictionary.com/baseline>, 3 pages.
Therrell BL, et al., "Newborn Screening for Congenital Adrenal Hyperplasia," Endocrinol Metab Clin North Am., 2001, 30(1):15-30.
Trakakis et al., "An update to 21-hydroxylase deficient congenital adrenal hyperplasia," Gynecol Endocrinol., Jan. 2010, 26(1):63-71.
Trapp CM, et al. "Recommendations for Treatment of Nonclassic Congenital Adrenal Hyperplasia (NCCAH): an Update," Steroids, 2012, 77(4):342-346.
Trapp et al., "Congenital adrenal hyperplasia: an update in children," Curr Opin Endocrinol Diabetes Obes., 2011, 18(3):166-170.
Turcu et al., "Novel treatment strategies in congenital adrenal hyperplasia," Curr Opin Endocrinol Diabetes Obes., 2016, 23(3):225-232.
Turcu et al., "Single-Dose Study of a Corticotropin-Releasing Factor Receptor-1 Antagonist in Women With 21-Hydroxylase Deficiency," J Clin Endocrinol Metab., Mar. 2016, 101(3):1174-1180.
Turcu et al., "The Next 150 Years of Congenital Adrenal Hyperplasia," J Steroid Biochem Mol Biol., Sep. 2015, 153:63-71.
Urani et al., "The Corticotropin-Releasing Factor 1 Receptor Antagonist, SSR125543, and the Vasopressin 1b Receptor Antagonist, SSR149415, Prevent Stress-Induced Cognitive Impairment in Mice," Pharmacology, Biochemistry, and Behavior, 2011, 98:425-431.
U.S. Appl. No. 62/545,406, Howerton et al., "Corticotropin Releasing Factor Receptor Antagonists," filed Aug. 14, 2017, 65 pages.
Vale et al., "Chemical and biological characterization of corticotropin releasing factor," Recent Prog Horm Res., 1983, 39:245-270.
Vale et al., "Characterization of a 41-Residue Ovine Hypothalamic Peptide That Stimulates Secretion of Corticotropin and β-Endorphin," Science, 1981, 213:1394-1397.
Varni et al., "PedsQL™ 4.0: Reliability and validity of the Pediatric Quality of Life Inventory™ Version 4.0 Generic Core Scales in healthy and patient populations," Medical Care, 2001, 39(8):800-812.
Varni et al., "The PedsQL™ 4.0 as a school population health measure: feasibility, reliability, and validity," Quality of Life Research, 2006, 15:203-215.
Varni et al., "The PedsQL™ family impact module: preliminary reliability and validity," Health and Quality of Life Outcomes, 2004, 2:55.
Vickers et al., "Why Use Placebos in Clinical Trials? A Narrative Review of the Methodological Literature," Journal of Clinical Epidemiology, 2000, 53(2):157-161.
Vijayan et al., "Metabolic profile, cardiovascular risk factors and health-related quality of life in children, adolescents and young adults with congenital adrenal hyperplasia," 2019, 32(8):871-877.
Vokl TMK, et al., "Adrenarche and Puberty in Children with Classic Congenital Adrenal Hyperplasia due to 21-Hydroxylase Deficiency," Horm Res Paediatr., 2011, 76(6):400-410.
Vokl TMK, et al., "Obesity Among Children and Adolescents with Classic Congenital Adrenal Hyperplasia due to 21-Hydroxylase Deficiency." Pediatrics, 2006, 117(1):e98-e105.
Webb et al., "Current and Novel Approaches to Children and Young People with Congenital Adrenal Hyperplasia and Adrenal Insufficiency," Best Pract Res Clin Endocrinol Metab., 2015, 29:449-468.
Webb TR, et al., "Synthesis of benzoylpyrimidines as antagonists of the corticotropin-releasing factor-1 receptor," Bioorganic & Medicinal Chemistry Letters, 2004, 14(15): 3869-3873.
Webster et al., "In Vivo and In Vitro Characterization of Antalarmin, a Nonpeptide Corticotropin-Releasing Hormone (CRH) Receptor Antagonist: Suppression of Pituitary ACTH Release and Peripheral Inflammation," Endocrinology, Jan. 1, 1996, 137(12):5747-5750.
White PC, et al., "Congenital Adrenal Hyperplasia due to 21-Hydroxylase Deficiency," Endocr Rev., 2000, 21(3):245-291.
White PC, et al., "Optimizing Newborn Screening for Congenital Adrenal Hyperplasia," J. Pediatr., 2013, 163:10-12.
Whitten JP, et al., "Rapid Microscale Synthesis, a New Method for Lead Optimization Using Robotics and Solution Phase Chemistry: Application to the Synthesis and Optimization of Corticotropin-Releasing Factor1 Receptor Antagonists," J. Med. Chem., 1996, 39(22): 4354-4357.
Wiens, "A fixed sequence Bonferroni procedure for testing multiple endpoints," Pharmaceutical Statistics: The Journal of Applied Statistics in the Pharmaceutical Industry, 2003, 2(3):211-215.
Wilcoxen K, et al., "Synthesis of 3-phenylpyrazolo[4,3-b]pyridines via a convenient synthesis of 4-amino-3-arylpyrazoles and SAR of corticotropin-Releasing factor receptor type-1 antagonists," Bioorganic & Medicinal Chemistry Letters, 2003, 13(19): 3367-3370.
Williams, "Corticotropin-releasing factor 1 receptor antagonists: a patent review," Expert Opin. Ther. Patents, 2013, 23(8):1057-1068.
Witchel et al., "Congenital Adrenal Hyperplasia," J. Pediatr. Adolesc. Gynecol., 2011, 24:116-126.
Witchel et al., "Congenital Adrenal Hyperplasia," J. Pediatr. Adolesc. Gynecol., 2017, 30(5):520-534.

(56) References Cited

OTHER PUBLICATIONS

Wong et al., "Increased hepatobiliary clearance of unconjugated thyroxine determines DMP 904-induced alterations in thyroid hormone homeostasis in rats," Toxicological Sciences, 2005, 84(2):232-242.

Wood S, et al., "Depressive and cardiovascular disease comorbidity in a rat model of social stress: a putative role for corticotropin-releasing factor," Psychopharmacology, 2012, 222(2): 325-336.

Wustrow DJ, et al., "Pyrazolo[1,5-a]pyrimidine CRF-1 receptor antagonists," Bioorganic & Medicinal Chemistry Letters, 1998, 8(16): 2067-2070.

Yuan J, et al., "3-Aryl pyrazolo[4,3-d]pyrimidine derivatives: nonpeptide CRF-1 antagonists," Bioorganic & Medicinal Chemistry Letters, 2002, 12(16): 2133-2136.

Zhu et al., "Synthesis and mode of action of $^{125}$I-and $^{3}$H-labeled thieno [2,3-c]pyridine antagonists of cell adhesion molecule expression," The Journal of Organic Chemistry, 2002, 67(3):943-948.

Zorrilla et al., "Behavioral, biological, and chemical perspectives on targetilig CRF(1) receptor antagonists to treat alcoholism," Drug and Alcohol Dependence, (2013), 128(3):175-186.

Zorrilla et al., "The therapeutic potential of CRF1 antagonists for anxiety," Expert Opin. Investig. Drugs, 2004, 13(7):799-828.

Zorrilla, "Progress in corticotropin-releasing factor-1 antagonist development," Drug Discov Today, 2010, 15:371-383.

Zoumakis et al., "Corticotropin-releasing hormone receptor antagonists," European Journal of Endocrinology, 2006, 155(1):S85-S91.

Zoumakis et al., "Corticotropin-releasing hormone receptor antagonists: an update," Pediatric Neuroendocrinology Endocr Dev., 2010, 17:36-43.

[No Author Listed], "Search Results for CAS No. 121548-04-7," American Chemical Society CAS SciFinder, search performed on Apr. 7, 2025 at www.cas.org, 2 pages.

Accessdata.fda.gov [online], "FDA, Center for Drug Evaluation and Research, 218808Orig1s000, 218820Orig1s000, Product Quality Review(S)," Oct. 7, 2024, retrieved on Apr. 10, 2025, retrieved from URL <https://www.accessdata.fda.gov/drugsatfda_docs/nda/2025/218808Orig1s000,21882 0Orig1s000ChemR.pdf>, 90 pages.

Claahsen-van der Grinten et al., "Challenges in Adolescent and Adult Males With Classic Congenital Adrenal Hyperplasia Due to 21-Hydroxylase Deficiency," J Clinical Endocrinology & Metabolism, Feb. 2025, 110 (Supplement_1):S25-36.

Do Thi et al., "Formulate-ability of ten compounds with different physicochemical profiles in SMEDDS," European journal of pharmaceutical sciences, Dec. 8, 2009, 38(5):479-88.

Eitel et al., "Barriers to the Management of Classic Congenital Adrenal Hyperplasia Due to 21-Hydroxylase Deficiency," J Clinical Endocrinology & Metabolism, Feb. 2025, 110 (Supplement 1):S67-73.

Engberg et al., "Clinical Manifestations and Challenges in Adolescent and Adult Females With Classic Congenital Adrenal Hyperplasia Due to 21-Hydroxylase Deficiency," J Clinical Endocrinology & Metabolism, Feb. 2025, 110 (Supplement 1):S37-45.

Foster, "Deuterium isotope effects in the metabolism of drugs and xenobiotics: implications for drug design," Advances in Drug Research, 1985, 14:1-40.

Gattefosse.com [online], "Gelucire® 44/14," available on or before Nov. 30, 2023 via Internet Archive: Wayback Machine URL<https://web.archive.org/web/20231130013520/https://www.gattefosse.com/pha rmaceuticals/product-finder/gelucire-4414>, retrieved on Apr. 10, 2025, retrieved from URL <https://www.gattefosse.com/pharmaceuticals/product-finder/gelucire-4414>, 6 pages.

Gattefosse.com [online], "Labrafac™MLipophile WL 1349," available on or before Nov. 30, 2023 via Internet Archive: Wayback Machine URL<https://web.archive.org/web/20231130120205/https://www.gattefosse.com/pharmaceuticals/product-finder/labrafac-lipophile-wl-1349>, retrieved on Apr. 10, 2025, retrieved from URL <https://www.gattefosse.com/pharmaceuticals/product-finder/labrafac-lipophile-wl-1349>, 6 pages.

Gattefosse.com [online], "LabrafacTMPG," available on or before Nov. 30, 2023 via Internet Archive: Wayback Machine URL<https://web.archive.org/web/20231130184227/https://www.gattefosse.com/pharmaceuticals/product-finder/labrafac-pg>, retrieved on Apr. 10, 2025, retrieved from URL <https://www.gattefosse.com/pharmaceuticals/product-finder/labrafac-pg>, 5 pages.

Kushner et al., "Pharmacological uses and perspectives of heavy water and deuterated compounds," Canadian journal of physiology and pharmacology, Feb. 1, 1999, 77(2):79-88.

Nokoff et al., "Clinical Manifestations and Treatment Challenges in Infants and Children With Classic Congenital Adrenal Hyperplasia Due to 21-Hydroxylase Deficiency," J Clinical Endocrinology & Metabolism, Feb. 2025, 110(Supplement_1):S13-24.

Online.Uspnf.com [online], "Medium-Chain Triglycerides," Nov. 1, 2020, retrieved on Mar. 26, 2025, retrieved from URL <https://online.uspnf.com/uspnf/document/1_GUID-995A5AEA-A8B8-473A-BE2C-94DA0912145B_5_en-US?source=Activity>, 4 pages.

Online.Uspnf.com [online], "Propylene Glycol Dicaprylate/Dicaprate," May 1, 2020, retrieved on Mar. 27, 2025, retrieved from URL <https://online.uspnf.com/uspnf/document/1_GUID-8CD288A0-4573-4B12-9F29-87144943C326 2 en-us?source=Search Results &highlight=Pro . . . >, 2 pages.

Peter, "Congenital adrenal hyperplasia: 11ß-hydroxylase deficiency," Seminars in reproductive medicine, Aug. 2002, 20(3):249-254, abstract.

Pouton, "Lipid formulations for oral administration of drugs: non-emulsifying, self-emulsifying and 'self-microemulsifying' drug delivery systems," European journal of pharmaceutical sciences, Oct. 1, 2000, 11:S93-8.

Sandberg et al., "Mental Health Issues Associated With Classic Congenital Adrenal Hyperplasia Due to 21-Hydroxylase Deficiency," J Clinical Endocrinology & Metabolism, Feb. 2025, 110 (Supplement_1):S46-55.

Sarafoglou et al., "Future Directions in the Management of Classic Congenital Adrenal Hyperplasia Due to 21-Hydroxylase Deficiency," J Clinical Endocrinology & Metabolism, Feb. 2025, 110 (Supplement_1):S74-87.

Sarafoglou et al., "Phase 3 Trial of Crinecerfont in Pediatric Congenital Adrenal Hyperplasia," New England Journal of Medicine, Jun. 2, 2024, 1-11.

Spernath et al., "Microemulsions as carriers for drugs and nutraceuticals," Advances in colloid and interface science, Dec. 21, 2006, 128:47-64.

Wikipedia.org [online], "Medium-chain triglyceride," last updated on Dec. 28, 2024, retrieved on Apr. 10, 2025, retrieved from URL<https://en.wikipedia.org/w/index.php?title=Medium-chain_triglyceride&oldid=1265809727>, 4 pages.

Wikipedia.org [online], "Molecular mass," last updated on Nov. 2, 2024, retrieved on Apr. 10, 2025, retrieved from URL<https://en.wikipedia.org/w/index.php?title=Molecular_mass&oldid=125499668 5>, 4 pages.

Witchel et al., "Life With Classic Congenital Adrenal Hyperplasia Due to 21-Hydroxylase Deficiency: Challenges and Burdens," J Clinical Endocrinology & Metabolism, Feb. 2025, 110 (Supplement_1):S56-66.

Yang et al., "Genetics and Pathophysiology of Classic Congenital Adrenal Hyperplasia Due to 21-Hydroxylase Deficiency," J Clinical Endocrinology & Metabolism, Feb. 2025, 110 (Supplement_1):S1-2.

CRF RECEPTOR ANTAGONISTS AND METHODS OF USE

CROSS-REFERENCE TO RELATED APPLICATIONS

This application is a National Stage Application under 35 U.S.C. § 371 and claims the benefit of International Application No. PCT/US2020/052851, filed Sep. 25, 2020, which claims priority to U.S. Provisional Application No. 62/906,967, filed Sep. 27, 2019. The disclosures of the foregoing applications are hereby incorporated by reference in their entireties.

BACKGROUND

Technical Field

This disclosure relates generally to compounds, compositions and methods related thereto such as methods for treating congenital adrenal hyperplasia (CAH).

Description of the Related Technology

CRF is a hypothalamic hormone that acts as the key regulator of the hypothalamic-pituitary—adrenal (HPA) axis. Classic congenital adrenal hyperplasia (CAH) is a disease that includes a group of autosomal recessive disorders that result in an enzyme deficiency that alters the production of adrenal steroids due to 21-hydroxylase enzyme deficiency, a condition that results in little or no cortisol biosynthesis. One clinical manifestation of the absence of cortisol is the lack of feedback inhibition of CRF which causes dysregulation of the HPA axis. Also, the 21-hydroxylase enzyme deficiency causes a shunting of cortisol precursor steroids leading to excess androgen (e.g., 17-hydroxyprogesterone, androstenedione, and testosterone) production.

Currently, exogenous corticosteroids are the standard of care for treating patients with classic CAH. This treatment is used to correct the cortisol deficiency and reduce androgen excess. However, the dose of corticosteroid used is typically well above the normal physiological level used for cortisol replacement alone (as in patients with Addison's disease). This increased exposure to corticosteroids can lead to iatrogenic Cushing's syndrome, increased cardiovascular risk factors, glucose intolerance, reduced growth velocity, and decreased bone mineral density in CAH patients. Thus, there is a need for a treatment for CAH that avoids the severe complications associated with current corticosteroid therapy.

It has been demonstrated in clinical trials that certain $CRF_1$ antagonist compounds provide significant reduction in CAH-relevant steroid biomarkers (e.g., 17-hydroxyprogesterone and androstenedione) compared to placebo in patients with CAH.

There remains a need to identify new $CRF_1$ antagonists for use in the treatment of CAH. The present disclosure fulfills these and other needs, as evident in reference to the following disclosure.

SUMMARY

Provided herein are compounds that are CRF antagonists. In particular embodiments, compounds are provided that are $CRF_1$ antagonists. Also, provided herein are compounds that are prodrugs of compounds that are CRF antagonists. Accordingly, such compounds and prodrugs are useful in the treatment of CAH.

Some embodiments provide a pharmaceutical composition comprising a compound of formula (Ia):

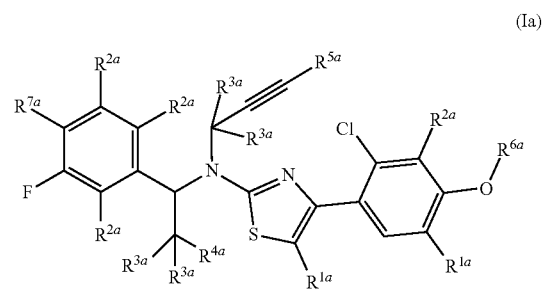

(Ia)

or a pharmaceutically acceptable salt thereof and at least one pharmaceutically acceptable excipient, wherein:
each $R^{1a}$ is independently $C(R^A)_3$ or $C(R^A)_2R^B$;
each $R^A$ is independently hydrogen or deuterium;
$R^B$ is $-OR^C$;
$R^C$ is hydrogen or deuterium;
each $R^{2a}$ is independently hydrogen or deuterium;
each $R^{3a}$ is independently hydrogen or deuterium;
$R^{4a}$ is

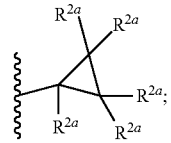

$R^{5a}$ is hydrogen or deuterium;
$R^{6a}$ is $C(R^A)_3$; and
$R^{7a}$ is $C(R^A)_3$ or $C(R^A)_2R^B$,
wherein at least one of $R^{1a}$ and $R^{7a}$ is $C(R^A)_2R^B$.

Some embodiments provide a preparation of a compound of formula (Ia):

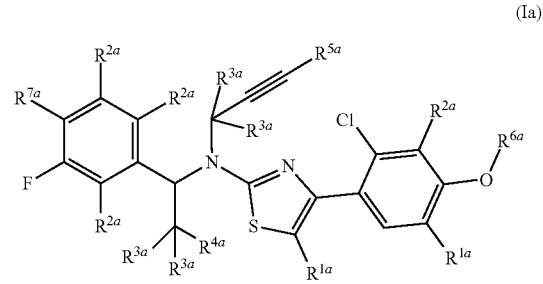

(Ia)

or a pharmaceutically acceptable salt thereof, wherein:
each $R^{1a}$ is independently $C(R^A)_3$ or $C(R^A)_2R^B$;
each $R^A$ is independently hydrogen or deuterium;
$R^B$ is $-OR^C$;
$R^C$ is hydrogen or deuterium;
each $R^{2a}$ is independently hydrogen or deuterium;
each $R^{3a}$ is independently hydrogen or deuterium;

$R^{4a}$ is

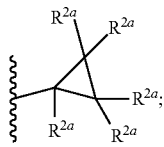

$R^{5a}$ is hydrogen or deuterium;
$R^{6a}$ is $C(R^A)_3$; and
$R^{7a}$ is $C(R^A)_3$ or $C(R^A)_2R^B$,
wherein at least one of $R^{1a}$ and $R^{7a}$ is $C(R^A)_2R^B$.

In some embodiments, the compound of formula (Ia) is a compound of formula:

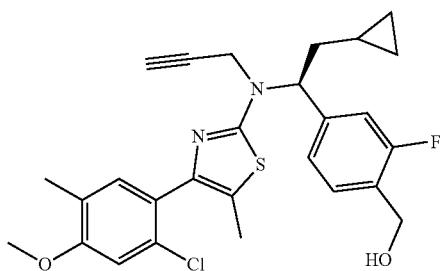 [SMILES: C#CCN(c1nc(-c2cc(C)c(OC)cc2Cl)c(C)s1)[C@@H](CC1CC1)c1ccc(CO)c(F)c1]

or a pharmaceutically acceptable salt thereof.

Some embodiments provide a method of treating congenital adrenal hyperplasia in a subject in need thereof comprising administering a compound of formula (Ia), or a pharmaceutically acceptable salt thereof.

Some embodiments provide a method of treating congenital adrenal hyperplasia in a subject in need thereof comprising administering a compound of formula (Ia), or a pharmaceutically acceptable salt thereof, in an amount sufficient to reduce the level of one or more biomarker(s) selected from (a) 17-hydroxyprogesterone (17-OHP); (b) testosterone; and (c) androstenedione in the subject.

In some embodiments the method comprises administering the compound of formula (Ia), or a pharmaceutically acceptable salt thereof, in an amount sufficient to reduce the level of one or more biomarker(s) selected from (a) 17-hydroxyprogesterone (17-OHP); (b) testosterone; and (c) androstenedione in the subject.

Some embodiments provide a method for reducing the severity of one or more symptoms selected from hirsutism, precocious puberty, fertility problems, acne, and growth impairment in a subject having classic congenital adrenal hyperplasia, comprising administering a compound of formula (Ia), or a pharmaceutically acceptable salt thereof in an amount sufficient to reduce the level of androstenedione in the subject.

Some embodiments provide a method of reducing the level of one or more biomarker(s) in a subject having congenital adrenal hyperplasia comprising administering to the subject a compound of formula (Ia), or a pharmaceutically acceptable salt thereof.

Some embodiments provide a method of reducing the dosage of corticosteroid administered to a subject having congenital adrenal hyperplasia for controlling congenital adrenal hyperplasia comprising administering to the subject a compound of formula (Ia), or a pharmaceutically acceptable salt thereof.

Some embodiments provide a method of reducing the severity of one or more side effects of glucocorticoid treatment in a subject having congenital adrenal hyperplasia comprising administering to the subject a compound of formula (Ia), or a pharmaceutically acceptable salt thereof, wherein the side effect is selected from osteoporosis, avascular necrosis of bone, myopathy, hyperglycemia, diabetes mellitus, dyslipidemia, weight gain, Cushing syndrome, Cushingoid features, growth suppression, adrenal suppression, gastritis, peptic ulcer, gastrointestinal bleeding, visceral perforation, hepatic steatosis, pancreatitis, hypertension, coronary heart disease, ischemic heart disease, heart failure, dermatoprosis, skin atrophy, ecchymosis, purpura, erosions, striae, delayed wound healing, easy bruising, acne, hirsutism, hair loss, mood changes, depression, euphoria, mood lability, irritability, akathisia, anxiety, cognitive impairment, psychosis, dementia, delirium, cataract, glaucoma, ptosis, mydriasis, opportunistic ocular infections, central serous chorioretinopathy, suppression of cell-mediated immunity, predisposition to infections, reactivation of latent infections.

Some embodiments provide a compound of formula (I):

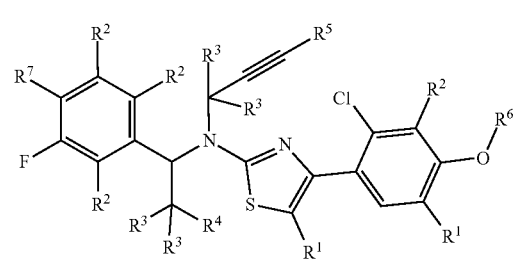

(I)

or a pharmaceutically acceptable salt thereof, wherein:
each $R^1$ is independently $C(R^A)_3$ or $C(R^A)_2R^B$;
each $R^A$ is independently hydrogen or deuterium;
B is —$OR^C$;
$R^C$ is hydrogen or deuterium;
each $R^2$ is independently hydrogen or deuterium;
each $R^3$ is independently hydrogen or deuterium;
$R^4$ is

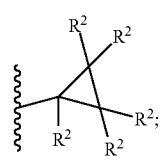

$R^5$ is hydrogen or deuterium;
$R^6$ is $C(R^A)_3$; and
$R^7$ is $C(R^A)_3$ or $C(R^A)_2R^B$,
wherein at least one of $R^A$, $R^2$, $R^3$ and $R^5$ is deuterium, and at least one of $R^1$ and $R^7$ is $C(R^A)_2R^B$.

Some embodiments provide a compound of formula (III):

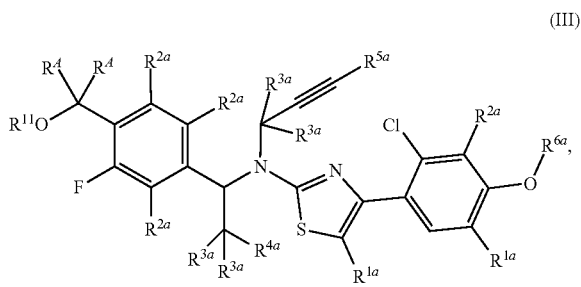

(III)

or a pharmaceutically acceptable salt thereof, wherein:
R$^{11}$ is a) —P(=O)(OR$^{33}$)$_2$ or —P(=O)(OR$^{33}$)(N(R$^{33}$)$_2$);
b) —(=O)R$^{50}$;
c) —C(=O)N(R$^{33}$)R$^{50}$;
d) —C(=O)OR$^{50}$; or
e) R$^{50}$;
each R$^{33}$ is independently hydrogen, C$_1$-C$_6$alkyl, haloC$_1$-C$_6$alkyl or aryl, wherein the C$_1$-C$_6$alkyl and aryl are each optionally substituted with R$^{10}$;
R$^{50}$ is C$_1$-C$_6$alkyl, C$_3$-C$_7$cycloalkyl, C$_3$-C$_7$ cycloalkenyl, C$_2$-C$_6$ alkenyl, C$_2$-C$_6$alkynyl, aryl, heteroaryl, or heterocyclyl, each of which is optionally substituted with one or more R$^{10}$ and/or R$^{20}$;
each R$^{10}$ is independently halo, haloC$_1$-C$_6$alkyl, cyano, nitro, trimethylsilanyl, —O. (oxyl radical), —OR$^{30}$, —SR$^{30}$, —OC(O)—R$^{30}$, —OC(O)O—R$^{30}$, —N(R$^{30}$)$_2$, —C(O)R$^{30}$, —C(O)OR$^{30}$, —OC(O)N(R$^{30}$)$_2$, —C(O)N(R$^{30}$)$_2$, —N(R$^{30}$)C(O)OR$^{31}$, —N(R$^{30}$)C(O)R$^{31}$, —N(R$^{30}$)C(=NR$^{31}$)N(R$^{32}$)$_2$, —N(R$^{30}$)S(O)$_t$R$^{31}$, —S(O)$_t$OR$^{30}$, —S(O)$_p$R$^{30}$, —S(O)$_t$N(R$^{30}$)$_2$, —OP(=O)(OR$^{30}$)$_2$, or optionally two R$^{10}$ groups taken together on a single atom form oxo;
each t is independently 1 or 2;
each p is independently 1, 2 or 3;
each R$^{20}$ is independently C$_1$-C$_6$alkyl, C$_2$-C$_6$ alkenyl, aryl, C$_3$-C$_7$cycloalkyl, C$_3$-C$_7$ cycloalkenyl, heterocyclyl, or heteroaryl, wherein each R$^{20}$ is optionally substituted with R$^{10}$ and/or R$^{22}$;
each R$^{22}$ is independently C$_1$-C$_6$alkyl, C$_2$-C$_6$ alkenyl, aryl, C$_3$-C$_7$cycloalkyl, C$_3$-C$_7$ cycloalkenyl, heterocyclyl, or heteroaryl, wherein each R$^{22}$ is optionally substituted with R$^{10}$; and
each R$^{30}$, R$^{31}$ and R$^{32}$ is independently hydrogen, haloC$_1$-C$_6$alkyl, or C$_1$-C$_6$alkyl;
each R$^{1a}$ is independently C(R$^A$)$_3$;
each R$^A$ is independently hydrogen or deuterium;
each R$^{2a}$ is independently hydrogen or deuterium;
each R$^{3a}$ is independently hydrogen or deuterium;
R$^{4a}$ is

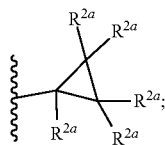

R$^{5a}$ is hydrogen or deuterium; and R$^{6a}$ is C(R$^A$)$_3$.
Some embodiments provide a pharmaceutical composition comprising a compound of formula (I), or formula (III), or a pharmaceutically acceptable salt thereof; and at least one pharmaceutically acceptable excipient.

Some embodiments provide a method of treating congenital adrenal hyperplasia in a subject in need thereof comprising administering to the subject a therapeutically effective amount of a compound of formula (I), or formula (III), or a pharmaceutically acceptable salt thereof.

Some embodiments provide a method of treating congenital adrenal hyperplasia in a subject in need thereof comprising administering to the subject a therapeutically effective amount of (S)-{4-[1-{[4-(2-chloro-4-methoxy-5-methylphenyl)-5-methyl-1,3-thiazol-2-yl](prop-2-yn-1-yl)amino}-2-cyclopropylethyl]-2-fluorophenyl}methanol (Compound 2), wherein Compound 2 is generated under physiological conditions or by solvolysis following administration to the subject of a prodrug of Compound 2, or a pharmaceutically acceptable salt thereof, wherein the prodrug of Compound 2, or the pharmaceutically acceptable salt thereof, is not 4-(2-chloro-4-methoxy-5-methylphenyl)-N-((1S)-2-cyclopropyl-1-(3-fluoro-4-methylphenyl)ethyl)-5-methyl-N-2-propyn-1-yl-2-thiazolamine, or a pharmaceutically salt thereof.

Some embodiments provide a method of treating congenital adrenal hyperplasia in a subject in need thereof comprising administering to the subject a therapeutically effective amount of (S)-{4-[1-{[4-(2-chloro-4-methoxy-5-methylphenyl)-5-methyl-1,3-thiazol-2-yl](prop-2-yn-1-yl)amino}-2-cyclopropylethyl]-2-fluorophenyl}methanol (Compound 2), wherein Compound 2 is generated as a result of a metabolic chemical reaction following administration to the subject of a prodrug of Compound 2, or a pharmaceutically acceptable salt thereof, wherein the prodrug of Compound 2, of the pharmaceutically acceptable salt thereof, is not 4-(2-chloro-4-methoxy-5-methylphenyl)-N-((1S)-2-cyclopropyl-1-(3-fluoro-4-methylphenyl)ethyl)-5-methyl-N-2-propyn-1-yl-2-thiazolamine, or a pharmaceutically salt thereof.

Some embodiments provide a method of treating congenital adrenal hyperplasia in a subject in need thereof comprising administering to the subject a therapeutically effective amount of a prodrug of (S)-{4-[1-{[4-(2-chloro-4-methoxy-5-methylphenyl)-5-methyl-1,3-thiazol-2-yl](prop-2-yn-1-yl)amino}-2-cyclopropylethyl]-2-fluorophenyl}methanol (Compound 2), or a pharmaceutically acceptable salt thereof, wherein the prodrug of Compound 2, or the pharmaceutically acceptable salt thereof, is not 4-(2-chloro-4-methoxy-5-methylphenyl)-N-((1S)-2-cyclopropyl-1-(3-fluoro-4-methylphenyl)ethyl)-5-methyl-N-2-propyn-1-yl-2-thiazolamine, or a pharmaceutically salt thereof.

These and other embodiments will be apparent upon reference to the following detailed description. To this end, various references are set forth herein that describe in more detail certain background information, procedures, compounds and compositions, and are each hereby incorporated by reference in their entirety.

DETAILED DESCRIPTION

Compounds

Provided herein are compounds useful for treating diseases and/or disorders treatable by modulating CRF$_1$.

The present invention provides a compound of formula (I):

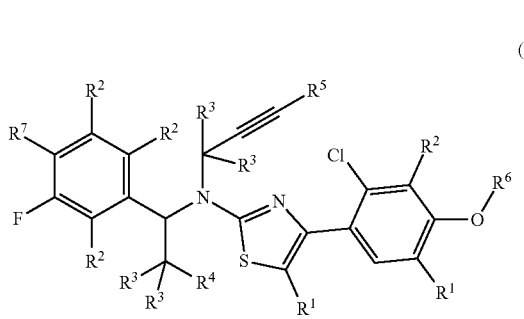

or a pharmaceutically acceptable salt thereof, wherein:
each $R^1$ is independently $C(R^A)_3$ or $C(R^A)_2R^B$;
each $R^A$ is independently hydrogen or deuterium;
$R^B$ is —$OR^C$;
$R^C$ is hydrogen or deuterium;
each $R^2$ is independently hydrogen or deuterium;
each $R^3$ is independently hydrogen or deuterium;
$R^4$ is

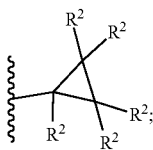

$R^5$ is hydrogen or deuterium;
$R^6$ is $^{13}C(R^A)_3$ or $C(R^A)_3$; and
$R^7$ is $C(R^A)_3$ or $C(R^A)_2R^B$,
wherein at least one of $R^A$, $R^2$, $R^3$ and $R^5$ is deuterium, and at least one of $R^1$ and $R^7$ is $C(R^A)_2R^B$.

In some embodiments, the present invention provides a compound of formula (I):

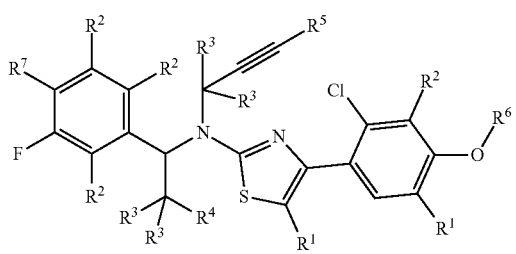

or a pharmaceutically acceptable salt thereof, wherein:
each $R^3$ is independently $C(R^A)_3$ or $C(R^A)_2R^B$;
each $R^A$ is independently hydrogen or deuterium;
$R^B$ is —$OR^C$;
$R^C$ is hydrogen or deuterium;
each $R^2$ is independently hydrogen or deuterium;
each $R^3$ is independently hydrogen or deuterium;

$R^4$ is

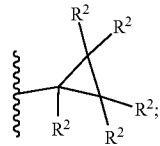

$R^5$ is hydrogen or deuterium;
$R^6$ is $C(R^A)_3$; and
$R^7$ is $C(R^A)_3$ or $C(R^A)_2R^B$,
wherein at least one of $R^A$, $R^2$, $R^3$ and $R^5$ is deuterium, and at least one of $R^1$ and $R^7$ is $C(R^A)_2R^B$.

In some embodiments, $R^6$ is $^{13}CD_3$.
In some embodiments, $R^6$ is $CD_3$; and $R^7$ is $CH_3$.
In some embodiments, $R^6$ is $CH_3$; and $R^7$ is $CD_3$.
In some embodiments, $R^6$ is $CD_3$; and $R^7$ is $CD_3$.
In some embodiments, $R^1$ is $CD_3$.
In some embodiments, each $R^A$ is hydrogen.
In some embodiments, each $R^2$ is hydrogen.
In some embodiments, each $R^3$ is hydrogen.
In some embodiments, the present invention relates to a compound of formula (Ia):

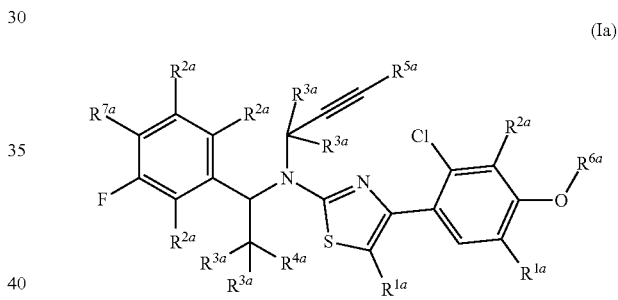

or a pharmaceutically acceptable salt thereof, wherein:
each $R^{1a}$ is independently $C(R^A)_3$ or $C(R^A)_2R^B$;
each $R^A$ is independently hydrogen or deuterium;
$R^B$ is —$OR^C$;
$R^C$ is hydrogen or deuterium;
each $R^{3a}$ is independently hydrogen or deuterium;
each $R^{4a}$ is independently hydrogen or deuterium;
$R^{4a}$ is

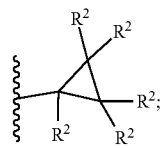

$R^{5a}$ is hydrogen or deuterium;
$R^{6a}$ is $^{13}C(R^A)_3$ or $C(R^A)_3$; and
$R^{7a}$ is $C(R^A)_3$ or $C(R^A)_2R^B$,
wherein at least one of $R^{1a}$ and $R^{7a}$ is $C(R^A)_2R^B$.

In some embodiments, the present invention relates to a compound of formula (Ia):

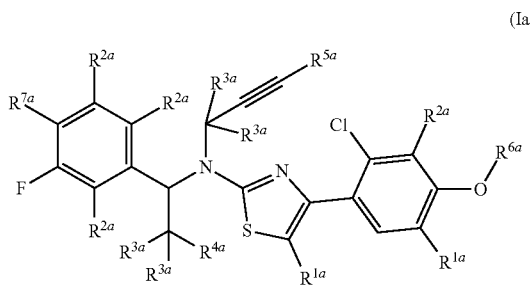

(Ia)

or a pharmaceutically acceptable salt thereof, wherein:
each $R^{1a}$ is independently $C(R^A)_3$ or $C(R^A)_2R^B$;
each $R^A$ is independently hydrogen or deuterium;
$R^B$ is —$OR^C$;
$R^C$ is hydrogen or deuterium;
each $R^{2a}$ is independently hydrogen or deuterium;
each $R^{3a}$ is independently hydrogen or deuterium;
$R^{4a}$ is

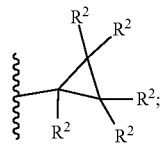

$R^{5a}$ is hydrogen or deuterium;
$R^{6a}$ is $C(R^A)_3$; and
$R^{7a}$ is $C(R^A)_3$ or $C(R^A)_2R^B$,
wherein at least one of $R^{1a}$ and $R^{7a}$ is $C(R^A)_2R^B$.

In some embodiments, $R^{7a}$ is $C(R^A)_2R^B$; and $R^C$ is hydrogen.

In some embodiments, $R^{7a}$ is $CH_2OH$.

In some embodiments, the present invention relates to a compound formula (IIa):

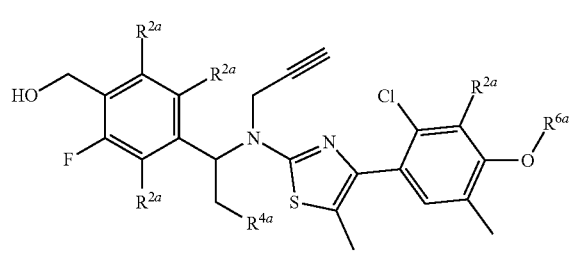

(IIa)

or a pharmaceutically acceptable salt thereof.

In some embodiments, $R^{6a}$ $CD_3$ or $R^{6a}$ is $CH_3$.

In some embodiments, $R^{6a}$ is $CD_3$.

In some embodiments, each $R^{2a}$ is hydrogen.

In some embodiments, $R^{7a}$ is $CD_2OH$.

In some embodiments, the present invention provides a compound having the formula:

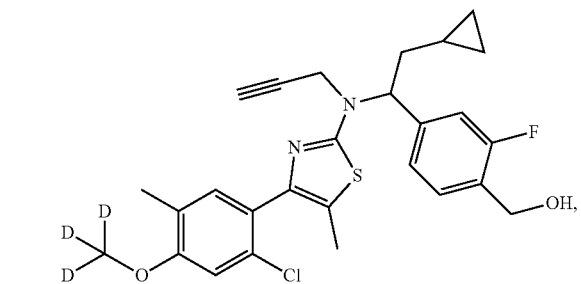 [SMILES: [2H]C([2H])([2H])Oc1cc(Cl)c(-c2nc(N(CC#C)C(CC3CC3)c3ccc(CO)c(F)c3)sc2C)cc1C]

or a pharmaceutically acceptable salt thereof.

In some embodiments, the present invention provides a compound having the following formula:

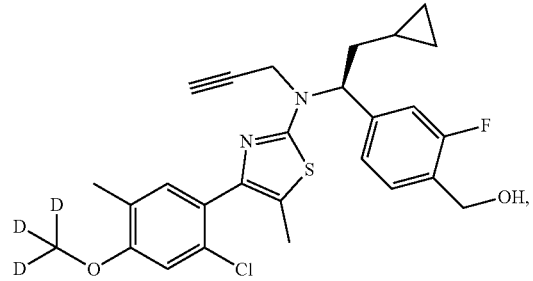 [SMILES: [2H]C([2H])([2H])Oc1cc(Cl)c(-c2nc(N(CC#C)[C@@H](CC3CC3)c3ccc(CO)c(F)c3)sc2C)cc1C]

or a pharmaceutically acceptable salt thereof.

In some embodiments, the present invention relates to a compound having the following formula:

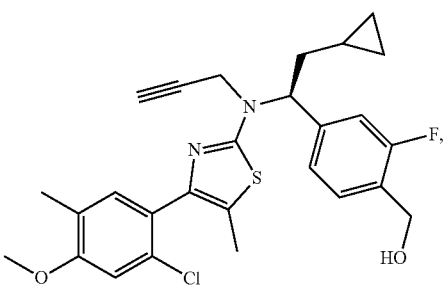 [SMILES: C#CCN(c1nc(-c2cc(C)c(OC)cc2Cl)c(C)s1)[C@@H](CC1CC1)c1ccc(CO)c(F)c1]

or a pharmaceutically acceptable salt thereof.

It is further appreciated that certain features, which are, for clarity, described in the context of separate embodiments, can also be provided in combination in a single embodiment. Conversely, various features which are, for brevity, described in the context of a single embodiment, can also be provided separately or in any suitable subcombination.

The compounds described herein can be asymmetric (e.g., having one or more stereocenters). All stereoisomers, such as enantiomers and diastereomers, are intended unless otherwise indicated. It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, a racemic mixture, diastereomerically pure, diastereomerically enriched, or a stereoisomeric mixture. Preparation of enantiomerically pure or enantiomerically enriched forms may be accomplished by resolution of racemic mixtures or by using enantiomerically pure or enriched starting materials or by stereoselective or stereospecific synthesis. Stereochemical definitions are available in E. L. Eliel, S. H. Wilen & L. N. Mander "Stereochemistry of Organic Compounds" John Wiley & Sons, Inc., New York, NY, 1994 which is incorporated herein by reference in its entirety. In some embodiments, where the compound of the invention is chiral or otherwise includes one or more stereocenters, the compound can be prepared with an enantiomeric excess (ee) or diastereomeric excess (de) of greater than about 75%, greater than about 80%, greater than about 85%, greater than about 90%, greater than about 95%, or greater than about 99%. As will be apparent by the context a compound of the invention can refer to a single molecule or a plurality of molecules.

Resolution of racemic mixtures of compounds can be carried out by any of numerous methods known in the art. An example method includes fractional recrystallization using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids. Other resolving agents suitable for fractional crystallization methods include stereoisomerically pure forms of methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

In some embodiments, a compound of the invention can be prepared having at least about 5%, at least about 10%, at least about 20%, at least about 30%, at least about 40%, at least about 50%, at least about 60%, at least about 70%, at least about 80%, at least about 90%, at least about 95%, at least about 99%, or at least about 99.9% enantiomeric excess, or an enantiomeric excess within a range defined by any of the preceding numbers.

The compounds described herein also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone—enol pairs, amide-imidic acid pairs, lactam-lactim pairs, enamine—imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

The compounds described herein, and their pharmaceutically acceptable salts, can be found together with other substances such as water and solvents, for example, in the form of hydrates or solvates. When in the solid state, the compounds described herein and salts thereof may occur in various forms and may, e.g., take the form of solvates, including hydrates. The compounds may be in any solid state form, such as a crystalline form, amorphous form, solvated form, etc., so unless clearly indicated otherwise, reference in the specification to compounds and salts thereof should be understood as reading on any solid state form of the compound.

As used herein, the term "solvate" refers to a solid form of a compound of the present invention (or a pharmaceutically acceptable salt thereof), which includes one or more molecules of a solvent in stoichiometric or non-stoichiometric amount. Where the solvent is water, the solvate is a hydrate.

In some embodiments, the compounds described herein, or salts thereof, are substantially isolated. By "substantially isolated" is meant that the compound is at least partially or substantially separated from the environment in which it was formed or detected. Partial separation can include, for example, a composition enriched in the compounds of the invention. Substantial separation can include compositions containing at least about 50%, at least about 60%, at least about 70%, at least about 80%, at least about 90%, at least about 95%, at least about 97%, or at least about 99% by weight of the compounds disclosed herein, or salt thereof.

As used herein, "about" means ±20% of the stated value, and includes more specifically values of ±10%, ±5%, ±2% and ±1% of the stated value.

In addition, it is understood that, when the compounds described herein contain one or more double bond(s) (e.g., C=C, C=N, and the like) or other centers of geometric asymmetry, and unless specified otherwise, it is intended that the compounds include both E and Z geometric isomers (e.g., cis or trans). Cis and trans geometric isomers of the compounds described herein may be isolated as a mixture of isomers or as separated isomeric forms.

Isotopes

The compounds disclosed and described herein allow atoms at each position of the compound independently to have an isotopic distribution for a chemical element in proportional amounts to those usually found in nature or an isotopic distribution in proportional amounts different to those usually found in nature unless the context clearly dictates otherwise. A particular chemical element has an atomic number defined by the number of protons within the atom's nucleus. Each atomic number identifies a specific element, but not the isotope; an atom of a given element may have a wide range in its number of neutrons. The number of both protons and neutrons in the nucleus is the atom's mass number, and each isotope of a given element has a different mass number. A compound wherein one or more atoms have an isotopic distribution for a chemical element in proportional amounts different to those usually found in nature is commonly referred to as being an isotopically-labeled compound. Each chemical element as represented in a compound structure may include any isotopic distribution of said element. For example, in a compound structure a hydrogen atom may be explicitly disclosed or understood to be present in the compound. At any position of the compound that a hydrogen atom may be present, the hydrogen atom can be an isotopic distribution of hydrogen, including but not limited to protium ($^1$H) and deuterium ($^2$H) in proportional amounts to those usually found in nature and in proportional amounts different to those usually found in nature. Thus, reference herein to a compound encompasses all potential isotopic distributions for each atom unless the context clearly dictates otherwise. Examples of isotopes include isotopes of hydrogen, carbon, nitrogen, oxygen, phosphorous, sulfur, fluorine, chlorine, bromine and iodine. As one of skill in the art would appreciate, any of the compounds as disclosed and described herein may include radioactive isotopes. Accordingly, also contemplated is use of compounds as disclosed and described herein, wherein one or more atoms have an isotopic distribution different to those usually found in nature, such as having $^2$H or $^3$H in greater proportion, or $^{11}$C, $^{13}$C, or $^{14}$C in greater proportion than found in nature. By way of general example, and without limitation, isotopes of hydrogen include protium ($^1$H), deuterium ($^2$H) and tritium ($^3$H). Isotopes of carbon include carbon-11 ($^{11}$C), carbon-12 ($^{12}$C), carbon-13 ($^{13}$C), and carbon-14 ($^{14}$C). Isotopes of nitrogen include nitrogen-13 ($^{13}$N), nitrogen-14 ($^{14}$N) and nitrogen-15 ($^{15}$N). Isotopes of oxygen include oxygen-14 ($^{14}$O), oxygen-15 ($^{15}$O), oxygen-16 ($^{16}$O) oxygen-17 ($^{17}$O), and oxygen-18 ($^{18}$O). Isotope of fluorine include fluorine-17 ($^{17}$F), fluorine-18 ($^{18}$F) and fluorine-19 ($^{19}$F). Isotopes of phosphorous include phosphorus-31 ($^{31}$P), phosphorus-32 ($^{32}$P), phosphorus-33 ($^{33}$P), phosphorus-34 ($^{34}$P), phosphorus-35 ($^{35}$P) and phosphorus-36 ($^{36}$P). Isotopes of sulfur include sulfur-32 ($^{32}$S), sulfur-33 ($^{33}$S), sulfur-34 ($^{34}$S), sulfur-35 ($^{35}$S), sulfur-36 ($^{36}$S) and sulfur-38 ($^{38}$S). Isotopes of chlorine include chlorine-35 ($^{35}$Cl), chlorine-36 ($^{36}$Cl) and chlorine-37 ($^{37}$Cl). Isotopes of bromine include bromine-75 ($^{75}$Br), bromine-76 ($^{76}$Br), bromine-77 ($^{77}$Br), bromine-79 ($^{79}$Br), bromine-81 ($^{81}$Br) and bromine-82 ($^{82}$Br). Isotopes of iodine include iodine-123 ($^{123}$I) iodine-124 ($^{124}$I) iodine-125 ($^{125}$I) iodine-131 ($^{131}$I) and iodine-135 ($^{135}$I). In some embodiments, atoms at every position of the compound have an isotopic distribution for each chemical element in proportional amounts to those usually found in nature. In some embodiments, atoms at least one position of the compound has an isotopic distribution for a chemical element in proportional amounts different to those usually found in nature (remainder atoms having an isotopic distribution for a chemical element in proportional amounts to those usually found in nature). In some embodiments, atoms at least two positions of the compound independently have an isotopic distribution for a chemical element in proportional amounts different to those usually found in nature (remainder atoms having an isotopic distribution for a chemical element in proportional amounts to those usually found in nature). In some embodiments, atoms in at least three positions of the compound independently have an isotopic distribution for a chemical element in proportional amounts different to those usually found in nature (remainder atoms having an isotopic distribution for a chemical element in proportional amounts to those usually found in nature). In some embodiments, atoms in at least four positions of the compound independently have an isotopic distribution for a chemical element in proportional amounts different to those usually found in nature (remainder atoms having an isotopic distribution for a chemical element in proportional amounts to those usually found in nature). In some embodiments, atoms in at least five positions of the compound independently have an isotopic distribution for a chemical element in proportional amounts different to those usually found in nature (remainder atoms having an isotopic distribution for a chemical element in proportional amounts to those usually found in nature). In some embodiments, atoms in at least six positions of the compound independently have an isotopic distribution for a chemical element in proportional amounts different to those usually found in nature (remainder atoms having an isotopic distribution for a chemical element in proportional amounts to those usually found in nature). As will be apparent by the context a compound of the invention can refer to a single molecule or a plurality of molecules.

Certain compounds, for example those having radioactive isotopes such as $^3$H and $^{14}$C incorporated, are also useful in drug or substrate tissue distribution assays. Tritium ($^3$H) and carbon-14 ($^{14}$C) isotopes are particularly preferred for their ease of preparation and detectability. Compounds with isotopes such as deuterium ($^2$H) in proportional amounts greater than is usually found in nature may afford certain therapeutic advantages resulting from greater metabolic stability, such as, for example, increased in vivo half-life or reduced dosage requirements. Isotopically-labeled compounds can generally be prepared by performing procedures routinely practiced in the art. Methods are readily available to measure such isotope perturbations or enrichments, such as, mass spectrometry, and for isotopes that are radioisotopes additional methods are available, such as, radio-detectors used in connection with HPLC or GC.

As used herein, "isotopic variant" means a compound that contains an unnatural proportion of an isotope at one or more of the atoms that constitute such a compound. In certain embodiments, an "isotopic variant" of a compound contains unnatural proportions of one or more isotopes, including, but not limited to, protium ($^1$H), deuterium ($^2$H), tritium ($^3$H), carbon-11 ($^{11}$C), carbon-12 ($^{12}$C), carbon-13 ($^{13}$C), carbon-14 ($^{14}$C), nitrogen-13 ($^{13}$N), nitrogen-14 ($^{14}$N), nitrogen-15 ($^{15}$N), oxygen-14 ($^{14}$O), oxygen-15 ($^{15}$O), oxygen-16 ($^{16}$O), oxygen-17 ($^{17}$O), oxygen-18 ($^{18}$O) fluorine-17 ($^{17}$F), fluorine-18 ($^{18}$F), phosphorus-31 ($^{31}$P), phosphorus-32 ($^{32}$P), phosphorus-33 ($^{33}$P), sulfur-32 ($^{32}$S), sulfur-33 ($^{33}$S), sulfur-34 ($^{34}$S), sulfur-35 ($^{35}$S), sulfur-36 ($^{36}$S), chlorine-35 ($^{35}$Cl), chlorine-36 ($^{36}$Cl), chlorine-37 ($^{37}$Cl), bromine-79 ($^{79}$Br), bromine-81 ($^{81}$Br), iodine-123 ($^{123}$I) iodine-125 ($^{125}$I) iodine-127 ($^{127}$I), iodine-129 ($^{129}$I) and iodine-131 ($^{131}$I). In certain embodiments, an "isotopic variant" of a compound is in a stable form, that is, non-radioactive. In certain embodiments, an "isotopic variant" of a compound contains unnatural proportions of one or more isotopes, including, but not limited to, hydrogen ($^1$H), deuterium ($^2$H), carbon-12 ($^{12}$C), carbon-13 ($^{13}$C), nitrogen-14 ($^{13}$N), nitrogen-15 ($^{15}$N), oxygen-16 ($^{16}$O), oxygen-17 ($^{17}$O), and oxygen-18 ($^{18}$O). In certain embodiments, an "isotopic variant" of a compound is in an unstable form, that is, radioactive. In certain embodiments, an "isotopic variant" of a compound contains unnatural proportions of one or more isotopes, including, but not limited to, tritium ($^3$H), carbon-11 ($^{11}$C), carbon-14 ($^{14}$C), nitrogen-13 ($^{13}$N), oxygen-14 ($^{14}$O), and oxygen-15 ($^{15}$O). It will be understood that, in a compound as provided herein, any hydrogen can include $^2$H as the major isotopic form, as example, or any carbon include be $^{13}$C as the major isotopic form, as example, or any nitrogen can include $^{15}$N as the major isotopic form, as example, and any oxygen can include $^{18}$O as the major isotopic form, as example. In certain embodiments, an "isotopic variant" of a compound contains an unnatural proportion of deuterium ($^2$H).

With regard to the compounds provided herein, when a particular atomic position is designated as having deuterium or "D" or "d", it is understood that the abundance of deuterium at that position is substantially greater than the natural abundance of deuterium, which is about 0.015%. A position designated as having deuterium typically has a minimum isotopic enrichment factor of, in certain embodiments, at least 3500 (52.5% deuterium incorporation), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation) at each designated deuterium position.

Synthetic methods for incorporating radio-isotopes into organic compounds are applicable to compounds of the invention and are well known in the art. These synthetic methods, for example, incorporating activity levels of tritium into target molecules, are as follows:

A. Catalytic Reduction with Tritium Gas: This procedure normally yields high specific activity products and requires halogenated or unsaturated precursors.
B. Reduction with Sodium Borohydride [$^3$H]: This procedure is rather inexpensive and requires precursors containing reducible functional groups such as aldehydes, ketones, lactones, esters and the like.
C. Reduction with Lithium Aluminum Hydride [$^3$H]: This procedure offers products at almost theoretical specific activities. It also requires precursors containing reducible functional groups such as aldehydes, ketones, lactones, esters and the like.
D. Tritium Gas Exposure Labeling: This procedure involves exposing precursors containing exchangeable protons to tritium gas in the presence of a suitable catalyst.
E. N-Methylation using Methyl Iodide [$^3$H]: This procedure is usually employed to prepare O-methyl or N-methyl ($^3$H) products by treating appropriate precursors with high specific activity methyl iodide ($^3$H). This method in general allows for higher specific activity, such as for example, about 70-90 Ci/mmol.

Synthetic methods for incorporating activity levels of $^{12}$I into target molecules include:

A. Sandmeyer and like reactions: This procedure transforms an aryl amine or a heteroaryl amine into a diazonium salt, such as a diazonium tetrafluoroborate salt and subsequently to $^{125}$I labeled compound using Na$^{125}$I. A representative procedure was reported by Zhu, G-D. and co-workers in J. Org. Chem., 2002, 67, 943-948.
B. Ortho $^{125}$Iodination of phenols: This procedure allows for the incorporation of $^{125}$I at the ortho position of a phenol as reported by Collier, T. L. and co-workers in J. Labelled Compd. Radiopharm, 1999, 42, S264-S266.
C. Aryl and heteroaryl bromide exchange with $^{125}$I: This method is generally a two step process. The first step is the conversion of the aryl or heteroaryl bromide to the corresponding tri-alkyltin intermediate using for example, a Pd catalyzed reaction [i.e. Pd(Ph$_3$P)$_4$] or through an aryl or heteroaryl lithium, in the presence of a tri-alkyltinhalide or hexaalkylditin [e.g., (CH$_3$)$_3$SnSn (CH$_3$)$_3$]. A representative procedure was reported by Le Bas, M. D. and co-workers in J. Labelled Compd. Radiopharm. 2001, 44, S280-S282.

Chemical Definitions

Unless defined otherwise, all technical and scientific terms used herein have the same meaning as is commonly understood by one of ordinary skill in the art to which this disclosure belongs. All patents, applications, published applications, and other publications are incorporated by reference in their entirety. In the event that there is a plurality of definitions for a term herein, those in this section prevail unless stated otherwise.

Whenever a group is described as being "optionally substituted" that group can be unsubstituted, or can be substituted with one or more of the indicated substituents. Likewise, when a group is described as being "unsubstituted or substituted" if substituted, the substituent(s) can be selected from one or more of the indicated substituents. It is to be understood that substitution at a given atom is limited by valency.

As used herein, "$C_a$-$C_b$" in which "a" and "b" are integers refer to the number of carbon atoms in an alkyl, alkenyl, or alkynyl group, or the number of carbon atoms in the ring of a heterocyclyl, heteroaryl, cycloalkyl, cycloalkenyl, or aryl group. That is, these groups can contain from "a" to "b", inclusive, carbon atoms. Thus, for example, a "$C_1$-$C_4$ alkyl" group refers to all alkyl groups having from 1 to 4 carbons, that is, CH$_3$—, CH$_3$CH$_2$—, CH$_3$CH$_2$CH$_2$—, (CH$_3$)$_2$CH—, CH$_3$CH$_2$CH$_2$CH$_2$—, CH$_3$CH$_2$CH(CH$_3$)— and (CH$_3$)$_3$C—. If no "a" and "b" are designated with regard to an alkyl, alkenyl, alkynyl, heterocyclyl, heteroaryl, cycloalkyl, cycloalkenyl, or aryl group, the broadest range described in these definitions is to be assumed.

In addition to the foregoing, as used in the specification and appended claims, unless specified to the contrary, the following terms have the meaning indicated:

The term "alkenyl" refers to an alkyl group that contains in the straight or branched hydrocarbon chain one or more double bonds. Examples of alkenyl groups include allenyl, vinylmethyl, and ethenyl. In some embodiments, an alkenyl group can be unsubstituted or substituted. In some embodiments, the alkenyl group can have 2 to 6 carbon atoms. The alkenyl group of the compounds can be designated as "$C_2$-$C_6$ alkenyl" or similar designations.

The term "alkynyl" refers to an alkyl group that contains in the straight or branched hydrocarbon chain one or more triple bonds. Examples of alkynyls include ethynyl and propynyl. An alkynyl group can be unsubstituted or substituted. In some embodiments, an alkynyl group can be unsubstituted or substituted. In some embodiments, the alkynyl group can have 2 to 6 carbon atoms. The alkenyl group of the compounds can be designated as "$C_2$-$C_6$ alkynyl" or similar designations.

The term "aryl" refers to an aromatic ring system containing 6, 10 or 14 carbon atoms that can contain a single ring, two fused rings or three fused rings, such as phenyl, naphthalenyl and phenanthrenyl. In some embodiments, the aryl group can have 6 or 10 carbon atoms (i.e., $C_6$ or $C_{10}$ aryl). When one or more substituents are present on the "aryl" ring, the substituent(s) can be bonded at any available ring carbon. In some embodiments, an aryl group can be substituted or unsubstituted. In some embodiments, the aryl group is phenyl.

The term "alkyl" refers to a fully saturated straight or branched hydrocarbon radical. The alkyl group can have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms. In some embodiments, the alkyl group can have 1 to 6 carbons (i.e., "$C_1$-$C_6$ alkyl"). Some embodiments are 1 to 5 carbons (i.e., $C_1$-$C_5$ alkyl), some embodiments are 1 to 4 carbons (i.e., $C_1$-$C_4$ alkyl), some embodiments are 1 to 3 carbons (i.e., $C_1$-$C_3$ alkyl), and some embodiments are 1 or 2 carbons. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl, and t-butyl. Examples of an alkyl group include: methyl, ethyl, n-propyl, isopropyl, n-butyl, sec-butyl, isobutyl, tert-butyl, pentyl, isopentyl, tert-pentyl, neo-pentyl, 1-methylbutyl [i.e., —CH(CH$_3$)CH$_2$CH$_2$CH$_3$], 2-methylbutyl [i.e., —CH$_2$CH(CH$_3$)CH$_2$CH$_3$], n-hexyl and the like. When one or more substituents are present on the alkyl group, the substituent(s) can be bonded at any available carbon atom. In some embodiments, an alkyl group can be substituted or unsubstituted.

The term "haloalkyl" refers to an alkyl group, as defined herein, wherein one or more hydrogen atoms of the alkyl group have been replaced by a halogen atom (e.g., monohaloalkyl, di-haloalkyl, and tri-haloalkyl). In some embodiments, the haloalkyl group can have 1 to 6 carbons (i.e., "halo$C_1$-$C_6$ alkyl"). The halo$C_1$-$C_6$ alkyl can be fully substituted in which case it can be represented by the formula $C_nL_{2n+1}$, wherein L is a halogen and "n" is 1, 2, 3, 4, 5, or 6. When more than one halogen is present then they can be the same or different and selected from: fluorine, chlorine, bromine, and iodine. In some embodiments, haloalkyl contains 1 to 5 carbons (i.e., halo$C_1$-$C_5$ alkyl). In some embodiments, haloalkyl contains 1 to 4 carbons (i.e., halo$C_1$-$C_4$ alkyl). In some embodiments, haloalkyl contains 1 to 3 carbons (i.e., halo$C_1$-$C_3$ alkyl). In some embodiments, haloalkyl contains 1 or 2 carbons. Examples of haloalkyl groups include fluoromethyl, difluoromethyl, trifluoromethyl, chlorodifluoromethyl, 1-fluoroethyl, 2,2,2-trifluoroethyl, pentafluoroethyl, 4,4,4-trifluorobutyl, and the like.

The term "carbonyl" refers to the group —C(=O)—.

The term "oxo" refers to the =O substituent.

The term "oxyl" refers to a —O· group (oxyl radical).

The term "cycloalkyl" refers to a fully saturated all carbon mono- or multi-cyclic ring system. In some embodiments, the cycloalkyl is a monocyclic ring containing 3 to 7 carbon atoms (i.e., "$C_3$-$C_7$ cycloalkyl"). Some embodiments contain 3 to 6 carbons. Some embodiments contain 3 to 5 carbons. Some embodiments contain 5 to 7 carbons. Some embodiments contain 3 to 4 carbons. Examples include cyclopropyl, cyclobutyl, cyclopentyl, and cyclohexyl. When one or more substituents are present on the alkyl group, the substituent(s) can be bonded at any available carbon atom. In some embodiments, a cycloalkyl group can be substituted or unsubstituted.

The term "cycloalkenyl" refers to a mono- or multi-cyclic hydrocarbon ring system that contains one or more double bonds in at least one ring; although, if there is more than one, the double bonds cannot form a fully delocalized pi-electron system throughout all the rings (i.e., an aromatic system), otherwise the group would be "aryl," as defined herein. When composed of two or more rings, the rings can be connected together in a fused, bridged, or spiro fashion. A cycloalkenyl can contain 3 to 12 atoms in the ring(s) or 3 to 8 atoms in the ring(s). In some embodiments, a cycloalkenyl group can be unsubstituted or substituted. In some embodiments, the cycloalkenyl group may have 4 to 8 carbon atoms (i.e., "$C_4$-$C_8$ cycloalkenyl"). An example is cyclohexenyl.

The term "heteroaryl" refers to an monocyclic or fused multicyclic aromatic ring system and having at least one heteroatom in the ring system, that is, an element other than carbon, including but not limited to, nitrogen, oxygen and sulfur. Some embodiments are "5-6 membered heteroaryl" and refers to an aromatic ring containing 5 to 6 ring atoms in a single ring and having at least one heteroatom in the ring system. Examples of heteroaryl rings include, but are not limited to, pyridyl, pyrimidinyl, pyrazinyl, pyridazinyl, triazinyl, furyl, quinolyl, isoquinolyl, thienyl, imidazolyl, thiazolyl, indolyl, isoindolyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, dibenzo[b,d]furan, dibenzo[b,d]thiophene, phenanthridinyl, benzimidazolyl, pyrrolyl, quinolinyl, isoquinolinyl, benzisoxazolyl, imidazo[1,2-b]thiazolyl, and the like. A heteroaryl group can be substituted or unsubstituted. In some embodiments, the heteroaryl group has 5 to 10 ring members or 5 to 7 ring members. The heteroaryl group can be designated as "5-7 membered heteroaryl," "5-10 membered heteroaryl," or similar designations. In some embodiments, the heteroaryl can be a substituted or unsubstituted $C_1$-$C_{13}$ five-, six-, seven, eight-, nine-, ten-, up to 14-membered monocyclic, bicyclic, or tricyclic ring system including 1 to 5 heteroatoms selected from nitrogen, oxygen and sulfur. In some embodiments, the heteroaryl can be a substituted or unsubstituted $C_1$-$C_5$ five- or six-membered monocyclic ring including 1 to 5 heteroatoms selected from nitrogen, oxygen and sulfur. In some embodiments, the heteroaryl can be a substituted or unsubstituted $C_5$-$C_9$ eight-, nine- or ten-membered bicyclic ring system including 1 to 5 heteroatoms selected from nitrogen, oxygen and sulfur. In some embodiments, the heteroaryl is a substituted or unsubstituted $C_5$-$C_9$ eight-, nine- or ten-membered heteroaryl. In some embodiments, the $C_5$-$C_9$ eight-, nine- or ten-membered bicyclic heteroaryl is imidazo[2,1-b]thiazolyl, 1H-indolyl, isoindolyl, benzofuranyl, benzothienyl, benzimidazolyl, benzisoxazolyl, indazolyl, purinyl, quinolinyl, isoquinolinyl, quinoxalinyl, pyrido[3,4-b]pyrazinyl or pyrido[4,3-d]pyrimidinyl. In some embodiments, the heteroaryl is a substituted or unsubstituted $C_8$-$C_{13}$ 13- or 14-membered tricyclic ring system including 1 to 5 heteroatoms selected from nitrogen, oxygen and sulfur. In some embodiments, the heteroaryl can be an azolyl such as imidazolyl, pyrazolyl, 1,2,3-triazolyl, 1,2,4-triazolyl, tetrazolyl, 1,2,4-thiadiazolyl, thiazolyl, isothiazolyl, oxazolyl, or isoxazolyl, each of which can be substituted or unsubstituted. In some embodiments, the heteroaryl is a $C_1$-$C_4$ 5-membered heteroaryl. In some embodiments, the $C_1$-$C_4$ 5-membered heteroaryl is furanyl, thienyl, 1,2,4-thiadiazolyl, 1,2,3-thiadiazolyl, isothiazolyl, thiazolyl, imidazolyl, pyrazolyl, isoxazolyl, oxazolyl, pyrrolyl, triazolyl, tetrazolyl. In some embodiments, the heteroaryl is a $C_3$-$C_5$ 6-membered heteroaryl. In some embodiments, the $C_3$-$C_5$ 6-membered heteroaryl is pyridinyl, pyrimidinyl, pyrazinyl, pyridazinyl, or triazinyl. In some embodiments, "5-10 membered heteroaryl" refers to: furanyl, thienyl, pyrrolyl, imidazolyl, oxazolyl, thiazolyl, isoxazolyl, pyrazolyl, isothiazolyl, oxadiazolyl, triazolyl, tetrazolyl, thiadiazolyl, pyridinyl, pyrazinyl, pyrimidinyl, pyridazinyl, quinoxalinyl, triazinyl, benzofuranyl, 1H-indolyl, benzo[b]thiophenyl, and the like. In some embodiments, "5-10 membered heteroaryl" refers to: pyrazinyl, pyridazinyl, pyridinyl, pyrimidinyl, 1H-indolyl, quinoxalinyl, thiadiazolyl, and the like. In some embodiments, a heteroaryl group can be substituted or unsubstituted.

The term "heterocyclyl" refers to a three-, four-, five-, six-, seven-, eight-, nine-, ten-, up to 18-membered monocyclic, bicyclic, and tricyclic ring system wherein carbon atoms together with from 1 to 5 heteroatoms constitute said ring system and optionally containing one or more unsaturated bonds situated in such a way, however, that a fully delocalized pi-electron system (aromatic system) does not occur in the monocyclic ring or in at least one ring of the bicyclic or tricyclic ring system. The heteroatom(s) is an element other than carbon including, but not limited to, oxygen, sulfur, and nitrogen. When composed of two or more rings, the rings can be joined together in a fused, bridged, or spiro fashion where the heteroatom(s) can be present in either a non-aromatic or aromatic ring in the ring system. In some embodiments, the heterocyclyl can be a 3-7 membered saturated non-aromatic ring system containing 3 to 7 ring atoms, where at least one ring atom is a heteroatom. In some embodiments, "3-6 membered heterocyclyl" refers to a saturated non-aromatic ring radical containing 3 to 6 ring atoms, where at least one ring atom is a heteroatom. In some embodiments, "4-6 membered heterocyclyl" refers to a saturated non-aromatic ring radical containing 4 to 6 ring atoms, where at least one ring atom is a heteroatom. In some embodiments, the one or two heteroatoms in the ring system are selected independently from: O (oxygen) and N (nitrogen). In some embodiments, a heterocyclyl can include a carbonyl (C=O) group adjacent to a hetero atom, that is, be substituted with an oxo on a carbon adjacent to a hetero atom, where the substituted ring system is a lactam, lactone, cyclic imide, cyclic thioimide or cyclic carbamate. Examples of unsubstituted or oxo substituted "heterocyclyl" groups include but are not limited to, aziridinyl, azetidinyl, tetrahydrofuranyl, 1,3-dioxinyl, 1,3-dioxanyl, 1,4-dioxanyl, 1,2-dioxolanyl, 1,3-dioxolanyl, 1,4-dioxolanyl, 1,3-oxathianyl, 1,4-oxathiinyl, 1,3-oxathiolanyl, 1,3-dithiolyl, 1,3-dithiolanyl, 1,4-oxathianyl, tetrahydro-1,4-thiazinyl, 2H-1,2-oxazinyl, maleimidyl, succinimidyl, dioxopiperazinyl, hydantoinyl, imidazolinyl, imidazolidinyl, isoxazolinyl, isoxazolidinyl, isoindolinyl, indolinyl, oxazolinyl, oxazolidinyl, oxazolidinonyl, thiazolinyl, thiazolidinyl, morpholinyl, oxiranyl, piperidinyl N-oxide, piperidinyl, piperazinyl, pyrrolidinyl, pyrrolidonyl, pyrrolidinonyl, 4-piperidonyl, pyrazolinyl, pyrazolidinyl, 2-oxopyrrolidinyl, tetrahydropyranyl, 4H-pyranyl, tetrahydrothiopyranyl, 1,4-diazabicyclo [2.2.2]octane, 1,4-diazabicyclo[3.1.1]heptane, 2-azaspiro[3,3]heptane, 2,6-diazaspiro[3,3]heptane, 2-oxa-6-azaspiro[3,3]heptane, and their benzo-fused analogs (e.g., benzimidazolidinonyl, tetrahydroquinolinyl, and 3,4-methylenedioxyphenyl). The heterocyclyl group can be designated as "3-10 membered heterocyclyl" or similar designations. In some embodiments, the heterocyclyl can be a $C_2$-$C_{12}$ three-, four-, five-, six-, seven-, eight-, nine-, ten-, up to 13-membered monocyclic, bicyclic, or tricyclic ring system including 1 to 5 heteroatoms selected from nitrogen, oxygen and sulfur. In some embodiments, the heterocyclyl can be a substituted or unsubstituted $C_2$-$C_6$ three-, four-, five-, six-, or seven-membered monocyclic ring including 1 to 5 heteroatoms selected from nitrogen, oxygen and sulfur. In some embodiments, the heterocyclyl can be a substituted or unsubstituted $C_2$-$C_{10}$ four-, five-, six-, seven-, eight-, nine-, ten- or eleven-membered bicyclic ring system including 1 to 5 heteroatoms selected from nitrogen, oxygen and sulfur. In some embodiments, the heterocyclyl can be a substituted or unsubstituted $C_7$-$C_{12}$ 12- or 13-membered tricyclic ring system including 1 to 5 heteroatoms selected from nitrogen, oxygen and sulfur. In some embodiments, the heteroatom(s) of six membered monocyclic heterocyclyls are selected from one up to three of O (oxygen), N (nitrogen) or S (sulfur), and the heteroatom(s) of five membered monocyclic heterocyclyls are selected from one or two heteroatoms selected from O (oxygen), N (nitrogen) or S (sulfur). In some embodiments, the heterocyclyl can be aziridinyl, azetidinyl, tetrahydrofuranyl, 1,3-dioxinyl, 1,3-dioxanyl, 1,4-dioxanyl, 1,2-dioxolanyl, 1,3-dioxolanyl, 1,3-oxathianyl, 1,4-oxathianyl, 1,3-oxathiolanyl, 1,3-dithiolyl, 1,3-dithiolanyl, 1,4-oxathianyl, tetrahydro-1,4-thiazinyl, imidazolinyl, imidazolidinyl, isoxazolinyl, isoxazolidinyl, isoindolinyl, indolinyl, oxazolinyl, oxazolidinyl, thiazolinyl, thiazolidinyl, morpholinyl, oxiranyl, piperidinyl, piperazinyl, pyrrolidinyl, pyrazolinyl, pyrazolidinyl, tetrahydropyranyl, tetrahydrothiopyranyl, 1,4-diazabicyclo[2.2.2]octane, 1,4-diazabicyclo[3.1.1]heptane, 2-azaspiro[3,3]heptane, 2,6-diazaspiro[3,3]heptane, tetrahydroquinolinyl, 1,2,3,4-tetrahydroisoquinolinyl, 1,2,3,4-tetrahydro-2,6-naphthyridinyl, 1,2,3,4-tetrahydro-2,7-naphthyridinyl, 1,2,3,4-tetrahydro-1,7-naphthyridinyl, 1,2,3,4-tetrahydro-1,6-naphthyridinyl, 5,6,7,8-tetrahydropyrido[2,3-d]pyrimidinyl, 5,6,7,8-tetrahydropyrido[3,4-d]pyrimidinyl, [1,3]dioxolo[4, 5-c]pyridinyl, [1,3]dioxolo[4,5-b]pyridinyl, [1,3]dioxolo[4, 5-d]pyrimidinyl or 3,4-methylenedioxyphenyl. In some embodiments, the unsubstituted or substituted heterocyclyl can be selected from aziridinyl, azetidinyl, piperidinyl, morpholinyl, oxetanyl, piperazinyl, pyrrolidinyl, thiomorpholinyl, 2-piperidone, 1,1-dioxidothiomorpholinyl, oxolanyl (tetrahydrofuranyl), and oxanyl (tetrahydropyranyl). When one or more substituents are present on the heterocyclyl group, the substituent(s) can be bonded at any available carbon atom and/or heteroatom. In some embodiments, a heterocyclyl group can be substituted or unsubstituted.

The term "cyano" refers to the group —CN.

The term "halogen" or "halo" refers to a fluoro, chloro, bromo, or iodo group. In some embodiments, halogen or halo is fluoro, chloro, or bromo. In some embodiments, halogen or halo is fluoro or chloro. In some embodiments, halogen or halo is fluoro.

The term "nitro" refers to a —$NO_2$ group.

The term "halogenating agent" refers to a compound that contributes a halogen atom to a reactant compound such as converting an alcohol reactant compound to an alkyl halide product compound. Examples of halogenating agents include, but are not limited to, thionyl chloride, oxalyl chloride, phosphorus oxychloride, phosphorus pentachloride, phosphorus trichloride, methanesulfonyl chloride and NaI, p-toluenesulfonyl chloride and NaI, phosphorus tribromide, triphenylphosphine dibromide, phosphorus pentabromide or thionyl bromide, and the like.

The term "coupling agent" refers to a compound that facilitates formation of an amide bond where carboxylic acid activation is required to promote coupling with an amine. Examples of amide coupling agents include, but are not limited to, thionyl chloride, oxalyl chloride, phosphorus oxychloride, Vilsmeier reagent, propylphosphonic anhydride, ethylmethylphosphinic anhydride (EMPA), $Ac_2O$, pivaloyl chloride, ethyl chloroformate (ECF), isobutyl chloroformate (IBCF), 2-ethoxy-1-ethoxycarbonyl-1,2-dihydroquinoline (EEDQ), methanesulfonyl chloride (MsCl), p-toluenesulfonyl chloride (TsCl), pentafluorophenyl trifluoroacetate, cyanuric chloride, 2-chloro-4,6-dimethoxy-1, 3,5-triazine (CDMT), 4-(4,6-dimethoxy-1,3,5-triazin-2-yl)-4-methyl morpholinium chloride (DMTMM), 1-tert-butyl-3-ethylcarbodiimide, 1,1'-carbonyldiimidazole (CDI), N,N'-dicyclohexylcarbodiimide (DCC), N,N'-diisopropylcarbodiimide (DIC), N-(3-dimethylaminopropyl)-N'-ethylcarbodiimide (EDC), 1,3-di-p-tolylcarbodiimide, benzotriazole-1-yl-oxy-tris-(dimethylamino)-phosphonium hexafluorophosphate (BOP), benzotriazole-1-yl-oxy-tris-pyrrolidino-phosphonium hexafluorophosphate (PyBOP), 6-chloro-benzotriazole-1-yloxy-tris-pyrrolidinophosphonium hexafluorophosphate (PyClock), (7-azabenzotriazol-1-yloxy) trispyrrolidinophosphonium hexafluorophosphate (PyAOP), 1-cyano-2-ethoxy-2-oxoethylideneaminooxy-tri s-pyrrolidino-phosphonium hexafluorophosphate (PyOxim), 1-[(1-(cyano-2-ethoxy-2-oxoethylideneaminooxy) dimethylaminomorpholino)]uronium hexafluorophosphate (COMU), 3-(diethoxy-phosphoryloxy)-1,2,3-benzo[d]triazin-4(3H)-one (DEPB T), O-[(ethoxycarbonyl)cyanomethylenamino]-N,N,N',N'-tetramethyluronium tetrafluoroborate (TOTU), O-(2-Oxo-1(2H)pyridyl)-N,N,N',N'-tetramethyluronium tetrafluoroborate (TPTU), 2-(1H-benzotriazole-1-yl)-1,1,3, 3-tetramethylaminium tetrafluoroborate (TBTU), N,N,N', N'-tetramethyl-O—(N-succinimidyl)uronium hexafluorophosphate (HSTU), 2-(1H-benzotriazole-1-yl)-1,13,3-tetramethyluronium hexafluorophosphate (HBTU), 2-(6-Chloro-1H-benzotriazole-1-yl)-1,13,3-tetramethylaminium hexafluorophosphate (HCTU), and 1-[bis(dimethylamino) methylene]-1H-1,2,3-triazolo[4,5-b]pyridinium 3-oxide hexafluorophosphate (HATU).

The term "base" refers to a compound that is an electron pair donor in an acid-base reaction.

The base can be an inorganic base or an organic base.

The term "organic base" refers to a base including at least one C—H bond (e.g. an amine base). In some embodiments, the amine base can be a primary, secondary, or tertiary amine. Examples of an amine base include, but are not limited to, methylamine, dimethylamine, diethylamine, diphenylamine, trimethylamine, triethylamine, N,N-dii isopropylethylamine, diisopropylamine, piperidine, 2,2,6,6-tetramethylpiperidine, pyridine, 2,6-lutidine, 4-methylmorpholine, 4-ethylmorpholine, 1,5-diazabicyclo[4.3.0]non-5-ene, 1,8-diazabicyclo[5.4.0]undec-7-ene, 1,8-diazabicyclo[5.4.0]undec-7-ene, 1,4-diazabicyclo[2.2.2]octane, 1,8-bis(dimethylamino)naphthalene, 4-(dimethylamino)pyridine, and the like.

The term "inorganic base" refers to a base that does not include at least one C—H bond and includes at least one alkali metal or alkaline earth metal. Examples of an inorganic base include, but are not limited to, sodium hydride, potassium hydride, lithium hydride, calcium hydride, barium carbonate, calcium carbonate, cesium carbonate, lithium carbonate, magnesium carbonate, potassium carbonate, sodium carbonate, cesium hydrogen carbonate, potassium hydrogen carbonate, sodium hydrogen carbonate, barium hydroxide, calcium hydroxide, cesium hydroxide, lithium hydroxide, magnesium hydroxide, potassium hydroxide, sodium hydroxide, and the like.

For compounds or pharmaceutically acceptable salts thereof disclosed herein, in which a variable appears more than once, each variable can be a different moiety independently selected from the group defining the variable. For example, where a structure is described having two R groups that are simultaneously present on the same compound, the two R groups can represent different moieties independently selected from the group defined for R.

As used herein, the abbreviations for any protective groups, amino acids and other compounds, are, unless indicated otherwise, in accord with their common usage, recognized abbreviations, or the IUPAC-IUB Commission on Biochemical Nomenclature (See, Biochem. 11:942-944 (1972)).

The phrase "pharmaceutically acceptable" is employed herein to refer to those compounds, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The compounds described herein may be used in neutral form such as a free acid or free base form. Alternatively, the compounds may be used in the form of acid or base addition salts. The term "pharmaceutically acceptable salt" refers to salts of a compound having an acidic or basic moiety which are not biologically or otherwise undesirable for use in a pharmaceutical. In many cases, the compounds disclosed herein are capable of forming acid and/or base salts by virtue of the presence of an acidic or basic moiety (e.g. amino and/or carboxyl groups or groups similar thereto). Pharmaceutically acceptable acid addition salts can be formed by combining a compound having a basic moiety with inorganic acids and organic acids. Inorganic acids which may be used to prepare salts include, for example, hydrochloric acid, hydrobromic acid, sulfuric acid, nitric acid, phosphoric acid, and the like. Organic acids which may be used to prepare salts include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed by combining a compound having an acidic moiety with inorganic and organic bases. Inorganic bases which may be used to prepare salts include, for example, sodium, potassium, lithium, ammonium, calcium, magnesium, iron, zinc, manganese, aluminum hydroxides, carbonates, bicarbonates, phosphates, and the like; particularly preferred are the ammonium, potassium, sodium, calcium, and magnesium hydroxides, carbonates, bicarbonates, or phosphates. Organic bases from which may be used to prepare salts include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. Generally, such salts can be prepared by reacting the free acid or base forms of these compounds with at least a stoichiometric amount of the appropriate base or acid in water or in an organic solvent, or in a mixture of the two; generally, non-aqueous media like ether, ethyl acetate, alcohols (e.g., methanol, ethanol, isopropanol, or butanol) or acetonitrile (ACN) are preferred. Lists of suitable salts are found in WO 87/05297, Johnston et al., published Sep. 11, 1987; Remington's Pharmaceutical Sciences, 17th ed., Mack Publishing Company, Easton, Pa., 1985, p. 1418; and Berge, *J. Pharm. Sci.*, 66, 2 (1977), each of which is incorporated herein by reference in its entirety. A reference for the preparation and selection of pharmaceutical salts of the present disclosure is P. H. Stahl & C. G. Wermuth "Handbook of Pharmaceutical Salts," Verlag Helvetica Chimica Acta, Zurich, 2002 which is incorporated herein by reference in its entirety.

Preparations

The present invention further relates to a preparation of a compound of the invention, or a salt thereof. As used herein, a "preparation" is, for example, a product of a process used to make or purify a compound of the invention, or salt thereof. In some embodiments, the preparation may optionally include one or more impurities, residual solvent, or a combination thereof. The preparation can be liquid or solid.

In some embodiments, the present invention relates to a preparation of a compound of formula (Ia):

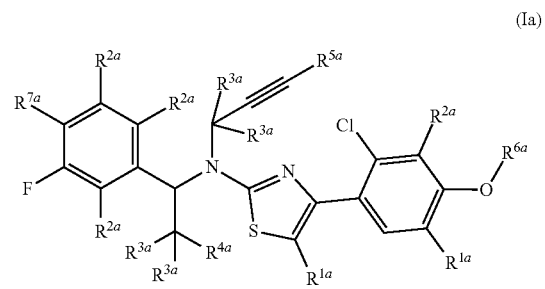

(Ia)

or a pharmaceutically acceptable salt thereof, wherein:
each $R^{1a}$ is independently $C(R^4)_3$ or $C(R^4)_2R^B$;
each $R^4$ is independently hydrogen or deuterium;
$R^B$ is —$OR^C$;

$R^C$ is hydrogen or deuterium;

each $R^{2a}$ is independently hydrogen or deuterium;

each $R^{3a}$ is independently hydrogen or deuterium;

$R^{4a}$ is

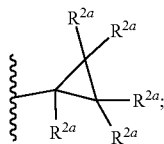

$R^{5a}$ is hydrogen or deuterium;

$R^{61}$ is $^{13}C(R^A)_3$ or $C(R^A)_3$; and $R^{7a}$ is $C(R^A)_3$ or $C(R^A)_2R^B$, wherein at least one of $R^{1a}$ and $R^{7a}$ is $C(R^A)_2R^B$.

In some embodiments, the present invention relates to a preparation of a compound of formula (Ia):

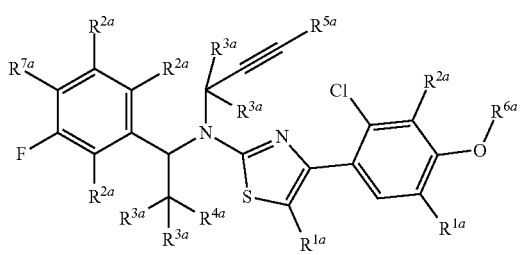

(Ia)

or a pharmaceutically acceptable salt thereof, wherein:

each $R^{1a}$ is independently $C(R^A)_3$ or $C(R^A)_2R^B$;

each $R^A$ is independently hydrogen or deuterium;

$R^B$ is —$OR^C$;

$R^C$ is hydrogen or deuterium;

each $R^{2a}$ is independently hydrogen or deuterium;

each $R^{1a}$ is independently hydrogen or deuterium;

$R^{4a}$ is

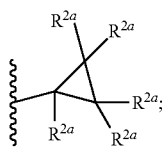

$R^{5a}$ is hydrogen or deuterium;

$R^{6a}$ is $C(R^A)_3$; and $R^{7a}$ is $C(R^A)_3$ or $C(R^A)_2R^B$, wherein at least one of $R^{1a}$ and $R^{7a}$ is $C(R^A)_2R^B$.

In some embodiments, $R^{7a}$ is $C(R^A)_2R^B$; and $R^C$ is hydrogen.

In some embodiments, $R^{7a}$ is $CH_2OH$.

In some embodiments, the present invention relates to a preparation of a compound of formula (IIa):

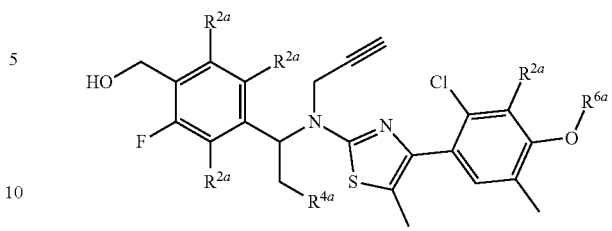

(IIa)

or a pharmaceutically acceptable salt thereof.

In some embodiments, $R^{6a}$ is $CD_3$ or $R^{6a}$ is $CH_3$.

In some embodiments, $R^{6a}$ is $CD_3$.

In some embodiments, each $R^{2a}$ is hydrogen.

In some embodiments, $R^{7a}$ is $CD_2OH$.

In some embodiments, the compound of the preparation is a compound having the formula:

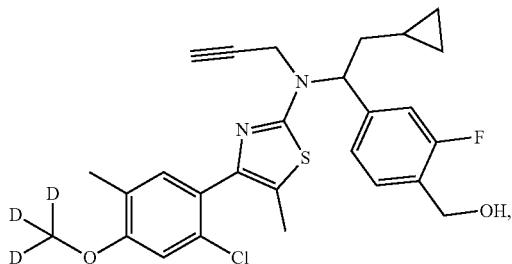 [SMILES: [2H]C([2H])([2H])Oc1cc(Cl)c(-c2nc(N(CC#C)C(CC3CC3)c3ccc(CO)c(F)c3)sc2C)cc1C]

or a pharmaceutically acceptable salt thereof.

In some embodiments, the compound of the preparation is a compound of formula:

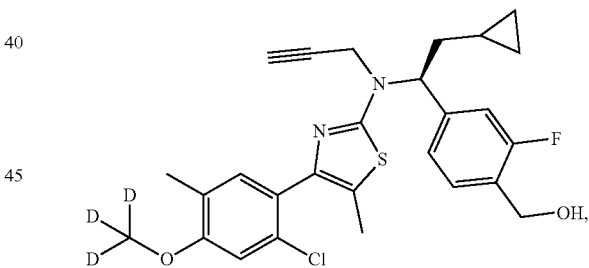

or a pharmaceutically acceptable salt thereof.

In some embodiments, the compound of the preparation is a compound of formula:

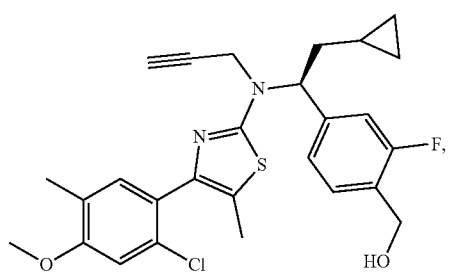 [SMILES: C#CCN(c1nc(-c2cc(C)c(OC)cc2Cl)c(C)s1)[C@@H](CC1CC1)c1ccc(CO)c(F)c1]

or a pharmaceutically acceptable salt thereof.

In some embodiments, the compound of the preparation is in at least about 5%, at least about 10%, at least about 20%, at least about 30%, at least about 40%, at least about 50%, at least about 60%, at least about 70%, at least about 80%, at least about 90%, at least about 95%, at least about 99%, or at least about 99.9% enantiomeric excess, or an enantiomeric excess within a range defined by any of the preceding numbers.

In some embodiments, the preparation comprises at least about 5%, at least about 10%, at least about 20%, at least about 30%, at least about 40%, at least about 50%, at least about 60%, at least about 70%, at least about 80%, at least about 90%, at least about 95%, at least about 99%, or at least about 99.9% by weight of the compound, or a % by weight within a range defined by any of the preceding numbers.

In some embodiments, the preparation comprises at least about 50%, at least about 60%, at least about 70%, at least about 80%, at least about 90%, at least about 95%, at least about 99%, or at least about 99.9% by weight of the compound, or a % by weight within a range defined by any of the preceding numbers.

In some embodiments, the preparation comprises at least about 50% by weight of the compound.

In some embodiments, the preparation comprises at least about 75% by weight of the compound.

In some embodiments, the preparation comprises at least about 90% by weight of the compound.

In some embodiments, the preparation comprises at least about 95% by weight of the compound.

In some embodiments, the preparation is in the form of a solid, i.e., a solid preparation.

In some embodiments, the preparation is used to prepare a pharmaceutical composition.

Prodrugs

"Prodrug" is meant to indicate a compound that may be converted under physiological conditions or by solvolysis to a biologically active compound, such as Compound 2 described herein. Thus, the term "prodrug" refers to a metabolic precursor of a compound described herein that is pharmaceutically acceptable. A prodrug may be inactive when administered to a subject in need thereof, but is converted in vivo to an active compound as described herein. Prodrugs are typically rapidly transformed in vivo to yield the parent compound described herein, for example, by hydrolysis in blood. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam). A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein.

In one embodiment, compounds of formulae (IIIaa), (IIIbb), (IIIcc), (IIIdd), (IIIee) and (IIIff) serve as prodrugs to Compound 2; that is, the compound may be converted under physiological conditions to Compound 2. In another embodiment, the compounds of formulae (IIIaa), (IIIbb), (IIIcc), (IIIdd), (IIIee) and (IIIff) are themselves CRFs inhibitors.

Some embodiments provide a compound of formula (III):

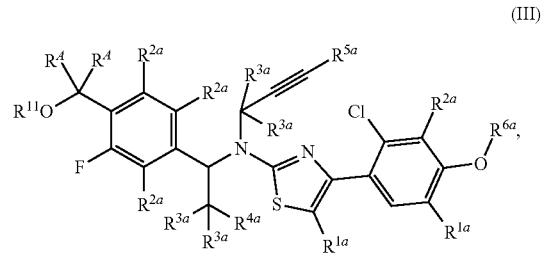

(III)

or a pharmaceutically acceptable salt thereof, wherein:
$R^{11}$ is —P(═O)(OR$^{33}$)$_2$ or —P(═O)(OR$^{33}$)(N(R$^{33}$)$_2$);
b) —C(═O)R$^{50}$;
c) —C(═O)N(R$^{33}$)R$^{50}$;
d) —C(═O)OR$^{50}$; or
e) R$^{50}$;
each $R^{33}$ is independently hydrogen, $C_1$-$C_6$alkyl, halo$C_1$-$C_6$alkyl or aryl, wherein the $C_1$-$C_6$alkyl and aryl are each optionally substituted with $R^{10}$;
$R^{50}$ is $C_1$-$C_6$alkyl, $C_3$-$C_7$cycloalkyl, $C_3$-$C_7$ cycloalkenyl, $C_2$-$C_6$ alkenyl, $C_2$-$C_6$alkynyl, aryl, heteroaryl, or heterocyclyl, each of which is optionally substituted with one or more $R^{10}$ and/or $R^{20}$;
each $R^{10}$ is independently halo, halo$C_1$-$C_6$alkyl, cyano, nitro, trimethylsilanyl, —O·(oxyl radical), —OR$^{30}$, —SR$^{30}$, —OC(O)—R$^{30}$, —OC(O)O—R$^{30}$, —N(R$^{30}$)$_2$, —C(O)R$^{30}$, —C(O)OR$^{30}$, —OC(O)N(R$^{30}$)$_2$, —C(O)N(R$^{30}$)$_2$, —N(R$^{30}$)C(O)OR$^{31}$, —N(R$^{30}$)C(O)R$^{31}$, —N(R$^{30}$)C(═NR$^{31}$)N(R$^{32}$)$_2$, —N(R$^{30}$)S(O)$_t$R$^{31}$, —S(O)$_t$OR$^{30}$, —S(O)$_p$R$^{30}$, —S(O)$_t$N(R$^{30}$)$_2$, —OP(═O)(OR$^{30}$)$_2$, or optionally two $R^{10}$ groups taken together on a single atom form oxo;
each t is independently 1 or 2;
each p is independently 1, 2 or 3;
each $R^{20}$ is independently $C_1$-$C_6$alkyl, $C_2$-$C_6$ alkenyl, aryl, $C_3$-$C_7$cycloalkyl, $C_3$-$C_7$ cycloalkenyl, heterocyclyl, or heteroaryl, wherein each $R^{20}$ is optionally substituted with $R^{10}$ and/or $R^{22}$;
each $R^{22}$ is independently $C_1$-$C_6$alkyl, $C_2$-$C_6$ alkenyl, aryl, $C_3$-$C_7$cycloalkyl, $C_3$-$C_7$ cycloalkenyl, heterocyclyl, or heteroaryl, wherein each $R^{22}$ is optionally substituted with $R^{10}$; and
each $R^{30}$, $R^{31}$ and $R^{32}$ is independently hydrogen, halo$C_1$-$C_6$alkyl, or $C_1$-$C_6$alkyl;
each $R^{1a}$ is independently C(R$^A$)$_3$;
each $R^A$ is independently hydrogen or deuterium;
each $R^{2a}$ is independently hydrogen or deuterium;
each $R^{3a}$ is independently hydrogen or deuterium;
$R^{4a}$ is

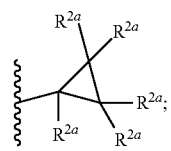

$R^{5a}$ is hydrogen or deuterium;
$R^{61}$ is C(R$^A$)$_3$; and
$R^{7a}$ is C(R$^A$)$_3$.

In some embodiments, each $R^{33}$ is independently hydrogen, $C_1$-$C_6$alkyl, halo$C_1$-$C_6$alkyl or aryl; $R^{50}$ is $C_1$-$C_6$alkyl, $C_3$-$C_7$cycloalkyl, $C_3$-$C_7$ cycloalkenyl, $C_2$-$C_6$ alkenyl, $C_2$-$C_6$alkynyl, aryl, heteroaryl, or heterocyclyl; each $R^{20}$ is independently $C_1$-$C_6$alkyl, $C_2$-$C_6$ alkenyl, aryl, $C_3$-$C_7$cycloalkyl, $C_3$-$C_7$ cycloalkenyl, heterocyclyl, or heteroaryl; each $R^{22}$ is independently $C_1$-$C_6$alkyl, $C_2$-$C_6$ alkenyl, aryl, $C_3$-$C_7$cycloalkyl, $C_3$-$C_7$ cycloalkenyl, heterocyclyl, or heteroaryl; and each $R^{30}$, $R^{3'}$ and $R^{32}$ is independently hydrogen, halo$C_1$-$C_6$alkyl, or $C_1$-$C_6$alkyl.

In some embodiments, the compound is a compound of formula (Ma):

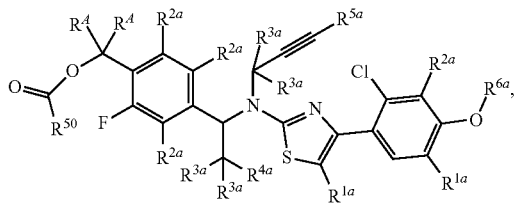
(IIIa)

or a pharmaceutically acceptable salt thereof.

In some embodiments, the compound is a compound of formula (IIIaa):

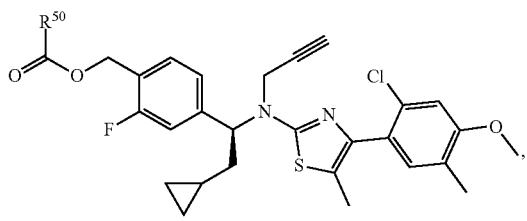
(IIIaa)

or a pharmaceutically acceptable salt thereof.

In some embodiments, the compound is a compound of formula (IIIb):

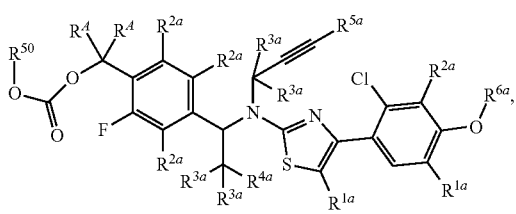
(IIIb)

or a pharmaceutically acceptable salt thereof.

In some embodiments, the compound is a compound of formula (IIIbb):

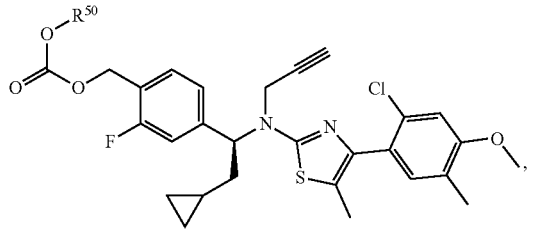
(IIIbb)

or a pharmaceutically acceptable salt thereof.

In some embodiments, the compound is a compound of formula (IIIc):

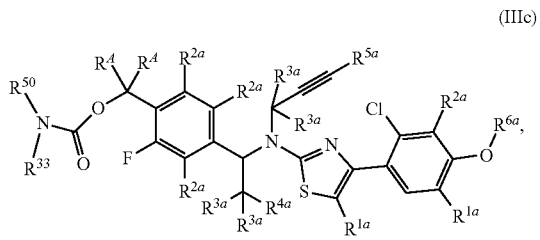
(IIIc)

or a pharmaceutically acceptable salt thereof.

In some embodiments, the compound is a compound of formula (IIIcc):

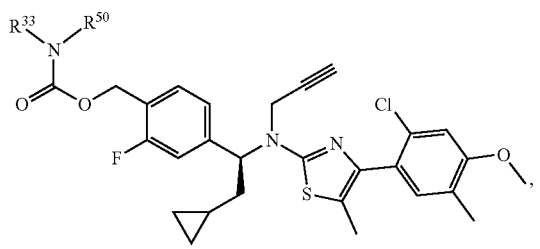
(IIIcc)

or a pharmaceutically acceptable salt thereof.

In some embodiments, the compound is a compound of formula (IIId):

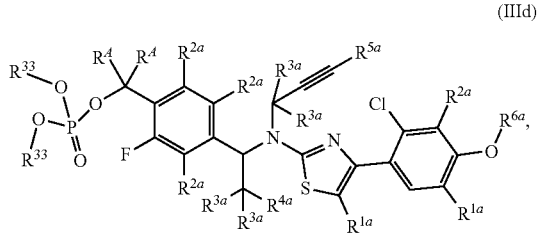
(IIId)

or a pharmaceutically acceptable salt thereof.

In some embodiments, the compound is a compound of formula (IIIdd):

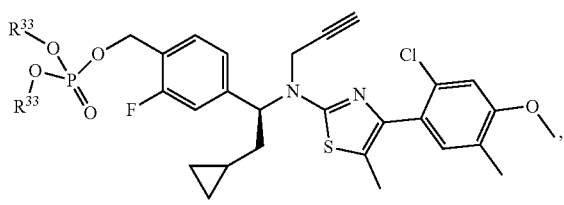
(IIIdd)

or a pharmaceutically acceptable salt thereof.

In some embodiments, the compound is a compound of formula (IIIe):

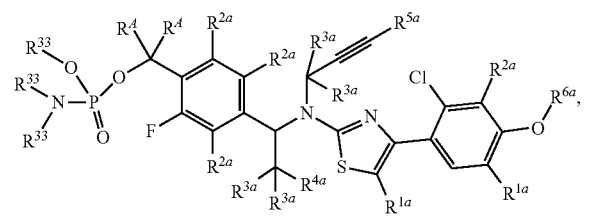
(IIIe)

or a pharmaceutically acceptable salt thereof.

In some embodiments, the compound is a compound of formula (IIIee):

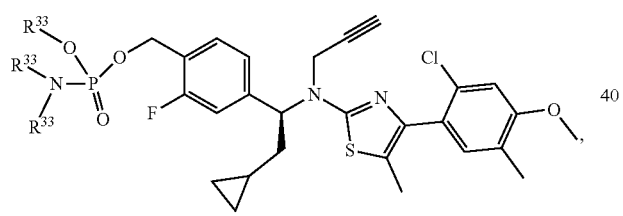
(IIIee)

or a pharmaceutically acceptable salt thereof.

In some embodiments, the compound is a compound of formula (IIIf):

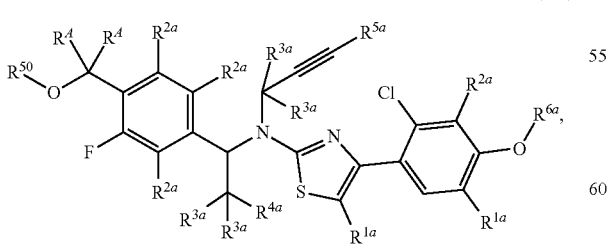
(IIIf)

or a pharmaceutically acceptable salt thereof.

In some embodiments, the compound is a compound of formula (IIIff):

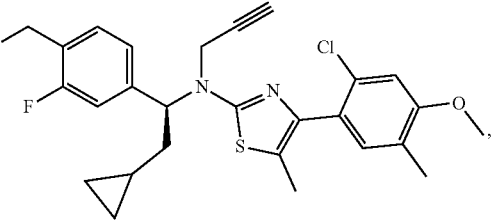
(IIIff)

or a pharmaceutically acceptable salt thereof.

In some embodiments, $R^{11}$ is selected from one of the following:

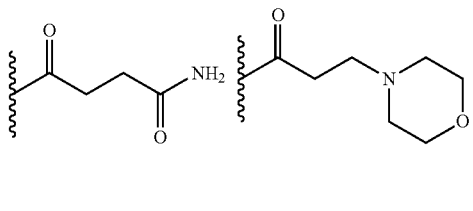

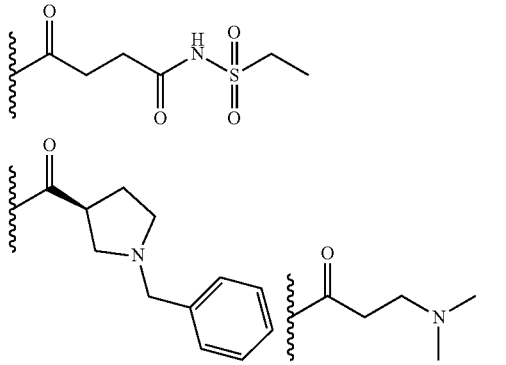

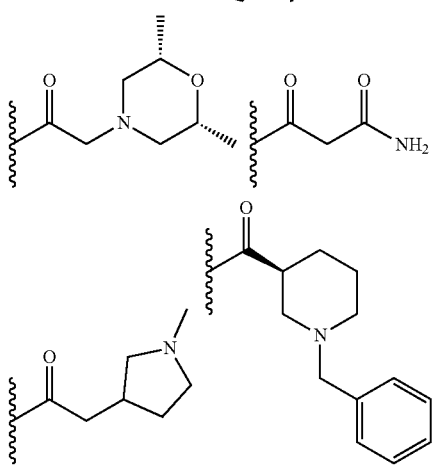

-continued
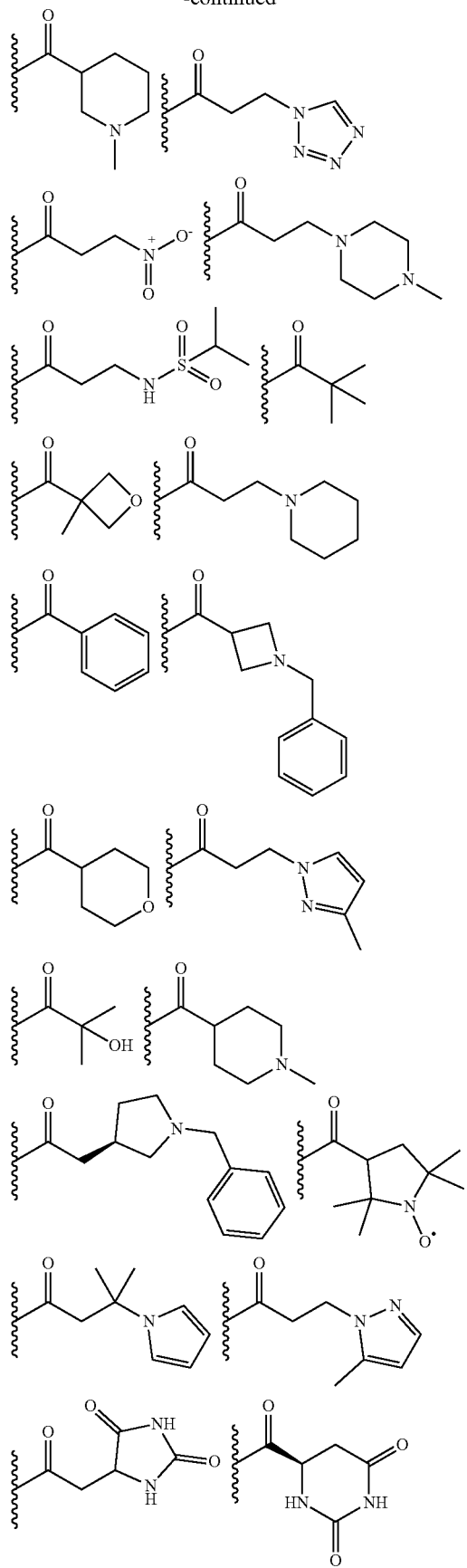
-continued
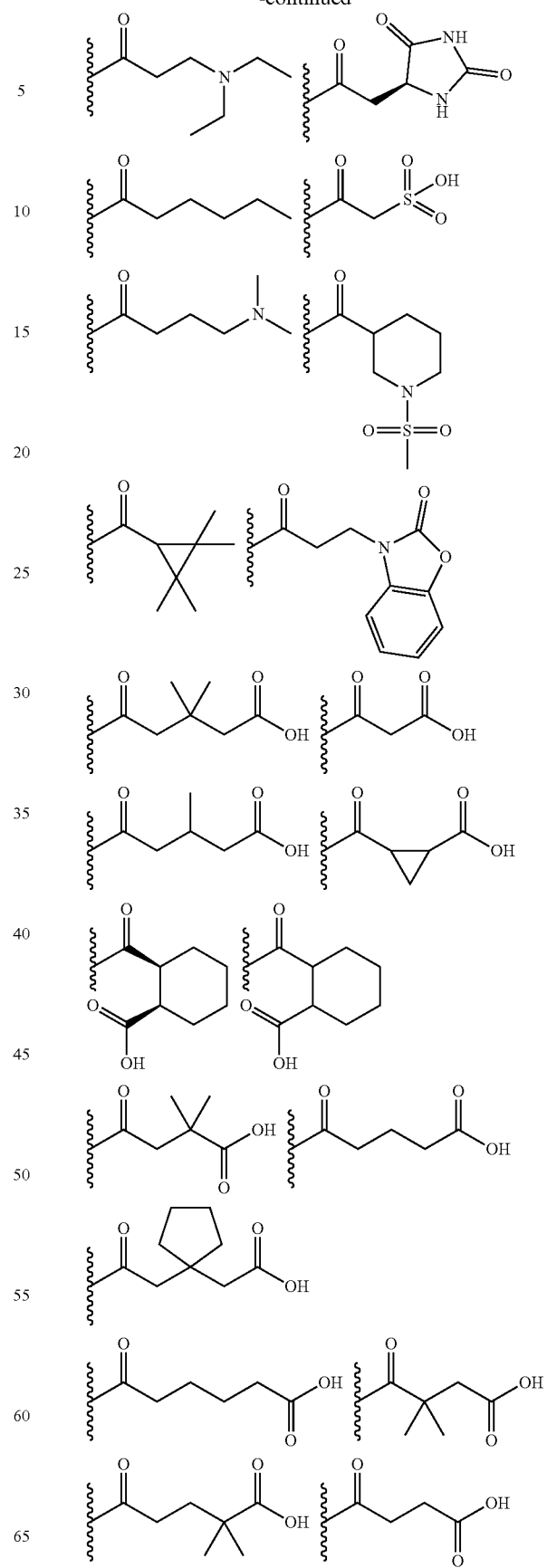

-continued
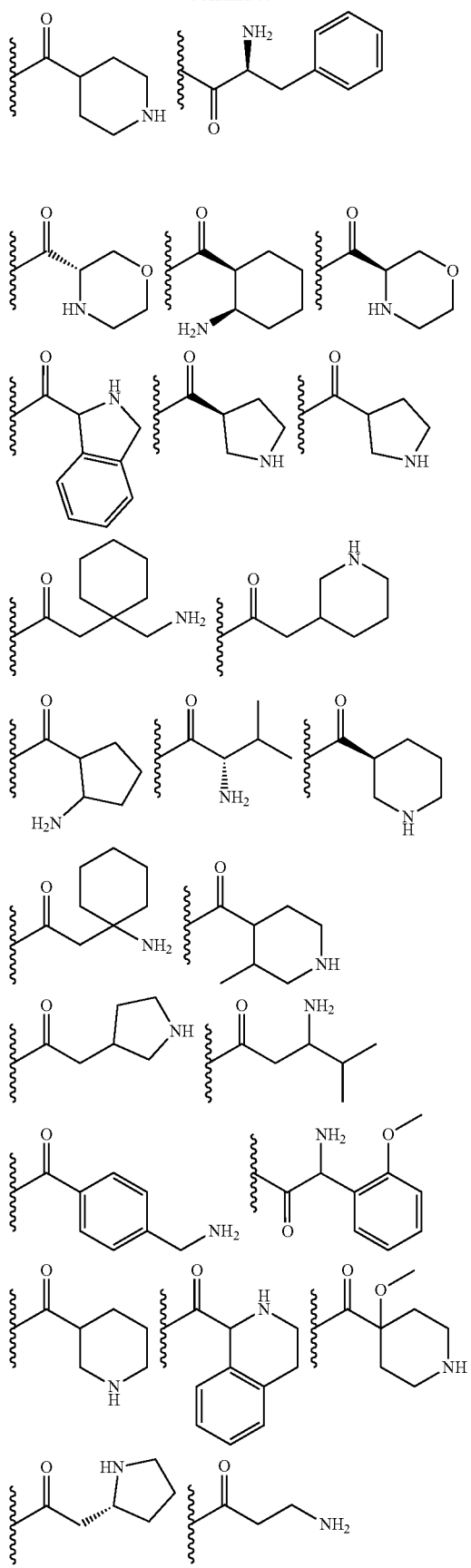

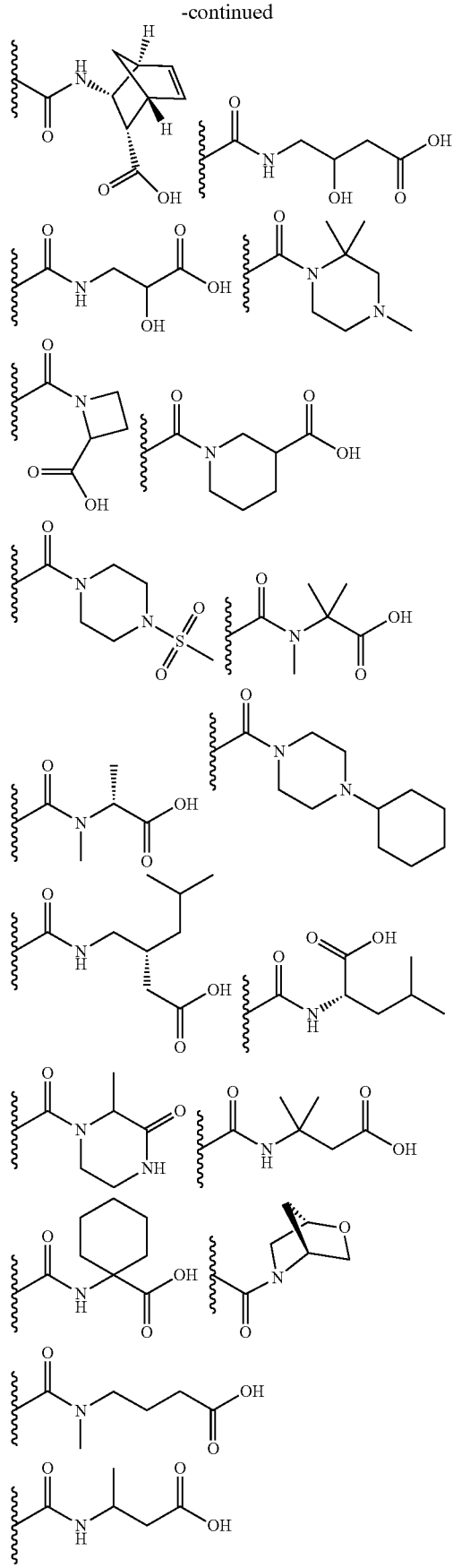
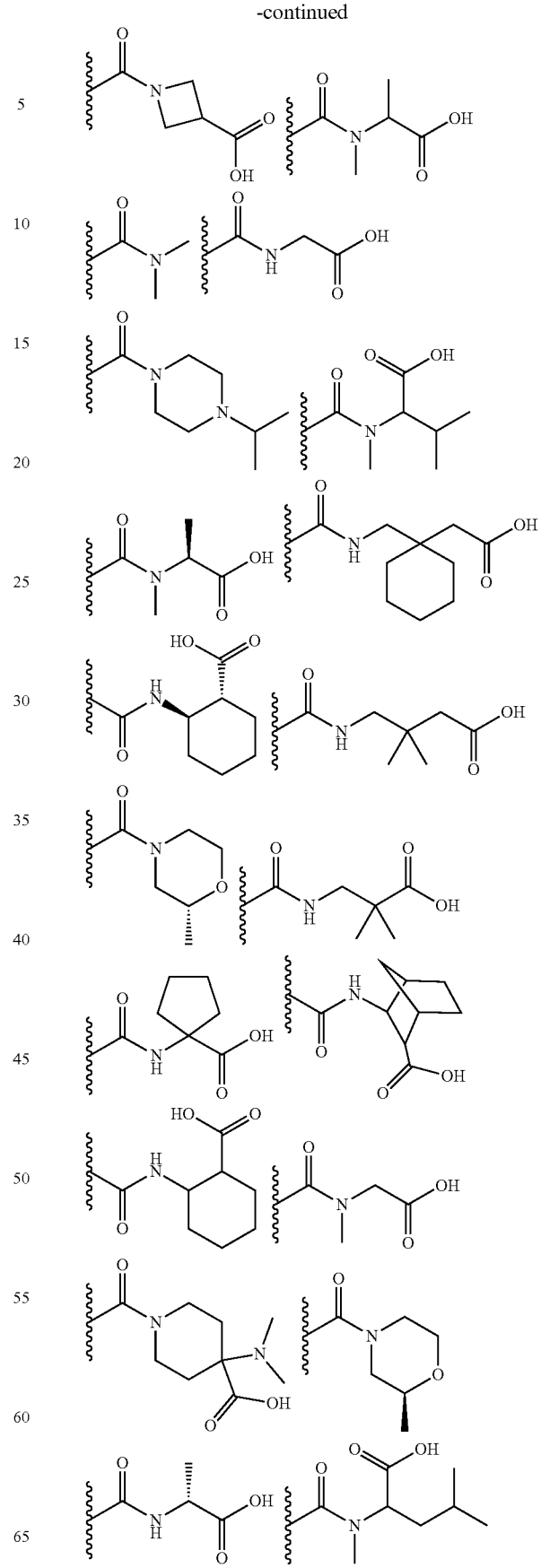

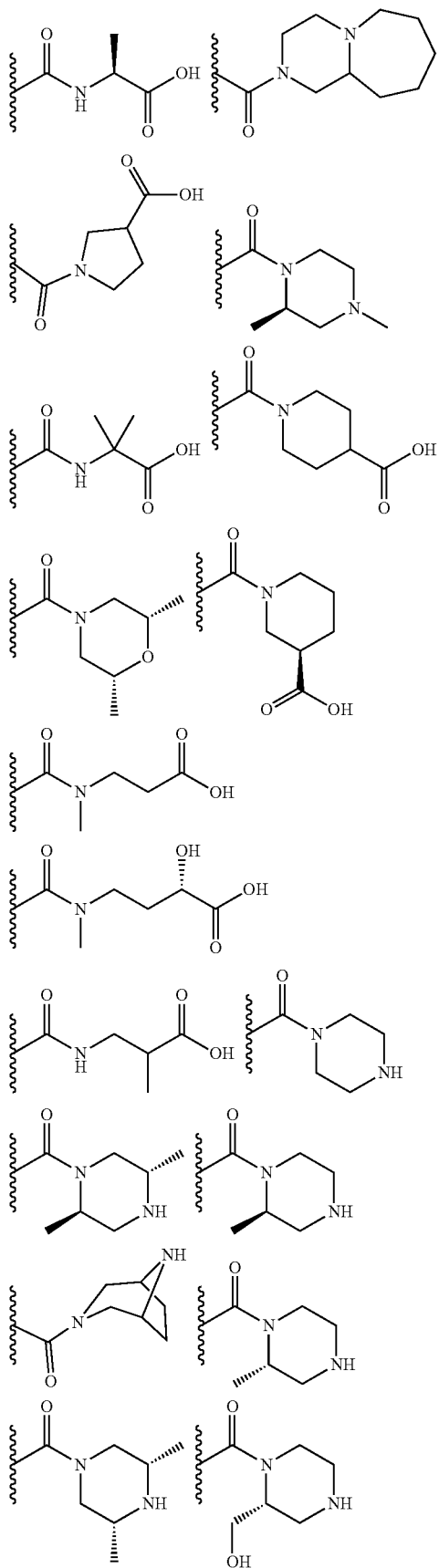
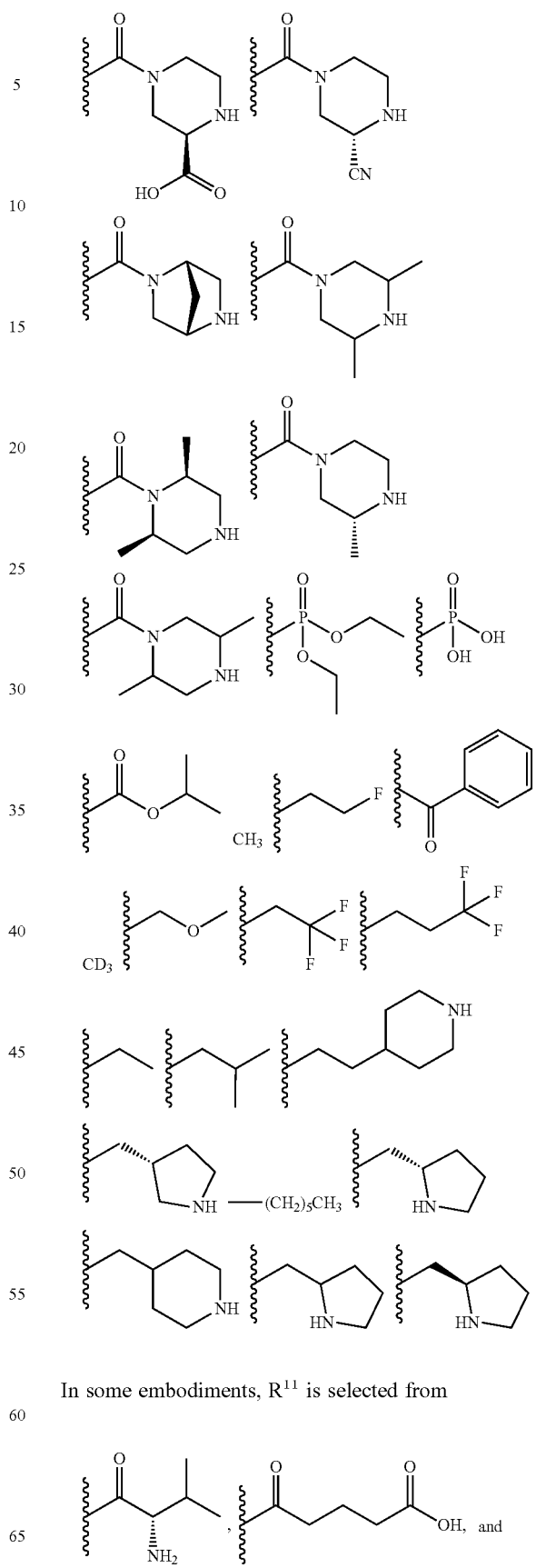
In some embodiments, $R^{11}$ is selected from

-continued

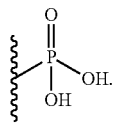

In some embodiments, the compound is a compound of formula:

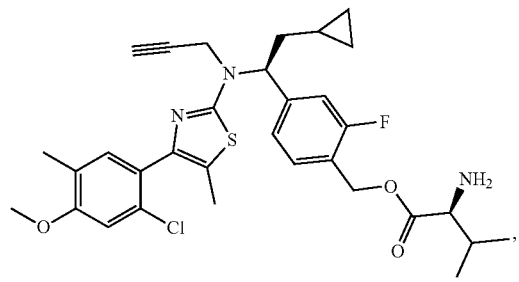 [SMILES: C#CCN(c1nc(-c2cc(C)c(OC)cc2Cl)c(C)s1)[C@@H](CC1CC1)c1ccc(COC(=O)[C@@H](N)C(C)C)c(F)c1]

or a pharmaceutically acceptable salt thereof.

In some embodiments, the compound is a hydrochloric acid salt of a compound of formula:

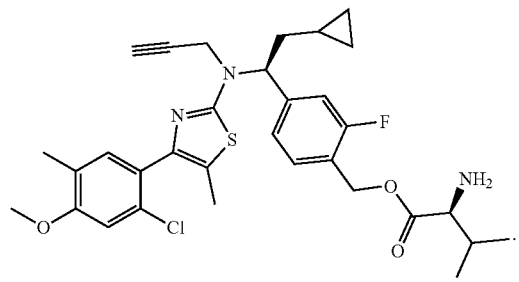 [SMILES: C#CCN(c1nc(-c2cc(C)c(OC)cc2Cl)c(C)s1)[C@@H](CC1CC1)c1ccc(COC(=O)[C@@H](N)C(C)C)c(F)c1]

In some embodiments, the compound is a compound of formula:

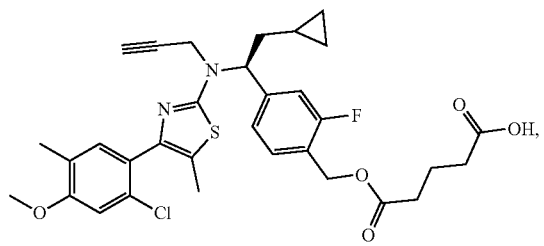 [SMILES: C#CCN(c1nc(-c2cc(C)c(OC)cc2Cl)c(C)s1)[C@@H](CC1CC1)c1ccc(COC(=O)CCCC(=O)O)c(F)c1]

or a pharmaceutically acceptable salt thereof.

In some embodiments, the compound is a sodium salt of a compound of formula:

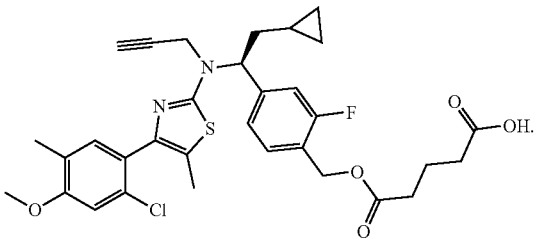 [SMILES: C#CCN(c1nc(-c2cc(C)c(OC)cc2Cl)c(C)s1)[C@@H](CC1CC1)c1ccc(COC(=O)CCCC(=O)O)c(F)c1]

In some embodiments, the compound is a compound of formula:

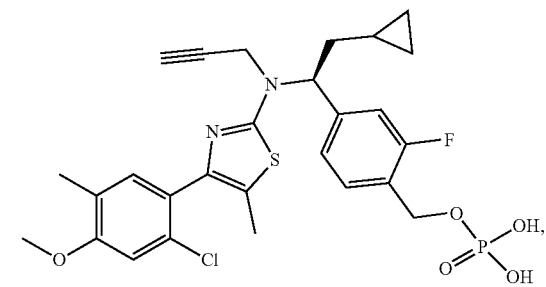 [SMILES: C#CCN(c1nc(-c2cc(C)c(OC)cc2Cl)c(C)s1)[C@@H](CC1CC1)c1ccc(COP(=O)(O)O)c(F)c1]

or a pharmaceutically acceptable salt thereof.

In some embodiments, the compound is a sodium salt of a compound of formula:

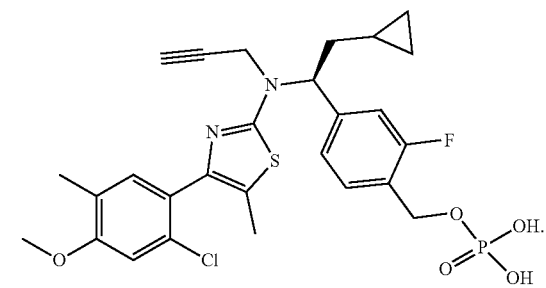 [SMILES: C#CCN(c1nc(-c2cc(C)c(OC)cc2Cl)c(C)s1)[C@@H](CC1CC1)c1ccc(COP(=O)(O)O)c(F)c1]

In some embodiments, the compound is a bis-sodium salt of a compound of formula:

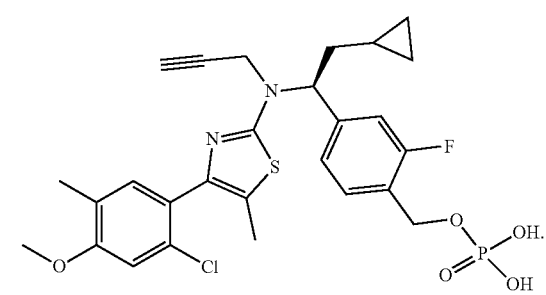 [SMILES: C#CCN(c1nc(-c2cc(C)c(OC)cc2Cl)c(C)s1)[C@@H](CC1CC1)c1ccc(COP(=O)(O)O)c(F)c1]

Compounds of formula (III) can be prepared according to the synthetic methods described in International Pub. No. WO 2016/127133 A1. For example, compounds of Formulae (IIIaa), (IIIbb), (IIIcc), (IIIdd), (IIIee) and (IIIff) can be prepared according to the synthetic methods described in International Pub. No. WO 2016/127133 A1 using Compound 2 as starting material in place of R2R,3S,11bR)-9,10-dimethoxy-3-(2-methylpropyl)-1H,2H,3H,4H,6H,7H,11bH-pyrido[2, isoquinolin-2-yl]methanol.

In some embodiments, compounds of formula (IIIaa) can be prepared by reacting Compound 2, as starting material, with $R^{50}C(=O)OH$ with in the presence of a coupling agent (e.g. 1-(3-dimethylaminopropyl)-3-ethylcarbodiimide hydrochloride (EDCI)) and a base (e.g. amine base such as dimethylaminopyridine (DMAP)) in a solvent such as methylene chloride. In some embodiments, compounds of formula (IIIaa) can be prepared by reacting Compound 2, as starting material, with $R^{50}C(=O)X$ (X is Cl, Br, or I) in a solvent such as methylene chloride where $R^{50}C(=O)X$ can be purchased when commercially available or prepared by reacting $R^{50}C(=O)OH$ with a halogenating agent (e.g. thionyl chloride). In some embodiments, compounds of formula (IIIaa) can be prepared by reacting Compound 2, as starting material, with $R^{50}C(=O)OC(=O)R^{60}$ where $R^{50}C(=O)OC(=O)R^{60}$ can be purchased when commercially available or prepared by reacting $R^{50}C(=O)OH$ with $R^{60}C(=O)X$ in a solvent in the presence of a base where $R^{60}$ is $C_1$-$C_6$alkyl, $C_2$-$C_6$ alkenyl, aryl, $C_3$-$C_7$cycloalkyl, $C_3$-$C_7$ cycloalkenyl, heterocyclyl, or heteroaryl, each optionally substituted with one or more substituents selected from halo, $C_1$-$C_6$alkyl, halo$C_1$-$C_6$alkyl, cyano, and nitro.

In some embodiments, compounds of formula (IIIbb) can be prepared by reacting Compound 2, as starting material, with p-nitrophenyl chloroformate, 1,1-bis[6-(trifluoromethyl)benzotriazolyl]carbonate, di(2-pyridyl) carbonate, N,N'-disuccinimidyl carbonate, phenyl 4,5-dichloro-6-oxopyridazine-1(6H)-carboxylate, CDI, phosgene or triphosgene optionally in the presence of a base (e.g. DMAP) in a solvent followed by treatment with $R^{50}OH$.

In some embodiments, compounds of formula (IIIcc) can be prepared by reacting Compound 2, as starting material, with p-nitrophenyl chloroformate, 1,1-bis[6-(trifluoromethyl)benzotriazolyl]carbonate, di(2-pyridyl) carbonate, N,N'-disuccinimidyl carbonate, phenyl 4,5-dichloro-6-oxopyridazine-1(6H)-carboxylate, CDI, phosgene or triphosgene optionally in the presence of a base (e.g. DIPEA or DMAP) in a solvent followed by treatment with $R^{50}R^{33}NH$.

In some embodiments, compounds of formula (IIIdd) can be prepared by reacting Compound 2, as starting material, with $(R^{33}O)_2P(=O)X$ (X is Cl, Br, or I) in a solvent (e.g. pyridine) or a solvent (e.g. methylene chloride) and base (e.g. DIPEA).

In some embodiments, compounds of formula (IIIee) can be prepared by reacting $R^{50}R^{33}NH$ with $(R^{33}O)P(=O)(X)_2$ (X is Cl, Br, or I) in a solvent (e.g. methylene chloride) and optionally a base (e.g. TEA or N-methylimidazole) to afford a chlorophosphoramidate intermediate $((R^{33}O)(R^{50}R^{33}N)P(=O)(X))$ which can be then treated with Compound 2, as starting material.

In some embodiments, compounds of formula (IIIff) can be prepared by reacting Compound 2, as starting material, with a base (e.g. NaH), or in the presence of a base (e.g. $K_2CO_3$), in a solvent (e.g. DMF or DMSO) and then treating with $R^{50}X$ (X is Cl, Br, or I) or $R^{50}S(=O)_2R^{60}$ where $R^{60}$ is $C_1$-$C_6$alkyl, $C_2$-$C_6$ alkenyl, aryl, $C_3$-$C_7$cycloalkyl, $C_3$-$C_7$ cycloalkenyl, heterocyclyl, or heteroaryl, each optionally substituted with one or more substituents selected from halo, $C_1$-$C_6$alkyl, halo$C_1$-$C_6$alkyl, cyano, and nitro.

In some embodiments, compounds of formula (IIIff) can be prepared by reacting Compound 2, as starting material, with a halogenating agent (p-toluenesulfonyl chloride (TsCl) or methanesulfonyl chloride (MsCl)) optionally in the presence of a base (e.g. $K_2CO_3$), in a solvent (e.g. DMF) and then combining with $R^{50}OH$ in the presence of a base (e.g. $K_2CO_3$), in a solvent (e.g. DMF) or with an alkoxide of $R^{50}OH$ prepared by reacting $R^{50}OH$ with a base (e.g. NaH) in a solvent (e.g. DMF or DMSO).

Methods of Use

Provided herein are methods of treating congenital adrenal hyperplasia (CAH) comprising administering a therapeutically effective amount of a compound of the invention, or a pharmaceutically acceptable salt thereof, to a subject in need thereof. In some embodiments, the compound is a compound of formula (I), or a pharmaceutically acceptable salt thereof. In some embodiments, the compound is a compound of formula (Ia), or a pharmaceutically acceptable salt thereof. In some embodiments, the compound is a compound of formula (III), or a pharmaceutically acceptable salt thereof. In some embodiments, the compound is Compound 4 or 5, or a pharmaceutically acceptable salt thereof. In some embodiments, the compound is Compound 6, 7, or 8, or a pharmaceutically acceptable salt thereof.

Provided herein are methods of treating congenital adrenal hyperplasia (CAH) comprising administering a therapeutically effective amount of a pharmaceutical composition comprising a compound of the invention, or a pharmaceutically acceptable salt thereof; and at least one pharmaceutically acceptable excipient, to a subject in need thereof. In some embodiments, the compound is a compound of formula (I), or a pharmaceutically acceptable salt thereof. In some embodiments, the compound is a compound of formula (Ia), or a pharmaceutically acceptable salt thereof. In some embodiments, the compound is a compound of formula (III), or a pharmaceutically acceptable salt thereof. In some embodiments, the compound is Compound 2, 4, or 5, or a pharmaceutically acceptable salt thereof. In some embodiments, the compound is Compound 6, 7, or 8, or a pharmaceutically acceptable salt thereof.

Provided herein are methods of treating congenital adrenal hyperplasia (CAH) comprising administering a compound of the invention, or a pharmaceutically acceptable salt thereof, to normalize or partially normalize levels of biomarkers associated with congenital adrenal hyperplasia. In some embodiments, normalizing or partially normalizing levels of biomarkers comprises reducing levels of elevated biomarkers or increasing levels of depressed biomarkers as compared to subject without CAH. In some embodiments, the compound is a compound of formula (I), or a pharmaceutically acceptable salt thereof. In some embodiments, the compound is a compound of formula (Ia), or a pharmaceutically acceptable salt thereof. In some embodiments, the compound is a compound of formula (III), or a pharmaceutically acceptable salt thereof. In some embodiments, the compound is Compound 4 or 5, or a pharmaceutically acceptable salt thereof. In some embodiments, the compound is Compound 6, 7, or 8, or a pharmaceutically acceptable salt thereof.

Provided herein are methods of treating congenital adrenal hyperplasia (CAH) comprising administering a pharmaceutical composition comprising a compound of the invention, or a pharmaceutically acceptable salt thereof; and at least one pharmaceutically acceptable excipient, to normalize or partially normalize levels of biomarkers associated with congenital adrenal hyperplasia. In some embodiments, the compound is a compound of formula (I), or a pharmaceutically acceptable salt thereof. In some embodiments, the compound is a compound of formula (Ia), or a pharmaceutically acceptable salt thereof. In some embodiments, the compound is a compound of formula (III), or a pharmaceutitically acceptable salt thereof. In some embodiments, the compound is Compound 2, 4, or 5, or a pharmaceutically acceptable salt thereof. In some embodiments, the compound is Compound 6, 7, or 8, or a pharmaceutically acceptable salt thereof.

Provided herein is a method of treating congenital adrenal hyperplasia in a subject in need thereof comprising administering a compound of the invention, or a pharmaceutically acceptable salt thereof, in an amount sufficient to reduce the level of one or more biomarker(s) associated with congenital adrenal hyperplasia. In some embodiments, the biomarkers are selected from (a) 17-hydroxyprogesterone (17-OHP); (b) testosterone; and (c) androstenedione in the subject. In some embodiments, the compound is a compound of formula (I), or a pharmaceutically acceptable salt thereof. In some embodiments, the compound is a compound of formula (Ia), or a pharmaceutically acceptable salt thereof. In some embodiments, the compound is a compound of formula (III), or a pharmaceutically acceptable salt thereof. In some embodiments, the compound is Compound 4, or 5, or a pharmaceutically acceptable salt thereof. In some embodiments, the compound is Compound 6, 7, or 8, or a pharmaceutically acceptable salt thereof.

Provided herein is a method of treating congenital adrenal hyperplasia in a subject in need thereof comprising administering a pharmaceutical composition comprising a compound of the invention, or a pharmaceutically acceptable salt thereof; and at least one pharmaceutically acceptable excipient, in an amount sufficient to reduce the level of one or more biomarker(s) associated with congenital adrenal hyperplasia. In some embodiments, the biomarkers are selected from (a) 17-hydroxyprogesterone (17-OHP); (b) testosterone; and (c) androstenedione in the subject. In some embodiments, the compound is a compound of formula (I), or a pharmaceutically acceptable salt thereof. In some embodiments, the compound is a compound of formula (Ia), or a pharmaceutically acceptable salt thereof. In some embodiments, the compound is a compound of formula (III), or a pharmaceutically acceptable salt thereof. In some embodiments, the compound is Compound 2, 4, or 5, or a pharmaceutically acceptable salt thereof. In some embodiments, the compound is Compound 6, 7, or 8, or a pharmaceutically acceptable salt thereof.

In some embodiments, the reduction in level of any of the biomarkers (e.g., any of 17-OHP, testosterone, and androstenedione) is determined by comparing the level of the biomarker as measured during the circadian release on a day prior to administering the compound of the invention, or a pharmaceutically acceptable salt thereof and the level of the biomarker as measured during the circadian release on the day after administering the compound of the invention, or a pharmaceutically acceptable salt thereof. A day prior to administering the compound of the invention, or a pharmaceutically acceptable salt thereof applies to a subject that has not previously been administered the compound of the invention, or a pharmaceutically acceptable salt thereof within at least the past 24 hours.

In some embodiments, the circadian release of biomarkers associated with CAH occurs between the hours of 2 a.m. and 10 a.m. In other embodiments, the circadian release of biomarkers associated with CAH occurs between the hours of 6 a.m. and 10 a.m.

In some embodiments of any of the methods disclosed herein, the compound of the invention, or a pharmaceutically acceptable salt thereof, is administered to the subject at nighttime or administration prior to sleep (i.e., bedtime administration). In some embodiments, the compound of the invention, or a pharmaceutically acceptable salt thereof, is administered three to eight hours prior to the circadian release of the biomarker. In some embodiments, the compound of the invention, or a pharmaceutically acceptable salt thereof, is administered six to eight hours prior to the circadian release of the biomarker. Administration prior to the circadian release may be adapted for shift workers (e.g., those who work at night and sleep during the day), in which case administration will not necessarily occur at nighttime. Administration is therefore dependent upon the expected circadian release of the biomarker, and can vary depending upon the individual's (i.e., subject, patient) particular work and sleep patterns.

In some embodiments of the methods provided herein, the level of 17-hydroxyprogesterone in a subject is reduced by at least about 10%, at least about 15%, at least about 20%, at least about 25%, at least about 30%, at least about 35%, at least about 40%, at least about 50%, at least about 55% or at least about 60% from pre-administration levels. In some embodiments, the level of 17-hydroxyprogesterone is reduced by at least about 25%. In some embodiments, the level of 17-hydroxyprogesterone is reduced by at least 50%. In some embodiments of the methods provided herein, the level of 17-hydroxyprogesterone is reduced by an amount of from about 10% to about 90%, about 15% to about 90%, about 20% to about 90%, about 25% to about 90%, about 30% to about 90%, about 35% to about 90%, about 40% to about 90%, about 50% to about 90%, about 55% to about 90%, or about 60% to about 90% from pre-administration levels.

In some embodiments, the level of 17-hydroxyprogesterone is reduced to a level within the range of 17-hydroxyprogesterone expected for a subject without CAH, i.e., less than 1,000 ng/dL or less than 200 ng/dL.

In some embodiments of the methods provided herein, the level of testosterone is reduced by at least about 10%, at least about 15%, at least about 20%, at least about 25%, at least about 30%, at least about 35%, at least about 40%, at least about 50%, at least about 55% or at least about 60% from pre-administration levels. In some embodiments, the level of testosterone is reduced by at least about 25%. In some embodiments, the level of testosterone is reduced by at least about 40%. In some embodiments, the level of testosterone is reduced by at least about 50%.

In some embodiments of the methods provided herein, the level of testosterone is reduced by an amount of from about 10% to about 90%, about 15% to about 90%, about 20% to about 90%, about 25% to about 90%, about 30% to about 90%, about 35% to about 90%, about 40% to about 90%, about 50% to about 90%, about 55% to about 90%, or about 60% to about 90% from pre-administration levels.

In some embodiments, the level of testosterone is reduced to a level within the range of testosterone expected for a subject without CAH.

In some embodiments of the methods provided herein, the level of androstenedione is reduced by at least about 10%, at least about 15%, at least about 20%, at least about 25%, at least about 30%, at least about 35%, at least about 40%, at least about 50%, at least about 55% or at least about 60% from pre-administration levels. In some embodiments, the level of androstenedione is reduced by at least about 25%. In some embodiments, the level of androstenedione is reduced by at least about 30%. In some embodiments, the level of androstenedione is reduced by at least about 50%.

In some embodiments of the methods provided herein, the level of androstenedione is reduced by an amount of from about 10% to about 90%, about 15% to about 90%, about 20% to about 90%, about 25% to about 90%, about 30% to about 90%, about 35% to about 90%, about 40% to about 90%, about 50% to about 90%, about 55% to about 90%, or about 60% to about 90% from pre-administration levels.

In some embodiments, the level of androstenedione is reduced to a level within the range of androstenedione expected for a subject without CAH, i.e., less than 200 ng/dL.

In some embodiments of the methods provided herein, the level of 17-hydroxyprogesterone is reduced by at least about 50% and the level of androstenedione is reduced by at least about 50% from pre-administration levels. In some embodiments of the methods provided herein, the level of 17-hydroxyprogesterone is reduced by at least about 50% and the level of androstenedione is reduced by at least about 30% from pre-administration levels.

Also provided herein are methods for reducing the severity of one or more symptoms selected from hirsutism, precocious puberty, fertility problems, acne, and growth impairment in a subject having classic congenital adrenal hyperplasia, comprising administering a compound of the invention, or a pharmaceutically acceptable salt thereof, in an amount sufficient to reduce one or more biomarker(s) of CAH in a subject, e.g., reduce the androstenedione in the subject. Growth impairment can refer to, e.g., accelerated height velocity, accelerated weight velocity, and/or accelerated bone age.

Provided herein are methods for reducing the level of one or more biomarker(s) in a subject having congenital adrenal hyperplasia comprising administering to the subject a compound of the invention, or a pharmaceutically acceptable salt thereof. In some embodiments, the one or more biomarker(s) are selected from (a) 17-hydroxyprogesterone (17-OHP); (b) testosterone; and (c) androstenedione. In some embodiments, the compound is a compound of formula (I), or a pharmaceutically acceptable salt thereof. In some embodiments, the compound is a compound of formula (Ia), or a pharmaceutically acceptable salt thereof. In some embodiments, the compound is a compound of formula (III), or a pharmaceutically acceptable salt thereof. In some embodiments, the compound is Compound 2, 4, or 5, or a pharmaceutically acceptable salt thereof. In some embodiments, the compound is Compound 6, 7, or 8, or a pharmaceutically acceptable salt thereof.

Provided herein are methods for reducing the level of one or more biomarker(s) in a subject having congenital adrenal hyperplasia comprising administering to the subject a pharmaceutical composition comprising a compound of the invention, or a pharmaceutically acceptable salt thereof; and at least one pharmaceutically acceptable excipient. In some embodiments, the one or more biomarker(s) are selected from (a) 17-hydroxyprogesterone (17-OHP); (b) testosterone; and (c) androstenedione. In some embodiments, the compound is a compound of formula (I), or a pharmaceutically acceptable salt thereof. In some embodiments, the compound is a compound of formula (Ia), or a pharmaceutically acceptable salt thereof. In some embodiments, the compound is a compound of formula (III), or a pharmaceutically acceptable salt thereof. In some embodiments, the compound is Compound 2, 4, or 5, or a pharmaceutically acceptable salt thereof. In some embodiments, the compound is Compound 6, 7, or 8, or a pharmaceutically acceptable salt thereof.

Provided herein are methods for reducing the dosage of corticosteroid administered to a subject having congenital adrenal hyperplasia for controlling congenital adrenal hyperplasia comprising administering to the subject a compound of the invention, or a pharmaceutically acceptable salt thereof. In some embodiments, the corticosteroid is a glucocorticoid. In some embodiments, the glucocorticoid is hydrocortisone, dexamethasone, prednisone, or prednisolone. In some embodiments, the corticosteroid is a mineralocorticoid. In some embodiments, the mineralocorticoid is fludrocortisone.

Provided herein are methods for reducing the dosage of corticosteroid administered to a subject having congenital adrenal hyperplasia for controlling congenital adrenal hyperplasia comprising administering to the subject a pharmaceutical composition comprising a compound of the invention, or a pharmaceutically acceptable salt thereof and at least one pharmaceutically acceptable excipient. In some embodiments, the compound is a compound of formula (I), or a pharmaceutically acceptable salt thereof. In some embodiments, the compound is a compound of formula (Ia), or a pharmaceutically acceptable salt thereof. In some embodiments, the compound is a compound of formula (III), or a pharmaceutically acceptable salt thereof. In some embodiments, the corticosteroid is a glucocorticoid. In some embodiments, the glucocorticoid is hydrocortisone, dexamethasone, prednisone, or prednisolone. In some embodiments, the corticosteroid is a mineralocorticoid. In some embodiments, the mineralocorticoid is fludrocortisone. In some embodiments, the compound is Compound 2, 4, or 5, or a pharmaceutically acceptable salt thereof. In some embodiments, the compound is Compound 6, 7, or 8, or a pharmaceutically acceptable salt thereof.

Also provided herein is a method of reducing the severity of one or more side effects of glucocorticoid treatment in a subject having congenital adrenal hyperplasia comprising administering to the subject a compound of the invention, or a pharmaceutically acceptable salt thereof. The long-term effects of glucocorticoid treatment are well documented in the art (see, e.g., Oray, M. et al. (2016): Long-term effect of glucocorticoids, *Expert Opinion on Drug Safety*. DOI: 10.1517/14740338.2016.1140743). Such side effects are associated with every biological system, e.g., musculoskeletal (e.g., osteoporosis, avascular necrosis of bone, and myopathy), endocrine and metabolic (e.g., hyperglycemia, diabetes mellitus, dyslipidemia, weight gain, Cushing syndrome, Cushingoid features, growth suppression, adrenal suppression), gastrointestinal (e.g., gastritis, peptic ulcer, gastrointestinal bleeding, visceral perforation, hepatic steatosis, pancreatitis), cardiovascular (e.g., hypertension, coronary heart disease, ischemic heart disease, heart failure), dermatologic (e.g., dermatoprosis, skin atrophy, ecchymosis, purpura, erosions, striae, delayed wound healing, easy bruising, acne, hirsutism, and hair loss), neuropsychiatric (e.g., mood changes, depression, euphoria, mood lability, irritability, akathisia, anxiety, cognitive impairment, psychosis, dementia, and delirium), ophthalmologic (e.g., cataract, glaucoma, ptosis, mydriasis, opportunistic ocular infections, and central serous chorioretinopathy), and immunologic (e.g., suppression of cell-mediated immunity, predisposition to infections, and reactivation of latent infections). In some embodiments, the compound is a compound of formula (I), or a pharmaceutically acceptable salt thereof. In some embodiments, the compound is a compound of formula (Ia), or a pharmaceutically acceptable salt thereof. In some embodiments, the compound is a compound of formula (III), or a pharmaceutically acceptable salt thereof. In some embodiments, the glucocorticoid is hydrocortisone, dexamethasone, prednisone, or prednisolone. In some embodiments, the compound is Compound 2, 4, or 5, or a pharmaceutically acceptable salt thereof. In some embodiments, the compound is Compound 6, 7, or 8, or a pharmaceutically acceptable salt thereof.

Also provided herein is a method of reducing the severity of one or more side effects of glucocorticoid treatment in a subject having congenital adrenal hyperplasia comprising administering to the subject a pharmaceutical composition comprising a compound of the invention, or a pharmaceutically acceptable salt thereof and at least one pharmaceutically acceptable excipient. In some embodiments, the compound is a compound of formula (I), or a pharmaceutically acceptable salt thereof. In some embodiments, the compound is a compound of formula (Ia), or a pharmaceutically acceptable salt thereof. In some embodiments, the compound is a compound of formula (III), or a pharmaceutically acceptable salt thereof. In some embodiments, the glucocorticoid is hydrocortisone, dexamethasone, prednisone, or prednisolone. In some embodiments, the compound is Compound 2, 4, or 5, or a pharmaceutically acceptable salt thereof. In some embodiments, the compound is Compound 6, 7, or 8, or a pharmaceutically acceptable salt thereof.

Accordingly, in some embodiments, the side effects of glucocorticoid treatment are selected from osteoporosis, avascular necrosis of bone, myopathy, hyperglycemia, diabetes mellitus, dyslipidemia, weight gain, Cushing syndrome, Cushingoid features, growth suppression, adrenal suppression, gastritis, peptic ulcer, gastrointestinal bleeding, visceral perforation, hepatic steatosis, pancreatitis, hypertension, coronary heart disease, ischemic heart disease, heart failure, dermatoprosis, skin atrophy, ecchymosis, purpura, erosions, striae, delayed wound healing, easy bruising, acne, hirsutism, hair loss, mood changes, depression, euphoria, mood lability, irritability, akathisia, anxiety, cognitive impairment, psychosis, dementia, delirium, cataract, glaucoma, ptosis, mydriasis, opportunistic ocular infections, central serous chorioretinopathy, suppression of cell-mediated immunity, predisposition to infections, reactivation of latent infections, and any combination thereof.

Provided herein are methods of treating congenital adrenal hyperplasia in a subject comprising
 (i) measuring the level of one or more biomarker(s) selected from (a) 17-hydroxyprogesterone (17-OHP); (b) testosterone; and (c) androstenedione in a biological sample obtained from the subject;
 (ii) analyzing the level of the one or more biomarker(s) measured in step (i) to determine if the level of the one or more biomarker(s) is elevated compared to a healthy subject not having congenital adrenal hyperplasia; and
 (iii) administering to the subject a compound of the invention, or a pharmaceutically acceptable salt thereof if the subject is determined to have elevated levels of the one or more biomarker(s).

In some embodiments, the method further comprises (iv) measuring the level of the one or more biomarker(s) after administering a compound of the invention, or a pharmaceutically acceptable salt thereof, in a biological sample obtained from the subject to determine whether the subject has reduced levels of the one or more biomarker(s) as compared with the measurement of step (i). In some embodiments, the method further comprises (v) continuing the administration of the compound of the invention, or a pharmaceutically acceptable salt thereof if the subject has reduced levels of the one or more biomarker(s).

In some embodiments, steps (i) and (iv) are performed on biological samples taken from the subject in a similar manner and within a same time of day window. In some embodiments, steps (i) and (iv) are performed on biological samples taken from the subject within the time of day window from 2 a.m. to 10 a.m. In some embodiments, steps (i) and (iv) are performed on biological samples taken from the subject within the time of day window from 6 a.m. to 10 a.m.

In some embodiments, steps (i) and (iv) comprise measuring the levels of at least two biomarkers selected from (a) 17-hydroxyprogesterone (17-OHP); (b) testosterone; and (c) androstenedione.

In some embodiments, steps (i) and (iv) comprise measuring the levels of (a) 17-hydroxyprogesterone (17-OHP); (b) testosterone; and (c) androstenedione.

In some embodiments, step (i) comprises measuring the level of 17-hydroxyprogesterone (17-OHP), wherein the level of 17-hydroxyprogesterone (17-OHP) is elevated when it is greater than or equal to 1,000 ng/dL.

In some embodiments, step (i) comprises measuring the level of androstenedione, wherein the level of androstenedione is elevated when it is greater than 200 ng/dL.

In some embodiments of the methods of the present disclosure, the compound of the invention, or a pharmaceutically acceptable salt thereof, is administered at an amount equivalent to from about 25 mg to about 150 mg of the free base compound. In some embodiments, the compound of the invention, or a pharmaceutically acceptable salt thereof, is administered at an amount equivalent to about 50 mg or about 100 mg of the free base compound.

In some embodiments of the methods disclosed herein, the compound of the invention is administered in the free base form.

In some embodiments of the methods disclosed herein, the compound of the invention, or a pharmaceutically acceptable salt thereof is administered once daily or twice daily.

In some embodiments of the methods disclosed herein, the compound is a compound of formula (I) or a pharmaceutically acceptable salt thereof. In some embodiments of the methods disclosed herein, the compound is a compound of formula (Ia) or a pharmaceutically acceptable salt thereof. In some embodiments of the methods disclosed herein, the compound is a compound of formula (III) or a pharmaceutically acceptable salt thereof.

In some embodiments of the methods disclosed herein, the compound of the invention is administered in a pharmaceutical composition comprising the compound, or a pharmaceutically acceptable salt thereof and at least one pharmaceutically acceptable excipient.

In some embodiments of the methods disclosed herein, the compound is a compound of formula (Ia) having the following structure:

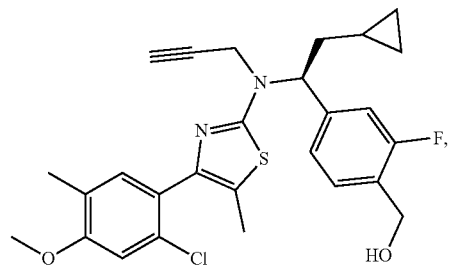

or a pharmaceutically acceptable salt thereof.

Some embodiments provide a method of treating congenital adrenal hyperplasia in a subject in need thereof comprising administering to the subject a therapeutically effective amount of (S)-{4-[1-{[4-(2-chloro-4-methoxy-5-methylphenyl)-5-methyl-1,3-thiazol-2-yl](prop-2-yn-1-yl)amino}-2-cyclopropylethyl]-2-fluorophenyl}methanol (Compound 2)

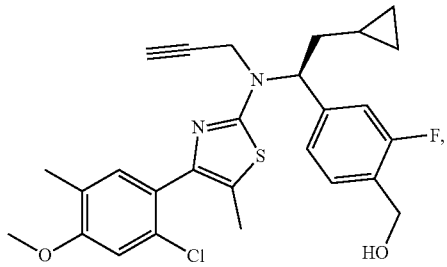 [SMILES: C#CCN(c1nc(-c2cc(C)c(OC)cc2Cl)c(C)s1)[C@@H](CC1CC1)c1ccc(CO)c(F)c1]

Compound 2 wherein Compound 2 is generated under physiological conditions or by solvolysis following administration to the subject of a prodrug of Compound 2, or a pharmaceutically acceptable salt thereof, wherein the prodrug of Compound 2, or the pharmaceutically acceptable salt thereof, is not 4-(2-chloro-4-methoxy-5-methylphenyl)-N-((1S)-2-cyclopropyl-1-(3-fluoro-4-methylphenyl)ethyl)-5-methyl-N-2-propyn-1-yl-2-thiazolamine, or a pharmaceutically salt thereof.

Some embodiments provide a method of treating congenital adrenal hyperplasia in a subject in need thereof comprising administering to the subject a therapeutically effective amount of (S)-{4-[1-{[4-(2-chloro-4-methoxy-5-methylphenyl)-5-methyl-1,3-thiazol-2-yl](prop-2-yn-1-yl)amino}-2-cyclopropylethyl]-2-fluorophenyl}methanol (Compound 2)

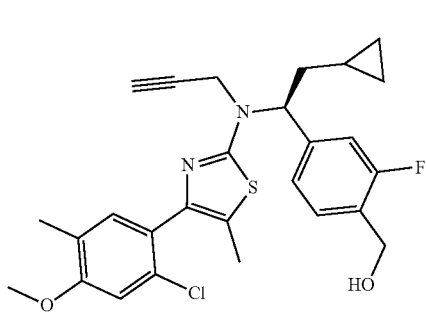

Compound 2 wherein Compound 2 is generated as a result of a metabolic chemical reaction following administration to the subject of a prodrug of Compound 2, or a pharmaceutically acceptable salt thereof, wherein the prodrug of Compound 2, or the pharmaceutically acceptable salt thereof, is not 4-(2-chloro-4-methoxy-5-methylphenyl)-N-((1S)-2-cyclopropyl-1-(3-fluoro-4-methylphenyl)ethyl)-5-methyl-N-2-propyn-1-yl-2-thiazolamine, or a pharmaceutically salt thereof.

Some embodiments provide a method of treating congenital adrenal hyperplasia in a subject in need thereof comprising administering to the subject a therapeutically effective amount of a prodrug of (S)-{4-[1-{[4-(2-chloro-4-methoxy-5-methylphenyl)-5-methyl-1,3-thiazol-2-yl](prop-2-yn-1-yl)amino}-2-cyclopropylethyl]-2-fluorophenyl}methanol (Compound 2)

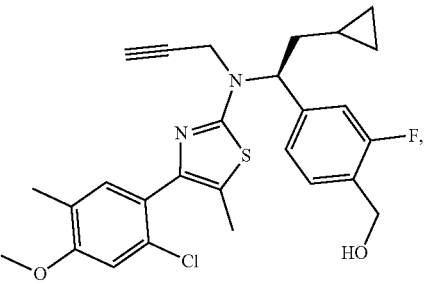 [SMILES: C#CCN(c1nc(-c2cc(C)c(OC)cc2Cl)c(C)s1)[C@@H](CC1CC1)c1ccc(CO)c(F)c1]

Compound 2 or a pharmaceutically acceptable salt thereof, wherein the prodrug of Compound 2, or the pharmaceutically acceptable salt thereof, is not 4-(2-chloro-4-methoxy-5-methylphenyl)-N-((1S)-2-cyclopropyl-1-(3-fluoro-4-methylphenyl)ethyl)-5-methyl-N-2-propyn-1-yl-2-thiazolamine, or a pharmaceutically salt thereof.

In some embodiments of the methods disclosed herein, the CAH is classic CAH. In some embodiments of the methods disclosed herein, the CAH is non-classic CAH.

As used herein, the term "subject" refers to any animal, including mammals, preferably mice, rats, other rodents, rabbits, dogs, cats, swine, cattle, sheep, horses, or primates, and most preferably humans. In the context of a clinical trial or screening or activity experiment the subject may be a healthy volunteer or healthy participant without an underlying $CRF_1$ mediated disorder or condition or a volunteer or participant that has received a diagnosis for a disorder or condition in need of medical treatment as determined by a health care professional. In the context outside of a clinical trial a subject under the care of a health care professional who has received a diagnosis for a disorder or condition is typically described as a patient. In some embodiments, the subject has experienced and/or exhibited at least one symptom of the disease or disorder to be treated and/or prevented. In some embodiments, the subject has been identified or diagnosed as having congenital adrenal hyperplasia (CAH). In some embodiments, the subject is suspected of having CAH. In some embodiments, the subject has a clinical record indicating that the subject has CAH (and optionally the clinical record indicates that the subject should be treated with any of the compositions provided herein). In some embodiments, the subject is a pediatric subject.

The term "pediatric subject" as used herein refers to a subject under the age of 21 years at the time of diagnosis or treatment. The term "pediatric" can be further divided into various subpopulations including: neonates (from birth through the first month of life); infants (1 month up to two years of age); children (two years of age up to 12 years of age); and adolescents (12 years of age through 21 years of age (up to, but not including, the twenty-second birthday)). Berhman et al., *Textbook of Pediatrics,* 15th Ed. Philadelphia: W.B. Saunders Company, 1996; Rudolph et al., *Rudolph's Pediatrics,* 21st Ed. New York: McGraw-Hill, 2002; and Avery et al., *Pediatric Medicine,* 2nd Ed. Baltimore: Williams & Wilkins; 1994. In some embodiments, a pediatric subject is from birth through the first 28 days of life, from 29 days of age to less than two years of age, from two years of age to less than 12 years of age, or 12 years of age through 21 years of age (up to, but not including, the twenty-second birthday). In some embodiments, a pediatric subject is from birth through the first 28 days of life, from 29 days of age to less than 1 year of age, from one month of age to less than four months of age, from three months of age to less than seven months of age, from six months of age to less than 1 year of age, from 1 year of age to less than 2 years of age, from 2 years of age to less than 3 years of age, from 2 years of age to less than seven years of age, from 3 years of age to less than 5 years of age, from 5 years of age to less than 10 years of age, from 6 years of age to less than 13 years of age, from 10 years of age to less than 15 years of age, or from 15 years of age to less than 22 years of age.

As used herein, the terms "treat" and "treatment" refer to medical management of a disease, disorder, or condition of a subject (i.e., patient) (see, e.g., Stedman's Medical Dictionary). In general, an appropriate dose and treatment regimen provide the $CRF_1$ antagonist in an amount sufficient to provide therapeutic and/or prophylactic benefit. Therapeutic benefit for subjects to whom the $CRF_1$ antagonist compound(s) described herein are administered, includes, for example, an improved clinical outcome, wherein the object is to prevent or slow or retard (lessen) an undesired physiological change associated with the disease, or to prevent or slow or retard (lessen) the expansion or severity of such disease. As discussed herein, effectiveness of the one or more $CRF_1$ antagonists may include beneficial or desired clinical results that comprise, but are not limited to, abatement, lessening, or alleviation of symptoms that result from or are associated with the disease to be treated; decreased occurrence of symptoms; improved quality of life; longer disease-free status (i.e., decreasing the likelihood or the propensity that a subject will present symptoms on the basis of which a diagnosis of a disease is made); diminishment of extent of disease; stabilized (i.e., not worsening) state of disease; delay or slowing of disease progression; amelioration or palliation of the disease state; and remission (whether partial or total), whether detectable or undetectable; and/or overall survival.

"Treatment" can also mean prolonging survival when compared to expected survival if a subject were not receiving treatment. Subjects in need of treatment include those who already have the disease or disorder as well as subjects prone to have or at risk of developing the disease or disorder, and those in which the disease, condition, or disorder is to be prevented (i.e., decreasing the likelihood of occurrence or recurrence of the disease or disorder).

The term "preventing," as used herein, means the prevention of the onset, recurrence or spread, in whole or in part, of the disease or condition as described herein, or a symptom thereof.

The term "administration" or "administering" refers to a method of giving a dosage of a compound or pharmaceutical formulation to a vertebrate or invertebrate, including a mammal, a bird, a fish, or an amphibian. The preferred method of administration can vary depending on various factors, e.g., the components of the pharmaceutical formulation, the site of the disease, and the severity of the disease.

As used herein, "therapeutically effective amount" is an amount of the compound of the invention, or a pharmaceutically acceptable salt thereof, or an amount of a pharmaceutical composition comprising the compound of the invention, or a pharmaceutically acceptable salt thereof, which is sufficient to achieve the desired effect and can vary according to the nature and severity of the disease condition, and the potency of the compound. A therapeutic effect is the relief, to some extent, of one or more of the symptoms of the disease, and can include curing a disease. "Curing" means that the symptoms of active disease are eliminated. However, certain long-term or permanent effects of the disease can exist even after a cure is obtained (such as, e.g., extensive tissue damage).

As used herein, "time of day window" refers to a period of time defined by a window start time and a window stop time. These times all refer to local times where a sample was taken. The phrase "same time of day window" when referring to samples taken from the subject mean, e.g., that a sample taken at 8:15 a.m. and a sample taken at 9:15 a.m. are considered to be taken in the same time of day window of, e.g., 2 a.m. to 10 a.m. or 6 a.m. to 10 a.m.

Various indicators for determining the effectiveness of a method for treating CAH are known to those skilled in the art. Examples of suitable indicators include, but are not limited to, a reduction in 17-OHP and androstenedione compared to non-treatment or reduction of amount of glucocorticoid (e.g., hydrocortisone, dexamethasone, prednisone, or prednisolone) administered per day.

In some embodiments, a compound of the invention, or a pharmaceutically acceptable salt thereof, can result in at least a 1, 2, 3, 4, 5, 10, 15, 20, 25, 50, 75, 100-fold or more decrease in 17-OHP plasma levels during 6 a.m. to 10 a.m. relative to pre-treatment levels in a subject, as determined after completion of the treatment regime (for example, 1 week after completion). In some embodiments, a compound of the invention, or a pharmaceutically acceptable salt thereof, can result in a decrease in androstenedione plasma levels during 6 a.m. to 10 a.m. relative to pre-treatment levels in the range of about 2 to about 5 fold, about 10 to about 20 fold, about 15 to about 40 fold, or about 50 to about 100 fold. In some embodiments, a compound of the invention, or a pharmaceutically acceptable salt thereof, can result in a decrease in testosterone plasma levels during 6 a.m. to 10 a.m. relative to pre-treatment levels in the range of 2 to 5 fold, 10 to 20 fold, 15 to 40 fold, or 50 to 100 fold. In some embodiments, administration of a compound of the invention, or a pharmaceutically acceptable salt thereof, can result in a decrease in glucocorticoid (e.g., hydrocortisone, dexamethasone, prednisone, or prednisolone) administered per day compared to the current standard of care for CAH, or may achieve the same plasma levels of at least one selected from 17-OHP, androstenedione and testosterone plasma levels during 6 a.m. to 10 a.m. as that of glucocorticoid (e.g., hydrocortisone, dexamethasone, prednisone, or prednisolone) monotherapy, as determined after completion of the treatment regime (for example, 1, 2, 3, 4, 5, 6, or 7 weeks after completion).

In some embodiments, a compound of the invention, or a pharmaceutically acceptable salt thereof, can decrease the percentage of subjects that experience complications from CAH compared to the percentage of subjects that experience complication being treated with glucocorticoids (e.g., hydrocortisone, dexamethasone, prednisone, or prednisolone) monotherapy. For example, the percentage of subjects being treated with a compound of the invention, or a pharmaceutically acceptable salt thereof, that experience complications can be 10%, 25%, 40%, 50%, 60%, 70%, 80% and 90% less compared to subjects being treated with glucocorticoids (e.g., hydrocortisone, dexamethasone, prednisone, or prednisolone).

In another embodiment, a method is provided for antagonizing $CRF_1$ in a cell comprising contacting the cell and a compound of the invention, or a pharmaceutically acceptable salt thereof, including specific compounds described herein, for a time sufficient and under appropriate conditions to permit interaction between the cell and the compound. In certain embodiments, the cell is in a subject who is in need of treatment with a compound disclosed herein.

Combination Therapies

The compounds of the invention, or pharmaceutically acceptable salts thereof, can be used in combination treatments where the compound of the invention, or a pharmaceutically acceptable salt thereof, is administered in conjunction with other treatments such as the administration of one or more additional therapeutic agents. The additional therapeutic agents are typically those which are normally used to treat the particular condition to be treated. The additional therapeutic agents can include, glucocorticoids (e.g., hydrocortisone, dexamethasone, prednisone, or prednisolone) or mineralocorticoids (e.g., fludrocortisone). Examples of additional therapeutic agents include, but are not limited to glucocorticoids (e.g., hydrocortisone, dexamethasone, prednisone, or prednisolone) and mineralocorticoids (e.g., fludrocortisone). Other treatments that can be administered in conjunction with compounds of the invention, or pharmaceutically acceptable salts thereof, include, but are not limited to surgical intervention.

A compound of the invention, or a pharmaceutically acceptable salt thereof, can be administered with one or more additional agent(s) together in a single pharmaceutical composition, or as two or more separate pharmaceutical compositions.

The order of administration of a compound of the invention, or a pharmaceutically acceptable salt thereof, can be administered concurrently with any/all additional agents, or sequentially with any/all additional agents, in either order (e.g., a compound of the invention, or a pharmaceutically acceptable salt thereof, can be administered before, or after, any/all additional agents).

Pharmaceutical Compositions, Formulation, and Dosage Forms

The present disclosure further provides for compositions comprising any of the compounds as disclosed and described herein (e.g., a compound of formula (I), formula (Ia), or formula (III)), including specific compounds described herein) or pharmaceutically acceptable salts thereof, and an excipient such as a pharmaceutically acceptable excipient for use in the methods for treating CAH. A pharmaceutically acceptable excipient is a physiologically and pharmaceutically suitable non-toxic and inactive material or ingredient that does not interfere with the activity of the drug substance; an excipient also may be called a carrier. The formulation methods and excipients described herein are exemplary and are in no way limiting. Pharmaceutically acceptable excipients are well known in the pharmaceutical art and described, for example, in Rowe et al., Handbook of Pharmaceutical Excipients: A Comprehensive Guide to Uses, Properties, and Safety, 5$^{th}$ Ed., 2006, and in *Remington: The Science and Practice of Pharmacy* (Gennaro, 21$^{st}$ Ed. Mack Pub. Co., Easton, PA (2005)). Exemplary pharmaceutically acceptable excipients include sterile saline and phosphate buffered saline at physiological pH. Preservatives, stabilizers, dyes, buffers, and the like may be provided in the pharmaceutical composition. In addition, antioxidants and suspending agents may also be used.

In some embodiments, the pharmaceutical composition comprises a compound of the invention or a pharmaceutically acceptable salt thereof. In some embodiments, the pharmaceutical composition comprises a compound of formula (Ia) or a pharmaceutically acceptable salt thereof. In some embodiments, the pharmaceutical composition comprises a compound of formula (I) or a pharmaceutically acceptable salt thereof. In some embodiments, the pharmaceutical composition comprises a compound of formula (III) or a pharmaceutically acceptable salt thereof. In some embodiments, the pharmaceutical composition comprises a preparation of a compound of formula (I) or a pharmaceutically acceptable salt thereof. In some embodiments, the pharmaceutical composition comprises a preparation of a compound of formula (Ia) or a pharmaceutically acceptable salt thereof. In some embodiments, the pharmaceutical composition comprises a preparation of a compound of formula (III) or a pharmaceutically acceptable salt thereof. In some embodiments, the pharmaceutical composition comprises a compound having the following structure:

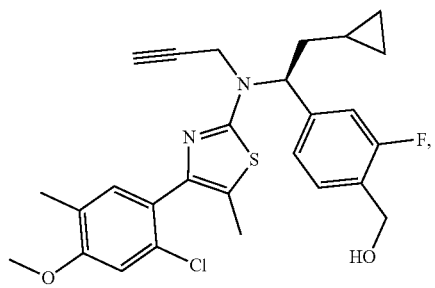

or a pharmaceutically acceptable salt thereof.

For compositions formulated as liquid solutions, acceptable carriers and/or diluents include saline and sterile water, and may optionally include antioxidants, buffers, bacteriostats and other common additives. The compositions can also be formulated as pills, capsules, granules, or tablets which contain, in addition to a CRF$_1$ antagonist, diluents, dispersing and surface active agents, binders, and lubricants. One skilled in this art may further formulate the CRF$_1$ antagonist in an appropriate manner, and in accordance with accepted practices, such as those disclosed in Remington, supra.

Methods of administration include systemic administration of a CRF$_1$ antagonist described herein, preferably in the form of a pharmaceutical composition as discussed above. As used herein, systemic administration includes oral and parenteral methods of administration. For oral administration, suitable pharmaceutical compositions include powders, granules, pills, tablets, and capsules as well as liquids, syrups, suspensions, and emulsions. These compositions may also include flavorants, preservatives, suspending, thickening and emulsifying agents, and other pharmaceutically acceptable additives. For parental administration, the compounds of the present invention can be prepared in aqueous injection solutions which may contain, in addition to the CRF$_1$ antagonist, buffers, antioxidants, bacteriostats, and other additives commonly employed in such solutions.

As described herein optimal doses are generally determined using experimental models and/or clinical trials. The optimal dose of the CRF$_1$ antagonist may depend upon the body mass, weight, blood volume, or other individual characteristics of the subject. For example, a person skilled in the medical art can consider the subject's condition, that is, stage of the disease, severity of symptoms caused by the disease, general health status, as well as age, gender, and weight, and other factors apparent to a person skilled in the medical art. In general, the amount of a compound described herein, that is present in a dose ranges from about 0.1 mg to about 2 mg per kg weight of the subject. In certain embodiments, a daily dose is about 10-150 mg. The use of the minimum dose that is sufficient to provide effective therapy is usually preferred. Subjects may generally be monitored for therapeutic effectiveness by clinical evaluation and using assays suitable for the condition being treated or prevented, which methods will be familiar to those having ordinary skill in the art and are described herein. The level of a compound that is administered to a subject may be monitored by determining the level of the compound in a biological fluid, for example, in the blood, blood fraction (e.g., plasma, serum), and/or in the urine, and/or other biological sample from the subject. Any method practiced in the art to detect the compound may be used to measure the level of compound during the course of a therapeutic regimen.

Pharmaceutical composition comprising a $CRF_1$ antagonist may formulated for timed release (also called extended release, sustained release, controlled release, or slow release). Such compositions may generally be prepared using well known technology and administered by, for example, oral, rectal or subcutaneous implantation, or by implantation at the desired target site. Sustained-release formulations may contain the compound dispersed in a carrier matrix and/or contained within a reservoir surrounded by a rate controlling membrane. Excipients for use within such formulations are biocompatible, and may also be biodegradable; preferably the formulation provides a relatively constant level of active component release. The amount of active compound contained within a sustained release formulation depends upon the site of implantation, the rate and expected duration of release, and the nature of the condition to be treated or prevented.

The pharmaceutical compositions described herein that comprise at least one of the $CRF_1$ antagonist compounds described herein may be administered to a subject in need by any one of several routes that effectively deliver an effective amount of the compound. Such administrative routes include, for example, oral, parenteral (e.g., subcutaneous, intravenous, intramuscular, intrasternal, intracavernous), enteral, rectal, intranasal, buccal, sublingual, intramuscular, and transdermal.

Pharmaceutical compositions for oral administration can be obtained by any suitable method, typically by uniformly mixing the compound(s) with liquids or finely divided solid carriers, or both, in the required proportions and then, if necessary, processing the mixture, after adding suitable auxiliaries, if desired, forming the resulting mixture into a desired shape to obtain tablets or dragee cores.

Conventional excipients, such as binding agents, fillers, adjuvant, carrier, acceptable wetting agents, tableting lubricants and disintegrants may be used in tablets and capsules for oral administration. Liquid compositions for oral administration may be in the form of solutions, emulsions, aqueous or oily suspensions and syrups. Alternatively, the oral compositions may be in the form of dry powder that can be reconstituted with water or another suitable liquid vehicle before use. Additional additives such as suspending or emulsifying agents, non-aqueous vehicles (including edible oils), preservatives and flavorings and colorants may be added to the liquid preparations. Parenteral dosage forms may be prepared by dissolving the compound of the invention in a suitable liquid vehicle and filter sterilizing the solution before lyophilization, or simply filling and sealing an appropriate vial or ampule.

As used herein, "drug substance", defined in the context of a "pharmaceutical composition", refers to a component of a pharmaceutical composition such as a compound of the invention (e.g., a compound of formula (I), formula (Ia), or formula (III)), including specific compounds described herein) and pharmaceutically acceptable salts thereof that provides the primary pharmacological effect, as opposed to an "inactive ingredient" which would generally be recognized as providing no therapeutic benefit.

As used herein, an "excipient" refers to a substance that is added to a composition to provide, without limitation, bulk, consistency, stability, binding ability, lubrication, disintegrating ability, etc., to the composition. A "diluent" is a type of excipient, and refers to an ingredient in a pharmaceutical composition that lacks pharmacological activity but may be pharmaceutically necessary or desirable. For example, a diluent may be used to increase the bulk of a potent drug whose mass is too small for manufacture and/or administration. It may also be a liquid for the dissolution of a drug to be administered by injection, ingestion, or inhalation. A pharmaceutically acceptable excipient is a physiologically and pharmaceutically suitable non-toxic and inactive material or ingredient that does not interfere with the activity of the drug substance. Pharmaceutically acceptable excipients are well known in the pharmaceutical art and described, for example, in Rowe et al., Handbook of Pharmaceutical Excipients: A Comprehensive Guide to Uses, Properties, and Safety, $5^{th}$ Ed., 2006, and in *Remington: The Science and Practice of Pharmacy* (Gennaro, $21^{st}$ Ed. Mack Pub. Co., Easton, PA (2005)). Preservatives, stabilizers, dyes, buffers, and the like may be provided in the pharmaceutical composition. In addition, antioxidants and suspending agents may also be used. For compositions formulated as liquid solutions, acceptable carriers and/or diluents include saline and sterile water, and may optionally include antioxidants, buffers, bacteriostats and other common additives. In some embodiments, the diluents may be a buffered aqueous solution such as, without limitation, phosphate buffered saline. The compositions can also be formulated as capsules, granules, or tablets which contain, in addition to a compound as disclosed and described herein, diluents, dispersing and surface active agents, binders, and lubricants. One skilled in this art may further formulate a compound as disclosed and described herein in an appropriate manner, and in accordance with accepted practices, such as those disclosed in Remington, supra.

In making pharmaceutical compositions comprising compounds of the invention, and pharmaceutically acceptable salts thereof, the drug substance is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier, or medium for the active ingredient. Thus, the compositions can be in the form of tablets, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

For preparing solid form pharmaceutical compositions such as powders, tablets, capsules, cachets, suppositories and dispersible granules an excipient can be one or more substances which may also act as diluents, flavoring agents, solubilizers, lubricants, suspending agents, binders, preservatives, tablet disintegrating agents, or an encapsulating material. Also included are solid form compositions which are intended to be converted, shortly before use, to liquid form preparations for oral administration. Such liquid forms include solutions, suspensions and emulsions. These compositions may contain, in addition to the drug substance, colorants, flavors, stabilizers, buffers, artificial and natural sweeteners, dispersants, thickeners, solubilizing agents and the like.

For preparing suppositories, a low melting wax, such as an admixture of fatty acid glycerides or cocoa butter, is first melted and the drug substance is dispersed homogeneously therein, as by stirring. The molten homogenous mixture is then poured into convenient sized molds, allowed to cool and thereby to solidify.

Formulations suitable for vaginal administration may be presented as pessaries, tampons, creams, gels, pastes, foams or sprays containing in addition to the drug substance such carriers as are known in the art to be appropriate.

Liquid form compositions include solutions, suspensions and emulsions, for example, water or water-propylene glycol solutions. For example, parenteral injection liquid compositions can be formulated as solutions in aqueous polyethylene glycol solution. Injectable compositions, for example, sterile injectable aqueous or oleaginous suspensions may be formulated according to the known art using suitable dispersing or wetting agents and suspending agents. The sterile injectable composition may also be a sterile injectable solution or suspension in a nontoxic parenterally acceptable diluent or solvent, for example, as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The pharmaceutical compositions may take such forms as suspensions, solutions, or emulsions in oily or aqueous vehicles and may contain formulatory agents such as suspending, stabilizing and/or dispersing agents. Alternatively, the pharmaceutical compositions may be in powder form, obtained by aseptic isolation of sterile solid or by lyophilization from solution, for constitution with a suitable vehicle, e.g. sterile, pyrogen-free water, before use.

The pharmaceutical compositions may be formulated as an aqueous solution, an aqua-alcoholic solution, a solid suspension, an emulsion, a liposomal suspension, or a freeze-dried powder for reconstitution. Such pharmaceutical compositions may be administered directly or as an admixture for further dilution/reconstitution. Route of administration includes intravenous bolus, intravenous infusion, irrigation, and instillation. Suitable solvents include water, alcohols, PEG, propylene glycol, and lipids; pH adjustments using an acid, e.g., HCl or citric acid, can be used to increase solubility and resulting compositions subjected to suitable sterilization procedures know in the art, such as, aseptic filtration. In some embodiments, the pH of the aqueous solution is about 2.0 to about 4.0. In some embodiments, the pH of the aqueous solution is about 2.5 to about 3.5.

Aqueous formulations suitable for oral use can be prepared by dissolving or suspending the drug substance in water and adding suitable colorants, flavors, stabilizing and thickening agents, as desired.

Aqueous suspensions suitable for oral use can be made by dispersing the finely divided drug substance in water with viscous material, such as natural or synthetic gums, resins, methylcellulose, sodium carboxymethylcellulose, or other well-known suspending agents.

For topical administration to the epidermis the compounds of the invention, and pharmaceutically acceptable salts thereof may be formulated as gels, ointments, creams or lotions, or as a transdermal patch. Also, formulations suitable for topical administration in the mouth include lozenges comprising drug substance in a flavored base, usually sucrose and acacia or tragacanth; pastilles comprising the drug substance in an inert base such as gelatin and glycerin or sucrose and acacia; and mouthwashes comprising the drug substance in a suitable liquid carrier. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. In some embodiments, topical formulations can contain one or more conventional carriers. In some embodiments, ointments can contain water and one or more hydrophobic carriers selected from, for example, liquid paraffin, polyoxyethylene alkyl ether, propylene glycol, white vaseline, and the like. Carrier compositions of creams can be based on water in combination with glycerol and one or more other components, e.g., glycerinemonostearate, PEG-glycerinemonostearate and cetylstearyl alcohol. Gels can be formulated using isopropyl alcohol and water, suitably in combination with other components such as, for example, glycerol, hydroxyethyl cellulose, and the like. In some embodiments, topical formulations contain at least 0.1, at least 0.25, at least 0.5, at least 1, at least 2, or at least 5 wt. % of a compound of the invention, or a pharmaceutically acceptable salt thereof.

Solutions or suspensions may be applied directly to the nasal cavity by conventional means, for example with a dropper, pipette or spray. The formulations may be provided in single or multi-dose form. In the latter case of a dropper or pipette, this may be achieved by the patient administering an appropriate, predetermined volume of the solution or suspension. In the case of a spray, this may be achieved for example by means of a metering atomizing spray pump.

Administration to the respiratory tract may also be achieved by means of an aerosol formulation in which the drug substance is provided in a pressurized pack with a suitable propellant. If the compounds of the invention, and pharmaceutically acceptable salts thereof, or pharmaceutical compositions comprising them, are administered as aerosols, for example as nasal aerosols or by inhalation, this can be carried out, for example, using a spray, a nebulizer, a pump nebulizer, an inhalation apparatus, a metered inhaler or a dry powder inhaler. Pharmaceutical forms for administration of the compounds of the present invention as an aerosol can be prepared by processes well known to the person skilled in the art. For their preparation, for example, solutions or dispersions of the compounds of the present invention in water, water/alcohol mixtures or suitable saline solutions can be employed using customary additives, for example benzyl alcohol or other suitable preservatives, absorption enhancers for increasing the bioavailability, solubilizers, dispersants and others and, if appropriate, customary propellants, for example include carbon dioxide, CFCs, such as, dichlorodifluoromethane, trichlorofluoromethane, or dichlorotetrafluoroethane; and the like. The aerosol may conveniently also contain a surfactant such as lecithin. The dose of drug may be controlled by provision of a metered valve.

Alternatively, the pharmaceutical composition may be provided in the form of a dry powder, for example, a powder mix of the compound in a suitable, powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

The compounds of the invention, and pharmaceutically acceptable salts thereof may also be administered via a rapid dissolving or a slow release composition, wherein the composition includes a biodegradable rapid dissolving or slow release carrier (such as a polymer carrier and the like) and a compound of the invention. Rapid dissolving or slow release carriers are well known in the art and are used to form complexes that capture therein an drug substance and either rapidly or slowly degrade/dissolve in a suitable environment (e.g., aqueous, acidic, basic, etc.).

The pharmaceutical compositions are preferably in unit dosage forms. In such form, the composition is subdivided into unit doses containing appropriate quantities of the drug substance. The unit dosage form can be a packaged composition, the package containing discrete quantities of composition, such as packeted tablets, capsules and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration are preferred compositions.

The compositions can be formulated in a unit dosage form, each dosage containing from 1 to 1,000 mg (1 g), more usually 5 mg to 200 mg, of the drug substance or equivalent mass of the drug substance. The term "unit dosage forms" refers to physically discrete units of a formulation suitable as unitary dosages for human subjects and other mammals, each unit containing a predetermined quantity of active material calculated to produce the desired therapeutic effect, in association with a suitable excipient, as described herein.

The compositions described herein can be formulated to provide immediate and/or timed release (also called extended release, sustained release, controlled release, or slow release) of the drug substance after administration to a subject by employing procedures known in the art. For example, the tablets including compounds of the invention, or pharmaceutically acceptable salts thereof, can be coated or otherwise compounded to provide a dosage form affording the advantage of prolonged action. For example, the tablet can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Pharmaceutical compositions comprising drug substance may formulated for timed release. Such compositions may generally be prepared using well known technology and administered by, for example, oral, rectal or subcutaneous implantation, or by implantation at the desired target site. Sustained-release formulations may contain the compound dispersed in a carrier matrix and/or contained within a reservoir surrounded by a rate controlling membrane. Excipients for use within such formulations are biocompatible, and may also be biodegradable; preferably the formulation provides a relatively constant level of active component release. The amount of drug substance contained within a sustained release formulation depends upon the site of implantation, the rate and expected duration of release, and the nature of the condition to be treated or prevented.

The liquid forms including the drug substance can be incorporated for administration orally or by injection include aqueous solutions, suitably flavored syrups, aqueous or oil suspensions, and flavored emulsions with edible oils such as cottonseed oil, sesame oil, coconut oil, or peanut oil, and similar excipients.

The pharmaceutical compositions described herein can be sterilized by conventional sterilization techniques, or may be sterile filtered. Aqueous solutions can be packaged for use as is, or lyophilized, the lyophilized preparation being combined with a sterile aqueous carrier prior to administration. The pH of the compositions is typically between 3 and 11, more preferably from 5 to 9 and most preferably from 7 to 8. It will be understood that use of certain of the foregoing excipients may result in the formation of pharmaceutically acceptable salts.

Compositions for inhalation or insufflation include solutions and suspensions in pharmaceutically acceptable, aqueous or organic solvents, or mixtures thereof, and powders. The liquid or solid compositions may contain suitable excipients as described herein. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The compositions may, if desired, be presented in a pack or dispenser device which may contain one or more unit dosage forms containing the drug substance. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions that can include a compound described herein formulated in a compatible pharmaceutical carrier may also be prepared, placed in an appropriate container, and labeled for treatment of an indicated condition.

As used herein, a "dose" or "dosage" means the measured quantity of drug substance to be taken at one time by a patient. In certain embodiments, wherein the drug substance is not a free base or free acid, the quantity is the molar equivalent to the corresponding amount of free base or free acid.

For preparing solid compositions such as tablets, the drug substance may be mixed with an excipient to form a solid preformulation composition containing a homogeneous mixture of components. When referring to these preformulation compositions as homogeneous, the drug substance is typically dispersed evenly throughout the composition so that the composition can be readily subdivided into equally effective unit dosage forms such as tablets and capsules. This solid preformulation is then subdivided into unit dosage forms of the type described above containing from, for example, 0.001 mg to 5000 mg of the drug substance. In certain embodiments, wherein the drug substance is not a free base or free acid of a compound of the invention, such as a salt or hydrate, the unit dosage form quantity is 0.001 mg to 5000 mg of the molar equivalent to the corresponding amount of free base or free acid of compound of the invention. Representative amounts of the drug substance in a unit dosage form include, but are not limited to, 0.01 mg, 0.1 mg, 0.2 mg, 0.4 mg, 0.6 mg, 0.8 mg, 1 mg, 2 mg, 4 mg, 6 mg, 8 mg, 10 mg, 12 mg, 14 mg, 16 mg, 18 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 150 mg, 200 mg, 250 mg, 300 mg, 400 mg, 500 mg, 600 mg, 700 mg, 800 mg, 900 mg, 1000 mg, 1500 mg, 2000 mg, 2500 mg, 3000 mg, 3500 mg, 4000 mg, 4500 mg, 5000 mg or an amount within a range defined by any of the preceding amounts. In certain embodiments, wherein the drug substance is not a free base or free acid, the drug substance corresponding to a molar equivalent amount of free base or free acid in a unit dosage form include, but are not limited to, 0.01 mg, 0.1 mg, 0.2 mg, 0.4 mg, 0.6 mg, 0.8 mg, 1 mg, 2 mg, 4 mg, 6 mg, 8 mg, 10 mg, 12 mg, 14 mg, 16 mg, 18 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 150 mg, 200 mg, 250 mg, 300 mg, 400 mg, 500 mg, 600 mg, 700 mg, 800 mg, 900 mg, 1000 mg, 1500 mg, 2000 mg, 2500 mg, 3000 mg, 3500 mg, 4000 mg, 4500 mg, 5000 mg or an amount within a range defined by any of the preceding amounts.

Multiple doses may be administered during the day, especially when relatively large amounts are deemed to be needed, for example 2, 3 or 4 doses. Depending on the individual and as deemed appropriate from the patient's physician or caregiver it may be necessary to deviate upward or downward from the doses described herein.

The amount of drug substance required for use in treatment will vary not only with the particular salt selected but also with the route of administration, the nature of the condition being treated and the age and condition of the patient and will ultimately be at the discretion of the attendant physician or clinician. In general, one skilled in the art understands how to extrapolate in vivo data obtained in a model system, typically an animal model, to another, such as a human. In some circumstances, these extrapolations may merely be based on the weight of the animal model in comparison to another, such as a mammal, preferably a human, however, more often, these extrapolations are not simply based on weights, but rather incorporate a variety of factors. Representative factors include the type, age, weight, sex, diet and medical condition of the patient, the severity of the disease, the route of administration, pharmacological considerations such as the activity, efficacy, pharmacokinetic and toxicology profiles of the particular compound employed, whether a drug delivery system is utilized, on whether an acute or chronic disease state is being treated or prophylaxis conducted or on whether further active compounds are administered in addition to the compounds described herein and as part of a drug combination. The dosage regimen for treating a disease condition with the compounds and/or compositions described herein is selected in accordance with a variety factors as cited above. Thus, the actual dosage regimen employed may vary widely and therefore may deviate from a preferred dosage regimen and one skilled in the art will recognize that dosage and dosage regimen outside these typical ranges can be tested and, where appropriate, may be used in the methods described herein.

As described herein optimal doses are generally determined using experimental models and/or clinical trials. The optimal dose of a compound as disclosed and described herein may depend upon the body mass, weight, blood volume, or other individual characteristics of the subject. For example, a person skilled in the medical art can consider the subject's condition, that is, stage of the disease, severity of symptoms caused by the disease, general health status, as well as age, gender, and weight, and other factors apparent to a person skilled in the medical art. In general, the amount of a compound described herein, that is present in a dose ranges from about 0.1 mg to about 2 mg per kg weight of the subject. In certain embodiments, a daily dose is about 10-150 mg. The use of the minimum dose that is sufficient to provide effective therapy is usually preferred. Subjects may generally be monitored for therapeutic effectiveness by clinical evaluation and using assays suitable for the condition being treated or prevented, which methods will be familiar to those having ordinary skill in the art and are described herein. The level of a compound that is administered to a subject may be monitored by determining the level of the compound in a biological fluid, for example, in the blood, blood fraction (e.g., plasma, serum), and/or in the urine, and/or other biological sample from the subject. Any method practiced in the art to detect the compound may be used to measure the level of compound during the course of a therapeutic regimen.

Kits with unit doses of one or more of the compounds described herein, usually in oral or injectable doses, are provided. Such kits may include a container containing the unit dose, an informational package insert describing the use and attendant benefits of the drugs in treating pathological condition of interest, and optionally an appliance or device for delivery of the composition.

Dosing Schedule/Amount

A compound of the invention, or a pharmaceutically acceptable salt thereof, may be effective over a wide dosage range and is generally administered in a therapeutically effective amount. It will be understood, however, that the amount of the compound actually administered will usually be determined by a physician, according to the relevant circumstances, including the condition to be treated, the chosen route of administration, the actual compound administered, the age, weight, and response of the individual subject, the severity of the subject's symptoms, and the like.

The amount of compound or composition administered to a subject will also vary depending upon what is being administered, the purpose of the administration, such as prophylaxis or therapy, the state of the subject, the manner of administration, and the like. In therapeutic applications, compositions can be administered to a subject already suffering from a disease in an amount sufficient to cure or at least partially arrest the symptomology and/or pathology of the disease and its complications. Therapeutically effective doses will depend on the disease condition being treated as well as by the judgment of the attending clinician depending upon factors such as the severity of the disease, the age, weight and general condition of the subject, and the like.

Some typical dosage ranges are from 1 μg/kg to 1 g/kg of body weight per day of the drug substance or equivalent mass of the drug substance when administered in a form such as a salt or hydrate. In some embodiments, the dose range is from about 0.01 mg/kg to about 100 mg/kg of body weight per day of the drug substance or equivalent mass of the drug substance. Representative amounts in a dose of the drug substance include, but are not limited to, 0.01 mg/kg, 0.1 mg/kg, 0.2 mg/kg, 0.4 mg/kg, 0.6 mg/kg, 0.8 mg/kg, 1 mg/kg, 2 mg/kg, 4 mg/kg, 6 mg/kg, 8 mg/kg, 10 mg/kg, 12 mg/kg, 14 mg/kg, 16 mg/kg, 18 mg/kg, 20 mg/kg, 25 mg/kg, 30 mg/kg, 35 mg/kg, 40 mg/kg, 45 mg/kg, 50 mg/kg, 55 mg/kg, 60 mg/kg, 65 mg/kg, 70 mg/kg, 75 mg/kg, 80 mg/kg, 85 mg/kg, 90 mg/kg, 95 mg/kg, 100 mg/kg, or an amount within a range defined by any of the preceding amounts of body weight per day. In certain embodiments, wherein the drug substance is not a free base or free acid of a compound of the invention, such as a salt or hydrate, the drug substance corresponding molar equivalent amount of free base or free acid of a compound of the invention in a unit dosage form include, but are not limited to, 0.01 mg/kg, 0.1 mg/kg, 0.2 mg/kg, 0.4 mg/kg, 0.6 mg/kg, 0.8 mg/kg, 1 mg/kg, 2 mg/kg, 4 mg/kg, 6 mg/kg, 8 mg/kg, 10 mg/kg, 12 mg/kg, 14 mg/kg, 16 mg/kg, 18 mg/kg, 20 mg/kg, 25 mg/kg, 30 mg/kg, 35 mg/kg, 40 mg/kg, 45 mg/kg, 50 mg/kg, 55 mg/kg, 60 mg/kg, 65 mg/kg, 70 mg/kg, 75 mg/kg, 80 mg/kg, 85 mg/kg, 90 mg/kg, 95 mg/kg, 100 mg/kg, or an amount within a range defined by any of the preceding amounts of body weight per day.

The dosage may be a single one or a series of two or more given in the course of one or more days, as is needed by the subject. In some embodiments, the compounds will be administered for a period of continuous therapy, for example for a week or more, or for months or years. Effective doses can be extrapolated from dose-response curves derived from in vitro or animal model test systems, as well as human clinical trials.

In instances where human dosages for compounds have been established for at least some condition, those same dosages may be used, or dosages that are between 0.1% and 500%, more preferably between about 25% and 250% of the established human dosage. Where no human dosage is established, as will be the case for newly-discovered pharmaceutical compositions, a suitable human dosage can be inferred from $ED_{50}$ or values, or other appropriate values derived from in vitro or in vivo studies, as qualified by toxicity studies and efficacy studies in animals.

In cases of administration of a pharmaceutically acceptable salt, dosages may be calculated as the free form (e.g. free base or free acid). Often a drug is packaged in a salt form and the dosage form strength refers to the mass of this salt form or the equivalent mass of the corresponding free base or free acid. As will be understood by those of skill in the art, in certain situations it may be necessary to administer the compounds disclosed herein in amounts that exceed, or even far exceed, the above-stated, preferred dosage range in order to effectively and aggressively treat particularly aggressive diseases or infections.

Dosage amount and interval may be adjusted individually to provide plasma levels of the active moiety which are sufficient to maintain the modulating effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations. Dosage intervals can also be determined using MEC value. Compositions should be administered using a regimen which maintains plasma levels above the MEC for 10-90% of the time, preferably between 30-90% and most preferably between 50-90%. In cases of local administration or selective uptake, the effective local concentration of the drug may not be related to plasma concentration.

Compounds disclosed herein can be evaluated for efficacy and toxicity using known methods. For example, the toxicology of a particular compound, or of a subset of the compounds, sharing certain chemical moieties, may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, or monkeys, may be determined using known methods. The efficacy of a particular compound may be established using several recognized methods, such as in vitro methods, animal models, or human clinical trials. When selecting a model to determine efficacy, the skilled artisan can be guided by the state of the art to choose an appropriate model, dose, route of administration and/or regime.

It will be apparent to those skilled in the art that the dosage forms described herein may comprise, as the drug substance, either a compound described herein or pharmaceutically acceptable salt thereof. Moreover, various hydrates and solvates of the compounds described herein and their salts can find use as intermediates in the manufacture of pharmaceutical compositions. Typical procedures for making and identifying suitable hydrates and solvates, outside those mentioned herein, are well known to those in the art; see for example, pages 202-209 of K. J. Guillory, "Generation of Polymorphs, Hydrates, Solvates, and Amorphous Solids," in: Polymorphism in Pharmaceutical Solids, ed. Harry G. Britain, Vol. 95, Marcel Dekker, Inc., New York, 1999 which is incorporated herein by reference in its entirety. Accordingly, one aspect of the present invention pertains to methods of administering hydrates and solvates of compounds described herein and/or their pharmaceutical acceptable salts, that can be isolated and characterized by methods known in the art, such as, thermogravimetric analysis (TGA), TGA-mass spectroscopy, TGA-Infrared spectroscopy, powder X-ray diffraction (PXRD), Karl Fisher titration, high resolution X-ray diffraction, and the like.

Compound Synthesis

Detailed compound synthesis methods are described herein in the Examples. A person having ordinary skill in the chemical art would be able to make a compound of the disclosure, including specific compounds described herein, by these methods or similar methods or other methods practiced by a person skilled in the art.

In general, the compounds used in the reactions described herein may be made according to organic synthesis techniques known to those skilled in this art, starting from commercially available chemicals and/or from compounds described in the chemical literature. "Commercially available chemicals" may be obtained from standard commercial sources including Acros Organics (Pittsburgh PA), Aldrich Chemical (Milwaukee WI, including Sigma Chemical and Fluka), Apin Chemicals Ltd. (Milton Park UK), Avocado Research (Lancashire U.K.), BDH Inc. (Toronto, Canada), Bionet (Cornwall, U.K.), Chemservice Inc. (West Chester PA), Crescent Chemical Co. (Hauppauge NY), Eastman Organic Chemicals, Eastman Kodak Company (Rochester NY), Fisher Scientific Co. (Pittsburgh PA), Fisons Chemicals (Leicestershire UK), Frontier Scientific (Logan UT), ICN Biomedicals, Inc. (Costa Mesa CA), Key Organics (Cornwall U.K.), Lancaster Synthesis (Windham NH), Maybridge Chemical Co. Ltd. (Cornwall U.K.), Parish Chemical Co. (Orem UT), Pfaltz & Bauer, Inc. (Waterbury CT), Polyorganix (Houston TX), Pierce Chemical Co. (Rockford IL), Riedel de Haen AG (Hanover, Germany), Spectrum Quality Product, Inc. (New Brunswick, NJ), TCI America (Portland OR), Trans World Chemicals, Inc. (Rockville MD), and Wako Chemicals USA, Inc. (Richmond VA).

Methods known to one of ordinary skill in the art may be identified through various reference books and databases. Suitable reference books and treatise that detail the synthesis of reactants useful in the preparation of compounds of the present disclosure, or provide references to articles that describe the preparation, include for example, "Synthetic Organic Chemistry," John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure," 4th Ed., Wiley-Interscience, New York, 1992. Additional suitable reference books and treatise that detail the synthesis of reactants useful in the preparation of compounds of the present disclosure, or provide references to articles that describe the preparation, include for example, Fuhrhop, J. and Penzlin G. "Organic Synthesis: Concepts, Methods, Starting Materials", Second, Revised and Enlarged Edition (1994) John Wiley & Sons ISBN: 3-527-29074-5; Hoffman, R. V. "Organic Chemistry, An Intermediate Text" (1996) Oxford University Press, ISBN 0-19-509618-5; Larock, R. C. "Comprehensive Organic Transformations: A Guide to Functional Group Preparations" 2nd Edition (1999) Wiley-VCH, ISBN: 0-471-19031-4; March, J. "Advanced Organic Chemistry: Reactions, Mechanisms, and Structure" 4th Edition (1992) John Wiley & Sons, ISBN: 0-471-60180-2; Otera, J. (editor) "Modern Carbonyl Chemistry" (2000) Wiley-VCH, ISBN: 3-527-29871-1; Patai, S. "Patai's 1992 Guide to the Chemistry of Functional Groups" (1992) Interscience ISBN: 0-471-93022-9; Quin, L. D. et al. "A Guide to Organophosphorus Chemistry" (2000) Wiley-Interscience, ISBN: 0-471-31824-8; Solomons, T. W. G. "Organic Chemistry" 7th Edition (2000) John Wiley & Sons, ISBN: 0-471-19095-0; Stowell, J. C., "Intermediate Organic Chemistry" 2nd Edition (1993) Wiley-Interscience, ISBN: 0-471-57456-2; "Industrial Organic Chemicals: Starting Materials and Intermediates: An Ullmann's Encyclopedia" (1999) John Wiley & Sons, ISBN: 3-527-29645-X, in 8 volumes; "Organic Reactions" (1942-2019) John Wiley & Sons, in over 95 volumes; and "Chemistry of Functional Groups" John Wiley & Sons, in hardcover volumes (86) and electronic volumes (26).

Specific and analogous reactants may also be identified through the indices of known chemicals prepared by the Chemical Abstract Service of the American Chemical Society, which are available in most public and university libraries, as well as through on-line databases (the American Chemical Society, Washington, D.C., may be contacted for more details). Chemicals that are known but not commercially available in catalogs may be prepared by custom chemical synthesis houses according to known methods, where many of the standard chemical supply houses (e.g., those listed above) provide custom synthesis services.

Abbreviations

The specification includes numerous abbreviations, whose definitions are listed in the following Table:

| Abbreviation | Definition |
| --- | --- |
| ACN | Acetonitrile |
| AcOEt | Ethyl acetate |
| CELITE ® | Diatomaceous earth |
| DCM | Di chloromethane or methylene chloride |

-continued

| Abbreviation | Definition |
| --- | --- |
| de | Diastereomeric excess |
| DIPEA | N,N-Diisopropylethylamine |
| DMF | N,N-Dimethylform amide |
| DMSO-$d_6$ | Dimethylsulfoxide-$d_6$ |
| d.r. | Diastereomeric ratio |
| ee | Enantiomeric excess |
| equiv. | Equivalent(s) |
| EtOH | Ethanol |
| H or hr | Hour(s) |
| HPLC | High-performance liquid chromatography |
| IPA | Isopropyl alcohol |
| LCMS | Liquid chromatography-mass spectrometry |
| MeOH | Methanol |
| min. | Minute(s) |
| mmol | Millimole(s) |
| MOM | Methoxymethyl |
| MOMCl | Methoxymethyl chloride |
| MTBE | Methyl tert-butyl ether |
| NaB(CN)$H_3$ | Sodium cyanoborohydride |
| $NH_4Cl$ | Ammonium chloride |
| $NH_4OAc$ | Ammonium acetate |
| Pd/C | Palladium on activated carbon |
| PTSA | p-Toluenesulfonic acid |
| quant. | Quantitative |
| rt | Room temperature |
| satd. | Saturated |
| TBAB | Tetra-n-butyl ammonium bromide |
| TBAF | Tetra-n-butylammonium fluoride |
| TBDMS | tert-Butyldimethylsilyl |
| THF | Tetrahydrofuran |

EXAMPLES

The following examples are included to demonstrate embodiments of the disclosure. However, those of skill in the art should, in light of the present disclosure, appreciate that many changes can be made in the specific embodiments which are disclosed and still obtain a like or similar result without departing from the spirit and scope of the disclosure.

Example 1

Preparation of racemic {4-[1-{[4-(2-chloro-4-methoxy-5-methylphenyl)-5-methyl-1,3-thiazol-2-yl](prop-2-yn-1-yl)amino}-2-cyclopropylethyl]-2-fluorophenyl}methanol (Compound 1)

The preparation of racemic {4-[1-{[4-(2-chloro-4-methoxy-5-methylphenyl)-5-methyl-1,3-thiazol-2-yl](prop-2-yn-1-yl)amino}-2-cyclopropylethyl]-2-fluorophenyl}methanol (Compound 1) is shown in Scheme 1:

Scheme 1

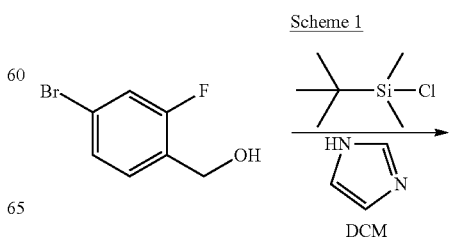

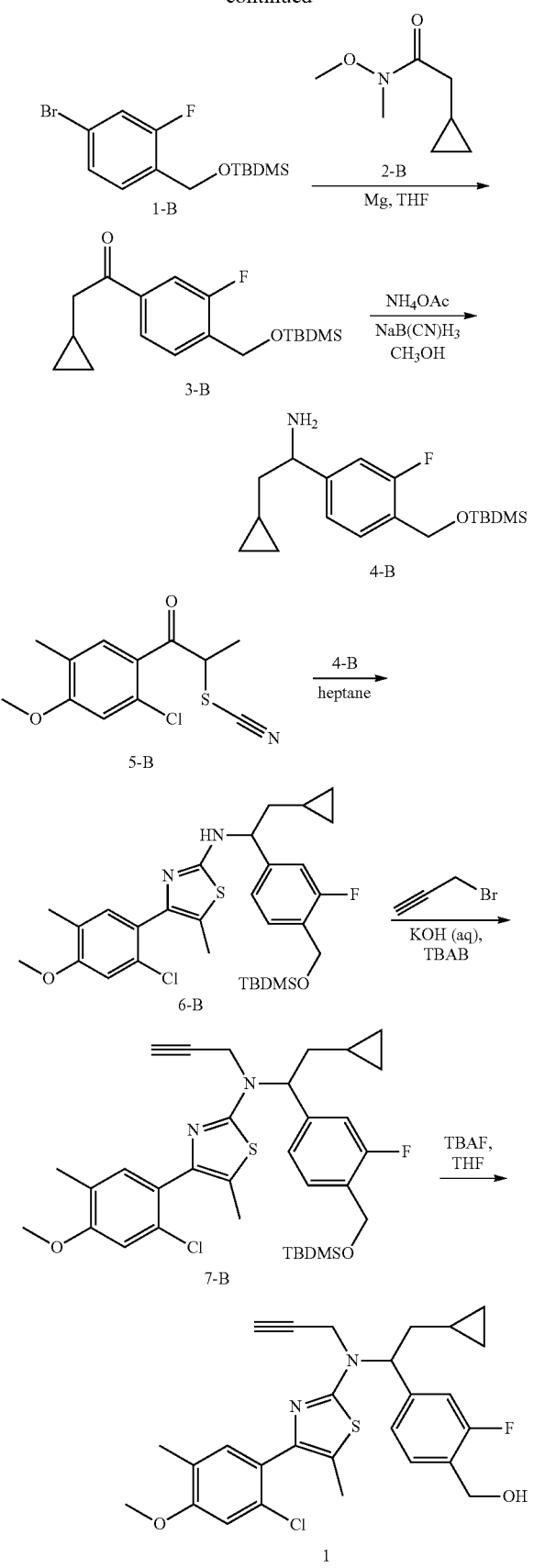

Step 1: Preparation of ((4-bromo-2-fluorobenzyl)oxy)(tert-butyl)dimethylsilane (Compound 1-B)

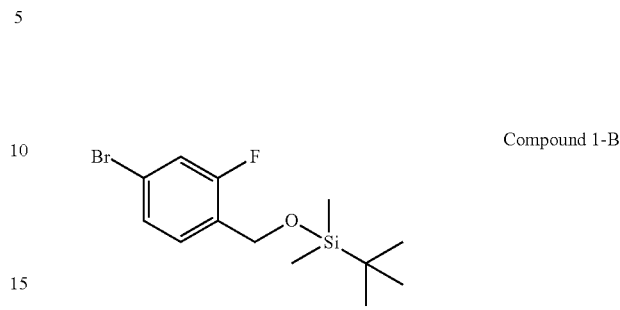

A mixture of (4-bromo-2-fluorophenyl)methanol (20 g, 98 mmol) and imidazole (7.31 g, 107 mmol) in methylene chloride (100 mL) was treated with tert-butyldimethyl silyl chloride (16.17 g, 107 mmol) in methylene chloride (100 mL) over 10 min. at rt. A white precipitate immediately formed which was removed by filtration. The filtrate was concentrated under reduced pressure and the remainder dissolved in heptane (100 mL). The organic phase was washed with water (2×40 mL), brine (2×40 mL), dried over $NaSO_4$ and concentrated under reduced pressure. The remainder was dissolved in c-hexane and passed through a silica pad (100 g) and then the solvent was removed under reduced pressure to afford Compound 1-B as a yellowish oil (30.51 g, 98% yield). $^1H$ NMR (400 MHz, $CDCl_3$) δ ppm 0.12 (s, 6H), 0.95 (s, 9H), 4.74 (s, 2H), 7.14-7.22 (m, 1H), 7.28-7.32 (m, 1H), 7.34-7.42 (m, 1H).

Step 2: Preparation of 1-(4-(((tert-butyldimethylsilyl)oxy)methyl)-3-fluorophenyl)-2-cyclopropyl-ethan-1-one (Compound 3-B)

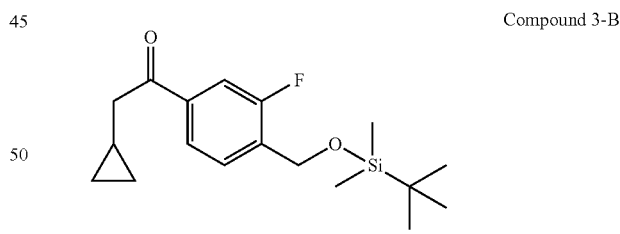

Magnesium turnings (2.34 g, 97 mmol, 1.38 equiv.) were suspended in anhydrous THF (39 mL). The mixture was maintained at 35° C. with stirring and treated with diisobutylaluminum hydride (1 M in heptane, 201 mL, 0.03 equiv.). The resulting mixture was treated with a small portion of ((4-bromo-2-fluorobenzyl)oxy)(tert-butyl)dimethylsilane (1-B, 3.01 g, 9.4 mmol, 0.1 wt. % of total) and the resulting suspension was stirred for 15 min. The remaining ((4-bromo-2-fluorobenzyl)oxy)(tert-butyl)dimethylsilane (1-B, 27.09 g, 84.6 mmol, 0.9 wt. % of total) was dissolved in THF (81 mL) and the resultant was added to the previously prepared suspension over an hr. The resulting mixture was heated to 40° C. and stirred for 3 h. Subsequently, the Grignard suspension was cooled to 15° C. and then treated with 2-cyclopropyl-N-methoxy-N-methylacetamide (2-B, 10 g, 70 mmol) in THF (60.2 mL) over 50 minutes. The resulting mixture was stirred at 20° C. for 2 h and then cooled to 5° C. and treated with 3N HCl (60.2 mL) over 30 min. at a rate to keep the internal temperature below 20° C. After addition was complete, the mixture was stirred at 20° C. for 2 h. The mixture was allowed to stand overnight to consume any residual magnesium. The mixture was combined with heptane (120 mL) and the layers partitioned. The organic layer was washed with satd. aq. NaHCO$_3$ (30 mL) and brine (30 mL), dried over Na$_2$SO$_4$, and filtered to remove solids. The solvent was removed under reduced pressure and the crude was passed though silica gel pad (100 g) eluting with c-hexane/AcOEt (98:2). The solvent was removed under reduced pressure to afford a mixture of Compound 3-B (16.5 g, 73% corrected) and desbromo compound (3.7 g), used in the next step without separation. $^1$H NMR (400 MHz, CDCl$_3$) δ ppm −0.01-0.34 (m, 10H), 0.52-0.70 (m, 2H), 0.91-1.06 (m, 12H), 1.07-1.24 (m, 1H), 2.86 (d, J=7.03 Hz, 2H), 4.81 (s, 1H), 4.85 (s, 2H), 6.92-7.05 (m, 1H), 7.11-7.18 (m, 1H), 7.19-7.26 (m, 1H), 7.44-7.54 (m, 1H), 7.56-7.66 (m, 2H), 7.74 (dd, J=7.90, 1.32 Hz, 1H) residual desbromo compound present.

Step 3: Preparation of 1-(4-(((tert-butyldimethylsilyl)oxy)methyl)-3-fluorophenyl)-2-cyclopropyl-ethan-1-amine (Compound 4-B)

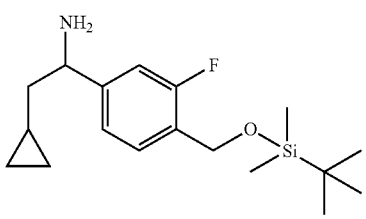

Compound 4-B

A mixture of 1-(4-(((tert-butyldimethylsilyl)oxy)methyl)-3-fluorophenyl)-2-cyclopropylethan-1-one (3-B, 10 g, 31 mmol, 1 equiv.) and ammonium acetate (11.95 g, 155 mmol, 5 equiv.) in methanol (50 mL) was stirred for 3 min. and then treated with sodium cyanoborohydride (2.92 g, 47 mmol). The resulting mixture was stirred at rt for 30 min. and then heated to 50° C. and stirred overnight. The solvent was removed under reduced pressure and the remainder combined with 2 M NaOH (50 mL). The resulting aqueous mixture was extracted with methyl tert-butyl ether (2×100 mL). The combined organic layers were dried over Na$_2$SO$_4$, filtered and concentrated under reduced pressure to give Compound 4-B as a waxy solid (10.4 g, assumed quant.). $^1$H NMR (400 MHz, DMSO-d$_6$) δ −0.03 (m, 2H), 0.08 (s, 13H), 0.20-0.43 (m, 4H), 0.77-0.97 (m, 19H), 1.10 (s, 3H), 1.51 (d, J=5.71 Hz, 3H), 4.00 (t, J=6.81 Hz, 1H), 4.70-4.74 (m, 3H), 6.88-7.13 (m, 1H), 6.88-7.11 (m, 1H), 7.13-7.24 (m, 2H), 7.30-7.46 (m, 2H) residual desbromo compound present.

Step 4: Preparation of N-(1-(4-(((tert-butyldimethylsilyl)oxy)methyl)-3-fluorophenyl)-2-cyclopropylethyl)-4-(2-chloro-4-methoxy-5-methylphenyl)-5-methylthiazol-2-amine (Compound 6-B)

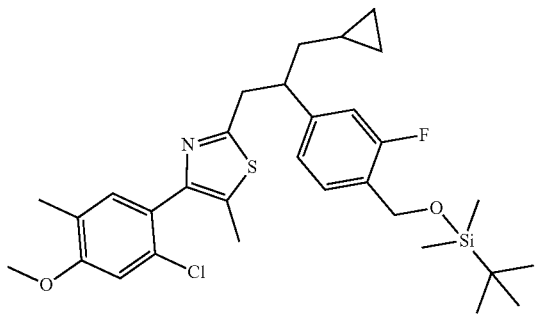

Compound 6-B

A suspension of 1-(2-chloro-4-methoxy-5-methylphenyl)-2-thiocyanatopropan-1-one (5-B, 5.84 g, 22 mmol, 1 equiv.) in heptane (50 mL) was heated to 85° C. and then treated with Compound 4-B in heptane (30 mL) over 35 minutes. The resulting mixture was stirred overnight at 85° C. and then cooled to rt. The solvent was removed under reduced pressure and the crude material purified by flash chromatography over two runs (100 g, c-hexane/AcOEt 100:0 to 96:4 and c-hexane/MTBE 100:0 to 80:20) removing the solvent under reduced pressure to give Compound 6-B as a yellowish oil (5.50 g, 44% yield) after the second run. $^1$H NMR (400 MHz, CDCl$_3$) δ ppm −0.04-0.19 (m, 3H), 0.12 (s, 6H), 0.39-0.58 (m, 2H), 0.61-0.76 (m, 1H), 0.87-1.00 (m, 1H), 0.95 (s, 9H), 1.44 (s), 1.69-1.78 (m, 2H), 2.09 (s, 3H), 2.17 (s, 3H), 3.84 (s, 3H), 4.35-4.46 (m, 1H), 4.80 (s, 2H), 5.48-5.63 (m, 1H), 6.78-7.22 (m, 2H), 6.86 (s, 1H), 7.13 (s, 1H), 7.47 (s, 1H) residual solvent present. LCMS: [M]$^+$=575.

Step 5: Preparation of N-(1-(4-(((tert-butyldimethylsilyl)oxy)methyl)-3-fluorophenyl)-2-cyclopropylethyl)-4-(2-chloro-4-methoxy-5-methylphenyl)-5-methyl-N-(prop-2-yn-1-yl)thiazol-2-amine (Compound 7-B)

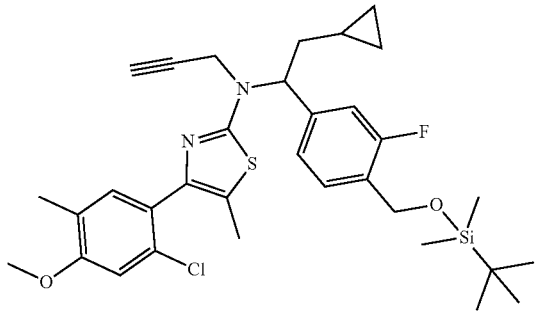

Compound 7-B

A mixture of N-(1-(4-(((tert-butyldimethylsilyl)oxy)methyl)-3-fluorophenyl)-2-cyclopropylethyl)-4-(2-chloro-4-methoxy-5-methylphenyl)-5-methylthiazol-2-amine (6-B, 5 g, 9 mmol) and TBAB (420 mg, 1 mmol) in methyl tert-butyl ether (10 mL) was stirred for 10 min. at rt. The mixture was then cooled to −10° C. and treated with aq. KOH (64%, 1.8 mL) at a rate to keep the temperature below 5° C. (1 h) to afford a mixture. The resulting mixture was treated with propargyl bromide in toluene (80%, 1.16 mL) at a rate to keep the temperature below 5° C. (30 min.) to afford a mixture. The resulting mixture was stirred at 5° C. for 20 h and then combined with methyl tert-butyl ether (10 mL) and water (10 mL). After vigorous shaking the layers were allowed to partition. The organic layer was washed with water (2×40 mL), dried over $Na_2SO_4$ and concentrated under reduced pressure to afford Compound 7-B as a residue used directly in the next step without further purification.

Step 6: Preparation of racemic {4-[1-{[4-(2-chloro-4-methoxy-5-methylphenyl)-5-methyl-1,3-thiazol-2-yl](prop-2-yn-1-yl)amino}-2-cyclopropylethyl]-2-fluorophenyl}methanol (Compound 1)

Compound 1

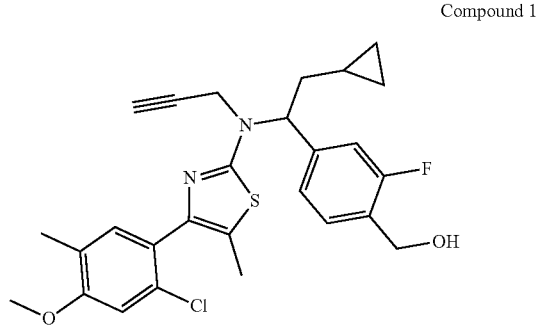 [SMILES: C#CCN(c1nc(-c2cc(C)c(OC)cc2Cl)c(C)s1)C(CC1CC1)c1ccc(CO)c(F)c1]

Compound 7-B was dissolved in anhydrous THF (50 mL) and 1 M TBAF in THF (10.4 mL) was added. The resulting mixture was stirred at rt for 3 h and then the solvent was removed under reduced pressure to afford a residue. The residue was combined with water (10 mL) and the resulting aqueous mixture was extracted with methyl tert-butyl ether (2×25 mL). The combined organic layers were dried over $Na_2SO_4$, filtered to removed solids and concentrated under reduced pressure to afford the crude product. The crude product was purified by column chromatography (50 g, c-hexane/AcOEt 100:0 to 80:20) to afford a first isolate as an orange foam (2 g, 46%). A second purification (50 g, c-hexane/AcOEt 100:0 to 80:20) gave the final product as an orange foam (1.5 g). $^1$H NMR (400 MHz, $CDCl_3$) δ ppm 0.15 (m, 2H), 0.38 (m, 2H), 0.72 (m, 1H), 1.4 (s), 1.85-1.95 (m, 1H), 2.11 (s, 3H), 2.11 (s, 3H), 2.10-2.15 (m, 1H), 2.31 (s, 1H), 3.13 (s, 1H), 3.26-3.36 (m, 2H), 3.32 (s, 2H), 3.84 (s, 3H) 4.00-4.18 (m, 2H), 4.44-4.57 (m, 2H), 5.16-5.31 (m, 2H), 7.01-7.09 (m, 1H), 7.12-7.18 (m, 1H) 7.19-7.31 (m, 2H) 7.36-7.49 (m, 1H) residual solvent present. LCMS: $[M]^+=499$.

Example 2

Preparation of (S)-{4-[1-{[4-(2-chloro-4-methoxy-5-methylphenyl)-5-methyl-1,3-thiazol-2-yl](prop-2-yn-1-yl)amino}-2-cyclopropylethyl]-2-fluorophenyl}methanol (Compound 2)

The preparation of (5)-{4-[1-{[4-(2-chloro-4-methoxy-5-methylphenyl)-5-methyl-1,3-thiazol-2-yl](prop-2-yn-1-yl)amino}-2-cyclopropylethyl]-2-fluorophenyl}methanol (Compound 2) is shown in Scheme 2.

Scheme 2

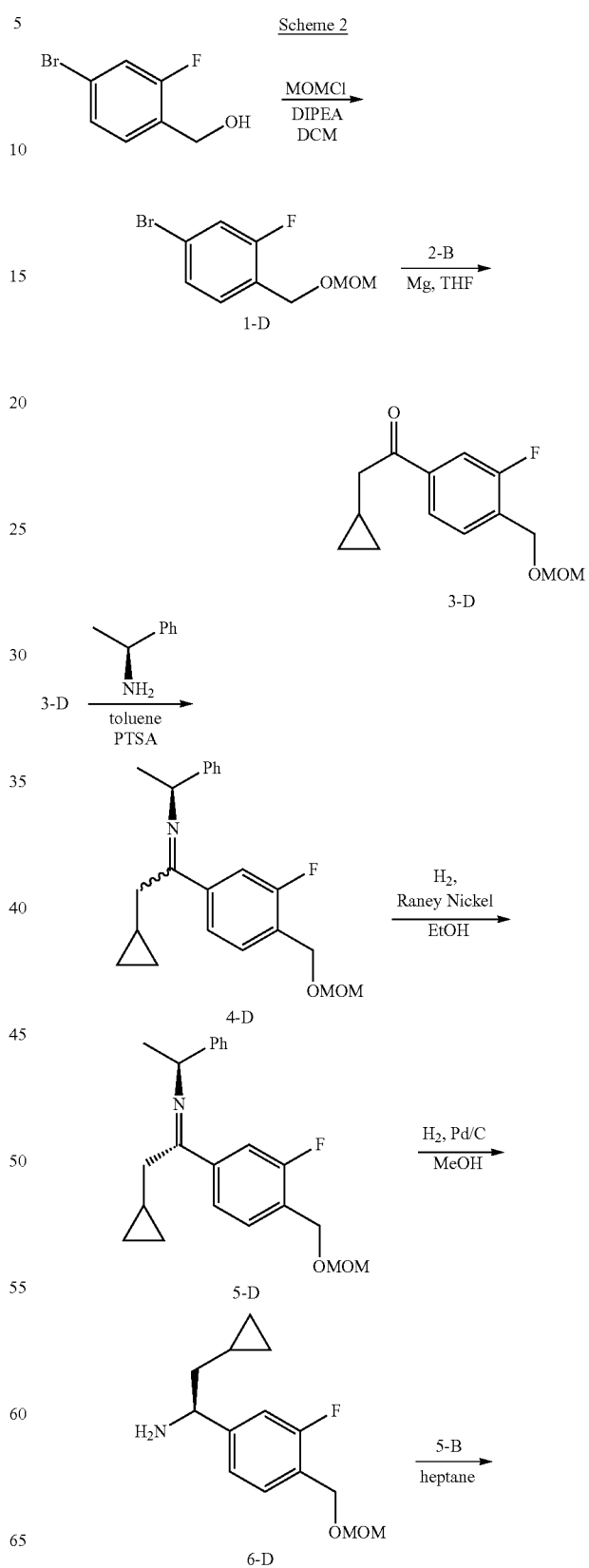

-continued

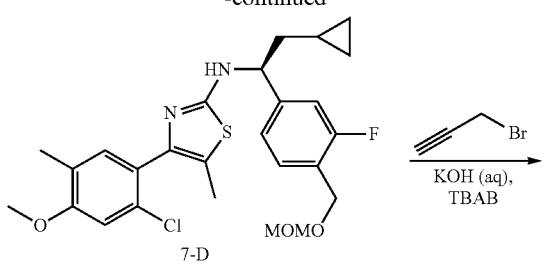
7-D

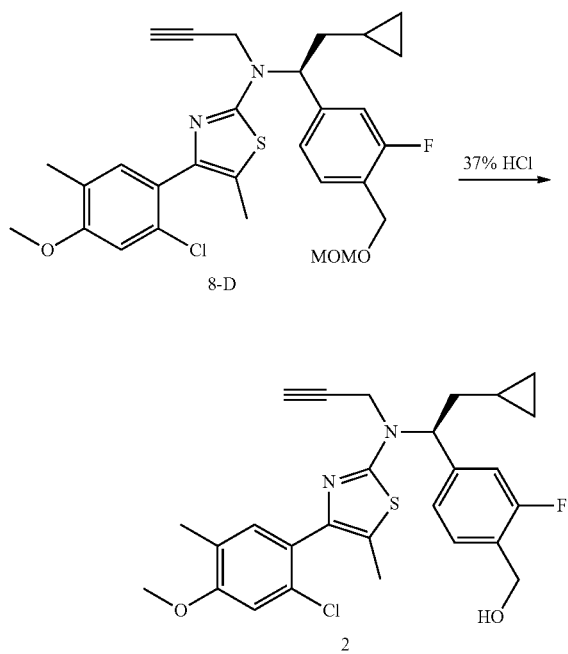
8-D

2

Step 1: Preparation of 4-bromo-2-fluoro-1-((methoxymethoxy)methyl)benzene (Compound 1-D)

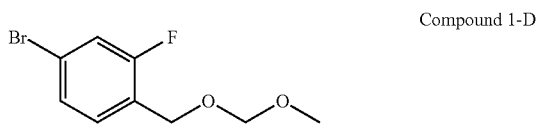
Compound 1-D

A mixture of (4-bromo-2-fluorophenyl)methanol (20 g, 98 mmol) and DIPEA (25.5 mL, 107 mmol) in methylene chloride (100 mL) was treated with methoxymethyl chloride (8.17 mL, 107 mmol) in methylene chloride (20 mL) over 20 min. at 4° C. The resulting mixture was stirred for 48 h. The mixture was washed with 5% aq. NaHCO₃ (50 mL), dried over NaSO₄, filtered and concentrated under reduced pressure. The crude material was purified by column chromatography (silica gel 100 g, c-hexane/AcOEt 100:0 to 95:5) to afford Compound 1-D as a colorless oil (23.5 g, 88% yield). $^1$H NMR (400 MHz, DMSO-$d_6$) δ ppm 1.40 (s), 3.28 (s, 3H), 4.54 (d, J=1.32 Hz, 2H), 4.65 (s, 2H), 7.37-7.48 (m, 2H), 7.50-7.60 (m, 1H) residual solvent present.

Step 2: Preparation of 2-cyclopropyl-1-(3-fluoro-4-((methoxymethoxy)methyl)phenyl)ethan-1-one (Compound 3-D)

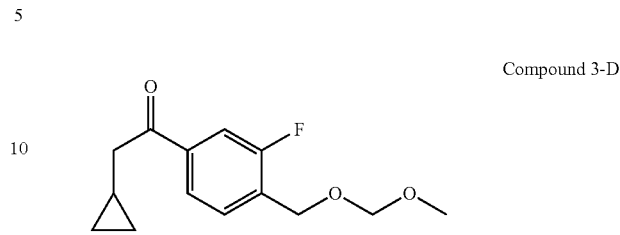
Compound 3-D

Magnesium turnings (2.34 g, 97 mmol, 1.2 equiv.) were suspended in anhydrous THF (40 mL). The mixture was treated with iodine (410 mg, 1.6 mmol, 0.02 equiv.). The resulting mixture was treated with a small portion of 4-bromo-2-fluoro-1-((methoxymethoxy)methyl)benzene (1-D, 2 g, 8 mmol, 0.1 wt. % of total) and the resulting suspension was gently heated with a heat gun until discoloration occurred. The remaining 4-bromo-2-fluoro-1-((methoxymethoxy)methyl)benzene (18 g, 72 mmol, 0.9 wt. % of total) was dissolved in THF (120 mL) and the resulting solution was added to the previously prepared suspension over 1.5 h. The resulting mixture was stirred at rt for 1 h. Subsequently, the Grignard suspension was cooled to 5° C. and then treated with 2-cyclopropyl-N-methoxy-N-methyl-acetamide (2-B, 17.25 g, 120 mmol) in THF (20 mL) over 20 min. The resulting mixture was stirred at rt overnight and then cooled to 5° C. and treated with satd. NH₄Cl (66 mL). The mixture was extracted with methyl tert-butyl ether (2×170 mL). The combined organic layers were washed with brine (170 mL), dried over Na₂SO₄, filtered and concentrated. The crude product was purified by column chromatography (silica gel, 100 g, c-hexane/AcOEt 100:0 to 80:20) to afford Compound 3-D as a colorless oil (8.0 g, 39% yield). $^1$H NMR (400 MHz, DMSO-$d_6$) δ ppm 0.15 (dd, J=4.83, 1.32 Hz, 2H), 0.50 (d, J=6.59 Hz, 2H), 0.92-1.14 (m, 1H), 2.95 (d, J=6.59 Hz, 2H), 3.30 (s, 3H), 3.31 (s), 4.64 (s, 2H), 4.68 (s, 2H), 7.56-7.66 (m, 1H), 7.68-7.76 (m, 1H), 7.77-7.85 (m, 1H).

Step 3: Preparation of (S)-2-cyclopropyl-1-(3-fluoro-4-((methoxymethoxy)methyl)phenyl)-N-(1-phenylethyl)ethan-1-imine (Compound 4-D)

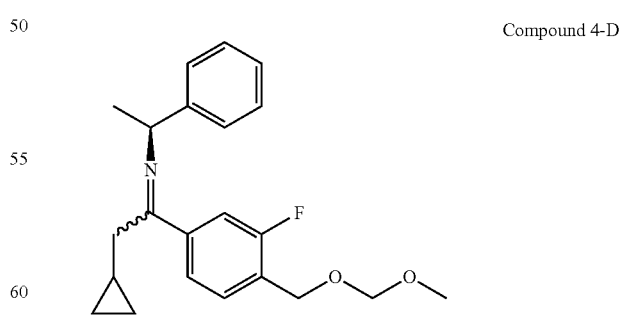
Compound 4-D

A mixture of 2-cyclopropyl-1-(3-fluoro-4-((methoxymethoxy)methyl)phenyl)ethan-1-one (3-D, 1.8 g, 7 mmol, 1 equiv.), (S)-(−)-phenylethylamine (2.59 g, 21 mmol, 3.0 equiv.) and PTSA·H₂O (70 mg, 0.37 mmol, 0.05 equiv.) in toluene (9 mL) was refluxed with a Dean-Stark condenser connected to the apparatus for 24 h. The mixture was cooled to rt and then washed with 10% Na₂CO₃ (3.6 mL) and 26% NaCl (3.6 mL). The organic solvent was removed under reduced pressure to afford crude Compound 4-D (2.54 g, assumed quant.) used directly in the next step.

Step 4: Preparation of (S)-2-cyclopropyl-1-(3-fluoro-4-((methoxymethoxy)methyl)phenyl)-N—((S)-1-phenylethyl)ethan-1-amine (Compound 5-D)

Compound 5-D

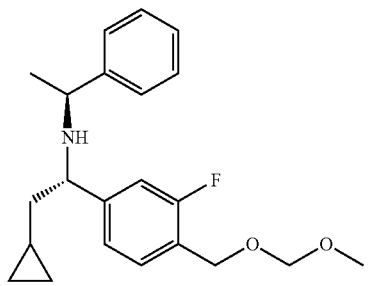

Raney Nickel (50% wet, 2.38 g, 20 mmol) was washed with absolute ethanol (4×6 mL) and transferred into a HEL autoclave to provide a catalyst suspension. Compound 4-D (2.4 g, 6.8 mmol) was added to the catalyst suspension, and ethanol was added to provide a final volume of 30 mL. The mixture underwent three vacuum/nitrogen cycles and two hydrogen purge cycles. The mixture was then stirred under hydrogen (pressure initial: 10 bar) at 25° C. for 6 h and 60° C. for 24 h. The mixture was filtered and the solids washed with ethanol (20 mL). The collected ethanol solution was concentrated, and the residue was purified by column chromatography (25 g c-hexane/AcOEt 100:0 to 80:20) to afford Compound 5-D as a pale oil (2 g, 83% yield). ¹H NMR (400 MHz, DMSO-d₆) δ ppm −0.36−−0.02 (m, 2H), 0.10-0.43 (m, 2H), 0.54-0.67 (m, 1H), 1.00-1.20 (m, 3H), 1.22-1.38 (m, 1H), 1.42-1.65 (m, 1H), 2.60-2.72 (m, 1H), 3.22-3.42 (m, 6H), 4.54 (s, 2H), 4.65 (s, 2H), 6.91-7.02 (m, 1H), 7.05-7.13 (m, 1H), 7.14-7.42 (m, 7H)) residual solvent peaks present. LCMS: [M+H]⁺=358.

Step 5: Preparation of (S)-2-cyclopropyl-1-(3-fluoro-4-((methoxymethoxy)methyl)phenyl)ethan-1-amine (Compound 6-D)

Compound 6-D

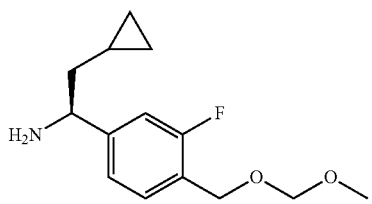

A steel autoclave was charged with (S)-2-cyclopropyl-1-(3-fluoro-4-((methoxymethoxy)methyl)phenyl)-N—((S)-1-phenylethyl)ethan-1-amine (5-D, 2 g, 6 mmol) and Pd/C (10% wet, 100 mg) in methanol (40 mL). The steel autoclave was purged with nitrogen for 2 min. The autoclave was then mounted onto an HEL Hydrogenation System and the mixture stirred under hydrogen (pressure initial: 8 bar) at 60° C. for 10 hours, then cooled to 20° C. and stirred overnight. The mixture was filtered over a Celite® pad and the filtrate concentrated to afford crude Compound 6-D (1.42 g, assumed quant.) used directly in the next step. ¹H NMR (400 MHz, DMSO-d₆) δ ppm −0.12−−0.06 (m, 2H), 0.23-0.43 (m, 2H), 0.52-0.69 (m, 1H), 1.31-1.52 (m, 2H), 1.89 (br s, 2H), 3.28 (s, 3H), 3.87 (t, J=6.81 Hz, 1H), 4.52 (s, 2H), 4.63 (s, 2H), 7.11-7.23 (m, 2H), 7.34 (t, J=7.69 Hz, 1H)) residual solvent peaks present. LCMS: [M+H]⁺=254.

Step 6: Preparation of (S)-4-(2-chloro-4-methoxy-5-methylphenyl)-N-(2-cyclopropyl-1-(3-fluoro-4-((methoxymethoxy)methyl)phenyl)ethyl)-5-methyl-thiazol-2-amine (Compound 7-D)

Compound 7-D

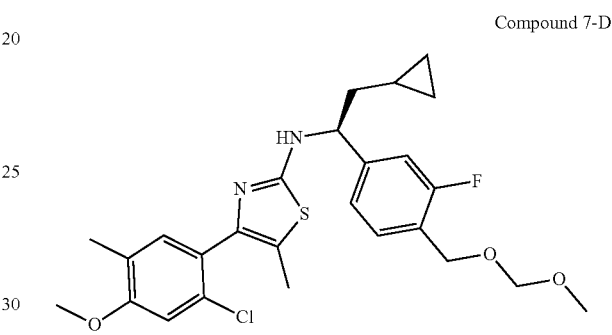

A suspension of 1-(2-chloro-4-methoxy-5-methylphenyl)-2-thiocyanatopropan-1-one (5-B, 1.51 g, 6 mmol, 1 equiv.) in heptane (15 mL) was heated to 90° C. and then treated with Compound 6-D (1.42 g, 6 mmol, 1 equiv.) in heptane (7 mL) over 15 minutes. The resulting mixture was stirred 3 h at 85° C. and then cooled to rt. The solvent was removed under reduced pressure to provide crude product. The crude product was purified by flash chromatography (50 g, c-hexane/AcOEt 100:0 to 90:10). The solvent was removed under reduced pressure to give Compound 7-D as a yellow foam (4.46 g, 94% yield). MS: [M]⁺=505.

Step 7: Preparation of (S)-4-(2-chloro-4-methoxy-5-methylphenyl)-N-(2-cyclopropyl-1-(3-fluoro-4-((methoxymethoxy)methyl)phenyl)ethyl)-5-methyl-N-(prop-2-yn-1-yl)thiazol-2-amine (Compound 8-D)

Compound 8-D

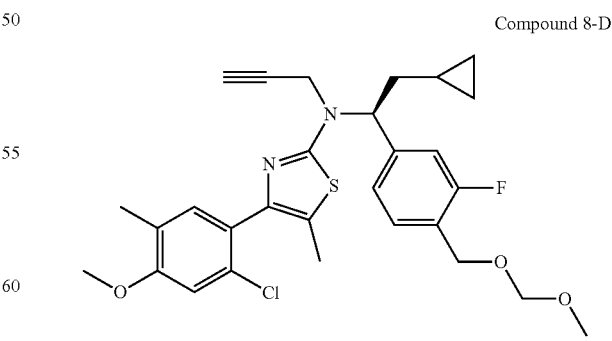

A mixture of Compound 7-D (2.5 g, 5 mmol) and TBAB (240 mg, 0.15 mmol) in methyl tert-butyl ether (6.25 mL) at −10° C. was treated with aq. KOH (64%, 4.5 mL) over 5 min. The resulting mixture was treated with propargyl bromide in toluene (80%, 0.66 mL) over 5 min. The resulting mixture was stirred at 5° C. for 5 h and then combined with methyl tert-butyl ether (10 mL) and water (10 mL). The layers were allowed to partition. The aqueous layer was washed with methyl tert-butyl ether (10 mL) and the combined organic layers were dried over Na$_2$SO$_4$, filtered and concentrated under reduced pressure to afford Compound 8-D as a residue used directly in the next step without further purification.

Step 8: Preparation of (S)-{4-[1-{[4-(2-chloro-4-methoxy-5-methylphenyl)-5-methyl-1,3-thiazol-2-yl]prop-2-yn-1-yl)amino}-2-cyclopropylethyl]-2-fluorophenyl}methanol (Compound 2)

Compound 2

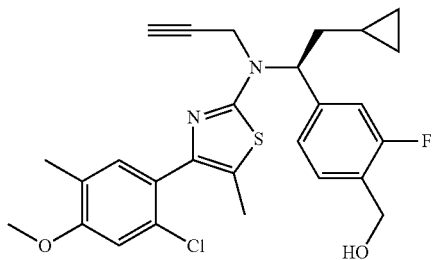

Compound 8-D was dissolved in acetone (30 mL) and 37% aqueous HCl (1.7 g) was added. The resulting mixture was stirred at 55° C. for 45 min. The mixture was cooled to rt and combined with satd. Na$_2$CO$_3$ (5 mL) followed by water (10 mL). The volatiles were removed under reduced pressure and the aqueous mixture combined with methyl tert-butyl ether (20 mL). The organic layer was collected and the aqueous phase was washed with methyl tert-butyl ether (2×10 mL). The combined organic layers were dried over Na$_2$SO$_4$, filtered to removed solids and concentrated under reduced pressure to afford a crude product. The crude product was purified by column chromatography (50 g, DCM/MTBE 100:0 to 95:5) to afford a first isolate (1.4 g, 91% HPLC purity) as a yellowish foam. The purification was repeated in the same conditions on the first isolate to afford a second isolate (1.1 g, 95% HPLC purity as a yellowish foam. A third purification (50 g, n-hexane/MTBE 100:0 to 60:40) gave Compound 2 (1 g, 98% HPLC purity, 80% ee) as off-white foam. MS: [M]$^+$=499. $^1$H NMR matches Compound 1 from Example 1.

Example 2A. Preparation of (S)-2-cyclopropyl-1-(3-fluoro-4-methylphenyl)-N-(1-phenylethyl)ethan-1-imine

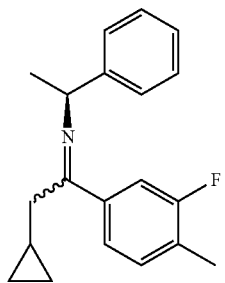 [SMILES: Cc1ccc(C(CC2CC2)=N[C@@H](C)c2ccccc2)cc1F]

The title compound may be prepared in a similar manner to the preparation of Compound 4-D using 2-cyclopropyl-1-(3-fluoro-4-methylphenyl)ethan-1-one in place of Compound 3-D in Step 3.

Example 2B. Preparation of (S)-2-cyclopropyl-1-(3-fluoro-4-methylphenyl)-N—((S)-1-phenylethyl)ethan-1-amine

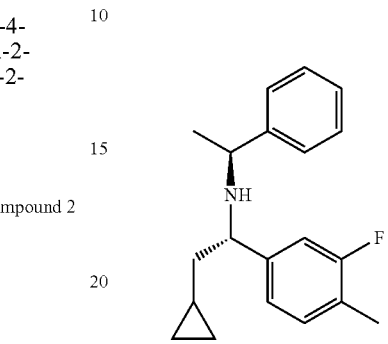

The title compound may be prepared in a similar manner to the preparation of Compound 5-D using (S)-2-cyclopropyl-1-(3-fluoro-4-methylphenyl)-N-(1-phenylethyl)ethan-1-imine in place of Compound 4-D in Step 4.

Example 3

Preparation of (S)-(4-(1-((4-(2-chloro-4-(methoxy-$^{13}$C-d$_3$)-5-methylphenyl)-5-methylthiazol-2-yl)(prop-2-yn-1-yl)amino)-2-cyclopropylethyl)-2-fluorophenyl)methanol (Compound 3)

The preparation of (S)-(4-(1-((4-(2-chloro-4-(methoxy-$^{13}$C-d$_3$)-5-methylphenyl)-5-methylthiazol-2-yl)(prop-2-yn-1-yl)amino)-2-cyclopropylethyl)-2-fluorophenyl)methanol (Compound 3) is shown in Scheme 3.

Scheme 3

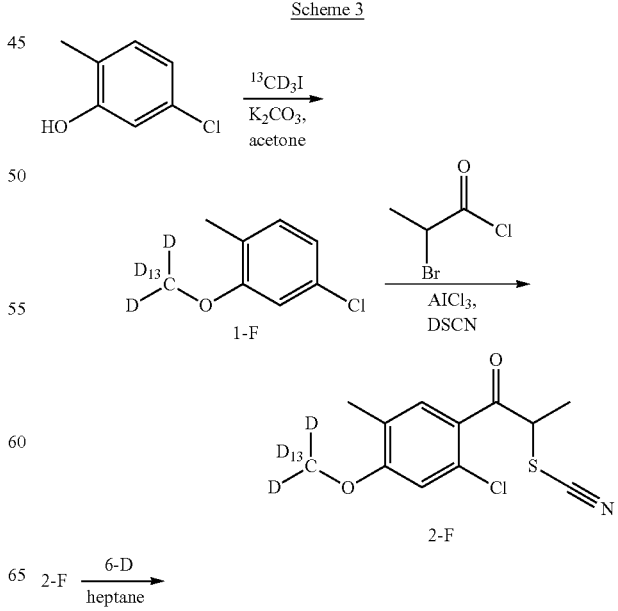

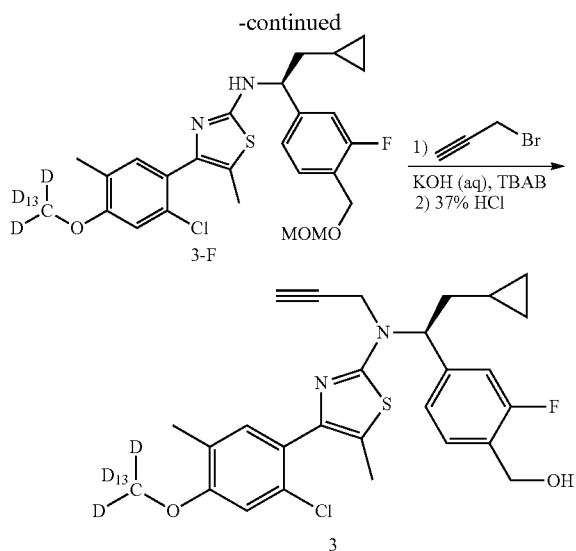

Step 1: Preparation of 4-chloro-2-(methoxy-$^{13}$C-d$_3$)-1-methylbenzene (Compound 1-F)

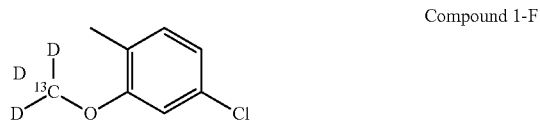

A mixture of 5-chloro-2-methylphenol (9 g, 63 mmol) and potassium carbonate (13.21 g, 69 mmol, 1.1 equiv.) was stirred for 15 min. at 20° C. in acetone (60 mL). A solution of iodomethane-$^{13}$C, d$_3$ (10.13 g, 69 mmol, 1.1 equiv.) in acetone (30 mL) was added over 30 minutes to the stirring mixture (slight exotherm observed, +1° C.). The mixture was stirred at rt for 24 h and then diluted with DMF (30 mL) and stirred at rt for an additional 15 h. The acetone was removed at atmospheric pressure until all acetone was distilled off (80° C.). The remainder was combined with water (250 mL) and the resultant was extracted with pentane (3×50 mL). The combined organic fractions were dried over Na$_2$SO$_4$, filtered to remove solid, and concentrated under reduced pressure to afford crude Compound 1-F as a yellow oil (10.6 g, assumed quant.) used directly in the next step. $^1$H NMR (400 MHz, DMSO-d$_6$) δ ppm 2.11 (s, 3H), 6.88 (dd, J=7.91, 2.20 Hz, 1H), 6.98 (d, J=2.20 Hz, 1H) 7.14 (dd, J=7.90, 0.88 Hz, 1H) residual solvent peaks present.

Step 2: Preparation of 1-(2-chloro-4-(methoxy-$^{13}$C-d$_3$)-5-methylphenyl)-2-thiocyanatopropan-1-one (Compound 2-F)

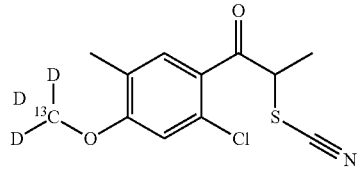

Aluminum trichloride (9.55 g, 72 mmol, 1.15 equiv.) was charged in a 500 mL-jacketed glass reactor, then DCM (40 mL) was added and the resulting mixture stirred at rt. Compound 1-F (10 g, 62 mmol, 1 equiv.) was added to the stirring mixture over 10 minutes at rt. The addition line was washed with DCM (10 mL) to ensure complete addition of Compound 1-F. The dark suspension was heated at 30° C. and stirred for 10 min. until almost complete dissolution. Subsequently, the mixture was cooled to 0° C. and treated with neat 2-bromopropanoyl chloride (12.27 g, 72 mmol, 1.15 equiv.) over 30 minutes; the addition line was washed with DCM (10 mL) to ensure complete addition of 2-bromopropanoyl chloride. The resulting mixture was stirred at 0° C. for 20 h. Subsequently, the mixture was cooled to −5° C. and treated with water (50 mL) over 15 min. The resulting mixture was maintained at 0° C. and stirred for 30 min. The mixture was then combined with c-hexane (300 mL) and the resulting suspension was stirred overnight. The layers were then partitioned, and the organic layer was washed with water (2×100 mL) and a 1:1 mixture of 13% aq. NaCl+5% aq. NaHCO$_3$ (100 mL, pH wash ca. 8). The organic layer was dried over Na$_2$SO$_4$, filtered and concentrated under reduced pressure to afford a residue. The residue was suspended in c-hexane (100 mL) and filtered. The solution was concentrated (90 mL) and diluted with DCM (10 mL). In a round bottom flask, KSCN (9.68 g, 100 mmol. 1.6 equiv.) and TBAB (0.30 g, 0.93 mmol. 0.015 equiv.) were dissolved in water (10 mL). The aqueous mixture was heated to 55° C. and then treated over 1 h with the previously prepared solution containing the bromo intermediate. The resulting mixture was stirred for 3.5 h and then water (10 mL) was added. The resulting mixture was stirred for 10 min. and the layers partitioned at 50° C. The organic layer was concentrated under reduced pressure and the remainder combined with methanol (60 mL). A white solid precipitated, and the mixture was stirred at rt for 30 min. and then at 0° C. for 1 h. The solid was collected by filtration and washed with cold methanol (10 mL) affording Compound 2-F as a white powder (10.3 g, 60% yield). $^1$H NMR (400 MHz, DMSO-d$_6$) δ ppm 1.60 (d, J=6.59 Hz, 3H), 2.16 (s, 3H), 5.28 (q, J=6.73 Hz, 1H), 7.15 (s, 1H) 7.74 (s, 1H) residual solvent peaks present.

Step 3: Preparation of (S)-4-(2-chloro-4-(methoxy-$^{13}$C-d$_3$)-5-methylphenyl)-N-(2-cyclopropyl-1-(3-fluoro-4-((methoxymethoxy)methyl)phenyl)ethyl)-5-methylthiazol-2-amine (Compound 3-F)

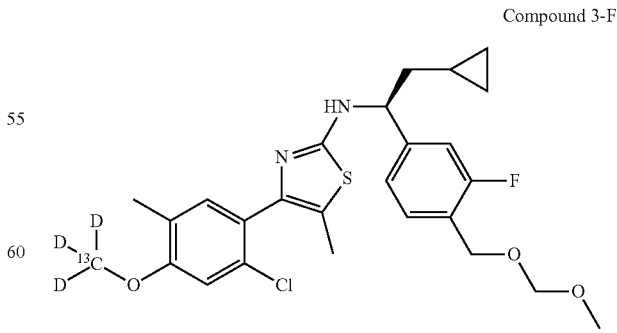

A suspension of 1-(2-chloro-4-(methoxy-$^{13}$C-d$_3$)-5-methylphenyl)-2-thiocyanatopropan-1-one (2-F, 2.16 g, 8 mmol, 1 equiv.) in heptane (20 mL) was heated to 90° C. and then treated with Compound 6-D (2 g, 8 mmol, 1 equiv.) in heptane (10 mL) over 20 min. The resulting mixture was stirred at 85° C. for 5 h and then cooled to rt. The solvent was removed under reduced pressure to provide crude product. The crude product was purified by flash chromatography (100 g, n-hexane/methyl tert-butyl ether 95:5 to 60:40). The solvent was removed under reduced pressure to give Compound 3-F as a yellow foam (3.5 g, 87% yield). $^1$H NMR (400 MHz, DMSO-d$_6$) δ ppm −0.03-0.16 (m, 2H), 0.27-0.45 (m, 2H), 0.63-0.76 (m, 1H), 0.82-0.89 (m), 1.20-1.30 (m), 1.42-1.54 (m, 1H), 1.72-1.83 (m, 1H), 2.00 (s, 3H), 2.10 (s, 3H), 3.28 (s, 3H), 3.32 (s), 4.52 (s, 2H), 4.63 (s, 2H), 4.55-4.68 (m, 1H), 7.00 (s, 1H), 7.05 (d, J=0.88 Hz, 1H), 7.16-7.25 (m, 1H), 7.33-7.42 (m, 1H), 7.93 (d, J=7.91 Hz, 1H) residual solvent peaks present. LCMS: [M]$^+$=575.

Step 4: Preparation of (S)-(4-(1-((4-(2-chloro-4-(methoxy-$^{13}$C-d$_3$)-5-methylphenyl)-5-methylthiazol-2-yl)(prop-2-yn-1-yl)amino)-2-cyclopropylethyl)-2-fluorophenyl)methanol (Compound 3)

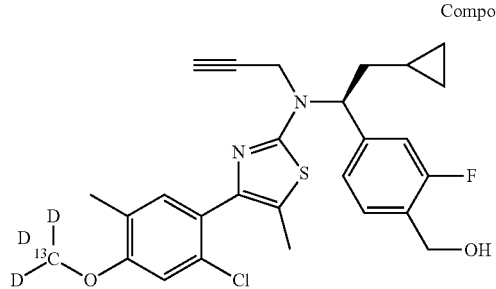

Compound 3

A mixture of Compound 3-F (3.2 g, 6.3 mmol) and TBAB (300 mg, 0.93 mmol, 0.15 equiv.) in methyl tert-butyl ether (15 mL) at −10° C. was treated with aq. KOH (64%, 5.76 mL) over 15 min. The resulting mixture was maintained at 0° C. and treated with propargyl bromide in toluene (80%, 0.84 mL) over 10 min. The resulting mixture was stirred at 5° C. overnight and then at rt for 1 h. The mixture was combined with methyl tert-butyl ether (10 mL) and water (10 mL). The layers were allowed to partition. The aqueous layer was washed with methyl tert-butyl ether (10 mL) and the combined organic layers were dried over Na$_2$SO$_4$, filtered and concentrated under reduced pressure to give a residue. The residue was dissolved in acetone (30 mL) and 37% aqueous HCl (2.3 g) was added. The resulting mixture was stirred at 55° C. for 1 h. The mixture was cooled to rt and combined with satd. Na$_2$CO$_3$ (10 mL) followed by water (10 mL). The volatiles were removed under reduced pressure and the aqueous mixture combined with methyl tert-butyl ether (20 mL). The organic layer was collected and the aqueous phase was extracted with methyl tert-butyl ether (2×20 mL). The combined organic layers were dried over Na$_2$SO$_4$, filtered to removed solids and concentrated under reduced pressure to afford a first isolate. The first isolate was purified by column chromatography (100 g, n-hexane/MTBE 100:0 to 60:40) to afford a second isolate. A second purification (100 g, DCM/MTBE 100:0 to 95:5) gave Compound 3 (1.6 g, 99.5% HPLC purity, 93% ee) as an off white foam. $^1$H NMR (600 MHz, DMSO-d$_6$) δ ppm 0.15 (m, 2H), 0.38 (m, 2H), 0.72 (m, 1H), 1.90 (dt, J=14.2, 7.1 Hz, 1H), 2.0-2.2 (overlapping, 1H), 2.11 (s, 3H), 2.14 (s, 3H), 2.31 (s, 1H), 3.12 (t, J=2.3 Hz, 1H), 4.09 (m, 2H), 4.52 (d, J=5.6 Hz, 2H), 5.23 (t, J=5.8 Hz, 1H), 5.27 (t, J=7.6 Hz, 1H), 7.05 (s, 1H), 7.17 (s, 1H) 7.22 (d, J=11.5 Hz, 1H) 7.26 (d, J=7.9 Hz, 1H), 7.43 (t, J=7.9 Hz, 1H). MS: 98.1% $^{13}$CD$_3$ purity.

Example 3A

Preparation of Enantiomerically Enriched (S)-2-cyclopropyl-1-(3-fluoro-4-((methoxymethoxy)methyl)phenyl)ethan-1-amine (Compound 6-D) used in Example 3, Step 3

Step 1A: Preparation of (S)-2-cyclopropyl-1-(3-fluoro-4-((methoxymethoxy)methyl)phenyl)-N—((S)-1-phenylethyl)ethan-1-amine (Compound 5-D)

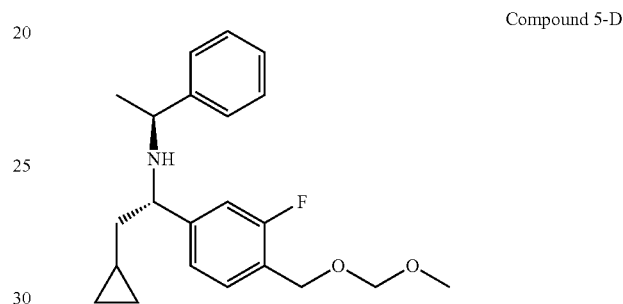

Compound 5-D

Following the procedure described in Example 2, Step 3, Compound 4-D (5.61 g, 15.8 mmol) was hydrogenated over Raney Nickel (3 equiv.) for 30 h. After isolation, the crude product was purified by three consecutive column chromatography elutions (100 g, hexane/AcOEt 100:0 to 90:10; 2×100 g, c-hexane/IPA 100:0 to 95:5) to give Compound 5-D (3.1 g, 55% yield) with a diastereomeric ratio of ca. 97:3 ($^1$H-NMR, DMSO-d$_6$, 94% de). Selected mixed chromatography fractions were joined together to give an additional sample of Compound 5-D (1.43 g, 25% yield) with a diastereomeric ratio of ca. 85:15 d.r. ($^1$H-NMR, DMSO-d$_6$, 70% de).

Step 2A: Preparation of (S)-2-cyclopropyl-1-(3-fluoro-4-((methoxymethoxy)methyl)phenyl)ethan-1-amine (Compound 6-D)

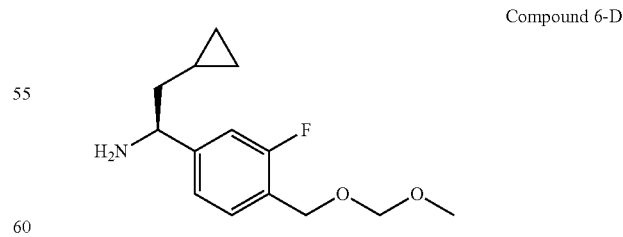

Compound 6-D

Following the procedure described in Example 2, Step 4, Compound 5-D (3.1 g, 8.7 mmol, 94% de) was hydrogenated over Pd/C (pressure initial: 10 bar) at 60° C. for 10 hours. The reaction was processed as described in Example 2, Step 4, to afford crude Compound 6-D (2.2 g, assumed quant.) used directly in Example 3, Step 3.

Example 4. Preparation of (S)-(4-(1-((4-(2-chloro-4-(methoxy-d₃)-5-methylphenyl)-5-methylthiazol-2-yl)(prop-2-yn-1-yl)amino)-2-cyclopropylethyl)-2-fluorophenyl)methanol (Compound 4) is shown in Scheme 4

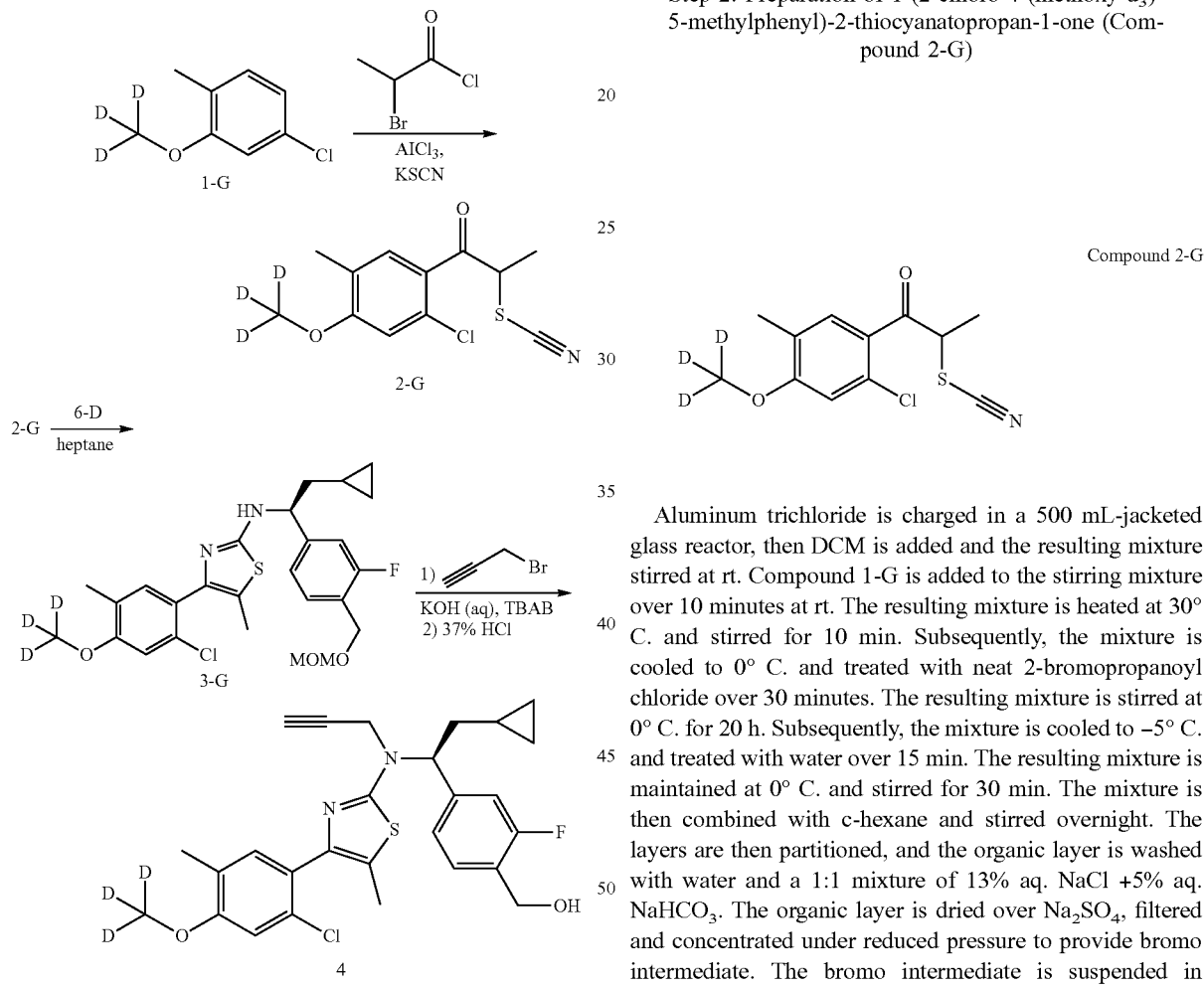

Step 1: Preparation of 4-chloro-2-(methoxy-d₃)-1-methylbenzene (Compound 1-G)

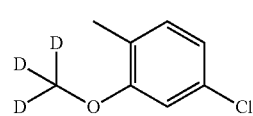

Compound 1-G

A mixture of 5-chloro-2-methylphenol and potassium is stirred for 15 min. at 20° C. in acetone. A solution of iodomethane-d₃ in acetone is added over 30 minutes to the stirring mixture. The mixture is stirred at rt for 24 h and then diluted with DMF and stirred at rt for an additional 15 h. The acetone is removed at atmospheric pressure until all acetone is distilled off (80° C.). The remainder is combined with water and the resultant is extracted with pentane. The combined organic fractions are dried over Na₂SO₄, filtered to remove solid, and concentrated under reduced pressure to afford Compound 1-G.

Step 2: Preparation of 1-(2-chloro-4-(methoxy-d₃)-5-methylphenyl)-2-thiocyanatopropan-1-one (Compound 2-G)

Compound 2-G

Aluminum trichloride is charged in a 500 mL-jacketed glass reactor, then DCM is added and the resulting mixture stirred at rt. Compound 1-G is added to the stirring mixture over 10 minutes at rt. The resulting mixture is heated at 30° C. and stirred for 10 min. Subsequently, the mixture is cooled to 0° C. and treated with neat 2-bromopropanoyl chloride over 30 minutes. The resulting mixture is stirred at 0° C. for 20 h. Subsequently, the mixture is cooled to −5° C. and treated with water over 15 min. The resulting mixture is maintained at 0° C. and stirred for 30 min. The mixture is then combined with c-hexane and stirred overnight. The layers are then partitioned, and the organic layer is washed with water and a 1:1 mixture of 13% aq. NaCl +5% aq. NaHCO₃. The organic layer is dried over Na₂SO₄, filtered and concentrated under reduced pressure to provide bromo intermediate. The bromo intermediate is suspended in c-hexane and filtered. The solution is concentrated and diluted with DCM. In a round bottom flask, KSCN and TBAB are dissolved in water. The aqueous mixture is heated to 55° C. and then treated over 1 h with a solution containing the bromo intermediate. The resulting mixture is stirred for 3.5 h and then water is added. The resulting mixture is stirred for 10 min. and the layers partitioned at 50° C. The organic layer is concentrated under reduced pressure and the remainder combined with methanol. The mixture is stirred at rt for 30 min. and then at 0° C. for 1 h. Solid is collected by filtration and washed with cold methanol to afford Compound 2-G.

Step 3: Preparation of (S)-4-(2-chloro-4-(methoxy-d₃)-5-methylphenyl)-N-(2-cyclopropyl-1-(3-fluoro-4-((methoxymethoxy)methyl)phenyl)ethyl)-5-methylthiazol-2-amine (Compound 3-G)

Compound 3-G

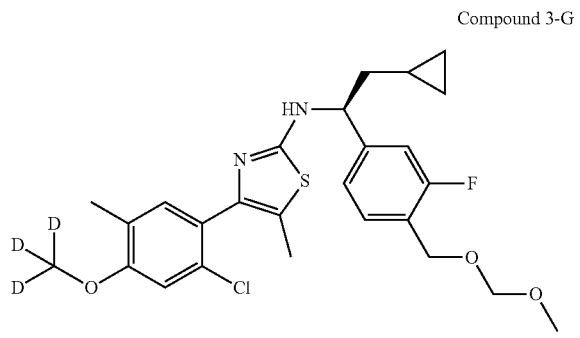 [SMILES: [2H][13C]([2H])([2H])Oc1cc(Cl)c(-c2nc(N[C@@H](CC3CC3)c3ccc(COCOC)c(F)c3)sc2C)cc1C]

A mixture of Compound 2-G in heptane is heated to 90° C. and then treated with Compound 6-D in heptane over 20 min. The resulting mixture is stirred at 85° C. for 5 h and then cooled to rt. The solvent is removed under reduced pressure to provide crude product. The crude product is purified by flash chromatography (100 g, n-hexane/methyl tert-butyl ether 95:5 to 60:40). The solvent is removed under reduced pressure to give Compound 3-G.

Step 4: Preparation of (S)-(4-(1-((4-(2-chloro-4-(methoxy-d₃)-5-methylphenyl)-5-methylthiazol-2-yl)(prop-2-yn-1-yl)amino)-2-cyclopropylethyl)-2-fluorophenyl)methanol (Compound 4)

Compound 4

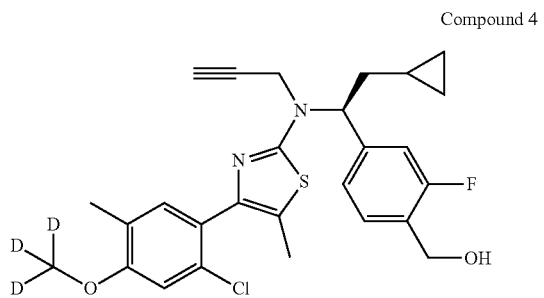 [SMILES: [2H]C([2H])([2H])Oc1cc(Cl)c(-c2nc(N(CC#C)[C@@H](CC3CC3)c3ccc(CO)c(F)c3)sc2C)cc1C]

A mixture of Compound 3-G and TBAB in methyl tert-butyl ether (15 mL) at −10° C. is treated with aq. KOH (64%) over 15 min. The resulting mixture is maintained at 0° C. and treated with propargyl bromide in toluene (80%) over 10 min. The resulting mixture is stirred at 5° C. overnight and then at rt for 1 h. The mixture is combined with methyl tert-butyl ether and water. The layers are allowed to partition and the aqueous layer is extracted with methyl tert-butyl ether. The combined organic layers are dried over Na₂SO₄, filtered and concentrated under reduced pressure to give an intermediate product. The intermediate product is dissolved in acetone and 37% aqueous HCl is added. The resulting mixture is stirred at 55° C. for 1 h. The mixture is cooled to rt and combined with satd. Na₂CO₃ followed by water. The volatiles are removed under reduced pressure and the aqueous mixture combined with methyl tert-butyl ether. The organic layer is collected and the aqueous phase is extracted with methyl tert-butyl ether. The combined organic layers are dried over Na₂SO₄, filtered to removed solids and concentrated under reduced pressure to afford a first isolate. The first isolate is purified by column chromatography (n-hexane/MTBE 100:0 to 60:40) to afford a second isolate. The second isolate is purified by column chromatography (DCM/MTBE 100:0 to 95:5) to afford Compound 4.

Example 5

Preparation of (S)-(4-(1-((4-(2-chloro-4-(methoxy-d₃)-5-methylphenyl)-5-methylthiazol-2-yl)(prop-2-yn-1-yl)amino)-2-cyclopropylethyl-2,2-d₂)-2-fluorophenyl)methanol (Compound 5) is shown in Scheme 5

Scheme 5

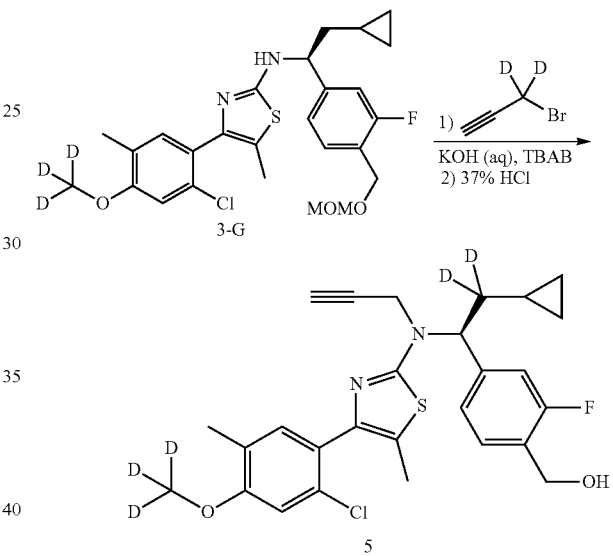

A mixture of Compound 3-G and TBAB in methyl tert-butyl ether (15 mL) at −10° C. is treated with aq. KOH (64%) over 15 min. The resulting mixture is maintained at 0° C. and treated with 3-bromoprop-1-yne-3,3-d₂ over 10 min. The resulting mixture is stirred at 5° C. overnight and then at rt for 1 h. The mixture is combined with methyl tert-butyl ether and water. The layers are allowed to partition and the aqueous layer is extracted with methyl tert-butyl ether. The combined organic layers are dried over Na₂SO₄, filtered and concentrated under reduced pressure to give intermediate product. The intermediate product is dissolved in acetone and 37% aqueous HCl is added. The resulting mixture is stirred at 55° C. for 1 h. The mixture is cooled to rt and combined with satd. Na₂CO₃ followed by water. The volatiles are removed under reduced pressure and the aqueous mixture combined with methyl tert-butyl ether. The organic layer is collected and the aqueous phase is extracted with methyl tert-butyl ether. The combined organic layers are dried over Na₂SO₄, filtered to removed solids and concentrated under reduced pressure to afford a first isolate. The first isolate is purified by column chromatography (n-hexane/MTBE 100:0 to 60:40) to afford a second isolate. The second isolate is purified by column chromatography (DCM/MTBE 100:0 to 95:5) to afford Compound 5.

LC-MS analyses were conducted using the following methods:

Method: A
 Platform: Agilent 1260 UPLC with a Thermo MSQ mass detector and Agilent DAD (220 and 254 nm);
 HPLC column: Waters BEH C18 XP, 2.5 50×3.0 mm;
 HPLC Gradient: 1.5 mL/min, 40% acetonitrile (with 0.025% TFA) in water (with 0.025% TFA) for 6 seconds, then increase to 100% acetonitrile over 1.5 minutes. Hold at 100% acetonitrile for 18 seconds. Return to 40% acetonitrile over 6 seconds and hold at 40% for 30 seconds.

Method: B
 Platform: Agilent 1260 UPLC with a Thermo MSQ mass detector and Agilent DAD (220 and 254 nm);
 HPLC column: Waters BEH C18 XP, 2.5 50×3.0 mm;
 HPLC Gradient: 1.5 mL/min, 10% acetonitrile (with 0.025% TFA) in water (with 0.025% TFA) for 6 seconds, then increase to 90% acetonitrile over 6.5 minutes. Increase to 99% acetonitrile over 6 seconds, then hold at 99% acetonitrile for 12 seconds. Return to 10% acetonitrile over 6 seconds and hold at 10% for 30 seconds.

Example 6

Preparation of {4-[(1S)-1-{[4-(2-chloro-4-methoxy-5-methylphenyl)-5-methyl-1,3-thiazol-2-yl](prop-2-yn-1-yl)amino}-2-cyclopropylethyl]-2-fluorophenyl}methyl (2S)-2-amino-3-methylbutanoate (Compound 6) is shown in Scheme 6

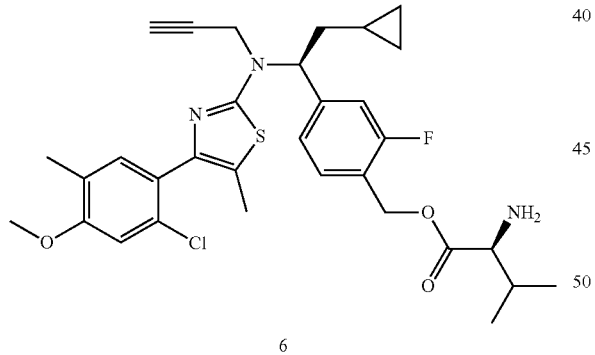

A mixture of Compound 2 (50 mg) and Boc-Valine (26 mg) in MeCN (2 mL) was treated with DIC (19 mg, diisopropylcarbodiimide) followed by DMAP (1 mg). The resulting mixture was stirred at r.t. overnight. The solvent was removed and the mixture was purified by chromatography on silica gel eluting with EtOAc/Hex to afford the Boc-protected intermediate as an oil. This material was dissolved in DCM (2 mL) and the resulting mixture treated with 4 M HCl in dioxane (2 mL). The resulting mixture was stirred for 2 h at r.t. The solvent was removed under vacuum and the resulting residue triturated with MTBE. A solid precipitate formed and was filtered off and dried by suction to afford Compound 6 (50 mg) as the HCl salt as a white powder. LCMS of Boc-protected intermediate (Method: A): m/z (M+H)=698.3; tR=1.99 mins. LCMS of Compound 6 (Method: B): m/z (M+H)=598.2; tR=4.48 mins.

Example 7

Preparation of 5-({4-[(1S)-1-{[4-(2-chloro-4-methoxy-5-methylphenyl)-5-methyl-1,3-thiazol-2-yl](prop-2-yn-1-yl)amino}-2-cyclopropylethyl]-2-fluorophenyl}methoxy)-5-oxopentanoic acid (Compound 7) is shown in Scheme 7

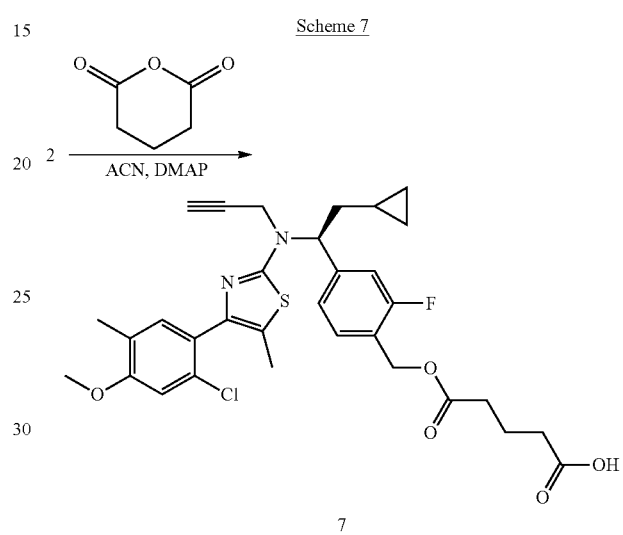

A mixture of Compound 2 (50 mg) and glutaric anhydride (23 mg) in MeCN (2 mL) was treated with DMAP (1 mg). The resulting mixture was stirred at r.t. overnight. The solvent was removed and the mixture was purified by chromatography on silica gel eluting with EtOAc/Hex to afford a first isolate as an oil. The first isolate was dissolved in THF/Water (1:1, 5 mL) and the resulting mixture was treated with sodium bicarbonate until pH 7 was reached (approximately 1 equiv.). The solvent was removed under vacuum and the resulting residue was placed under vacuum overnight affording Compound 7 (31 mg) as the sodium salt as a white powder. LCMS of Compound 7 (Method: B): m/z (M+H)=613.2; tR=5.05 mins.

Example 8

Preparation of ({4-[(1S)-1-{[4-(2-chloro-4-methoxy-5-methylphenyl)-5-methyl-1,3-thiazol-2-yl](prop-2-yn-1-yl)amino}-2-cyclopropylethyl]-2-fluorophenyl}methoxy)phosphonic acid (Compound 8) is shown in Scheme 8

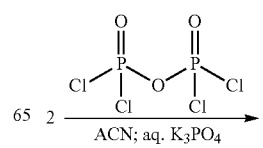

-continued

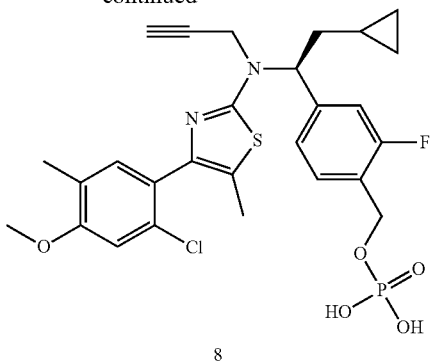

8

A mixture of Compound 2 (50 mg) in MeCN (2 mL) was slowly treated with diphosphoryl chloride (50 mg, 2 equiv.) at rt and stirred for 30 min. Subsequently, the mixture was added to an excess aqueous $K_3PO_4$ solution (2 mL) with stirring. After 30 mins stirring, the solvent was removed under vacuum and 20% aqueous phosphoric acid (1 mL) was added to afford a strongly acidic mixture. This mixture was extracted with DCM and the DCM extract was dried over $MgSO_4$ and concentrated under vacuum to afford a first isolate. The first isolate was purified by HPLC (water/MeCN with 0.025% TFA) to afford a second isolate as an oil. The second isolate was dissolved in water/MeCN (1 mL) and treated with 1 M aqueous NaOH under stirring until the mixture reached pH 7 (approximately 2 equiv.). Subsequently, the solvent was removed under vacuum to afford Compound 8 as bis-sodium salt as an off-white powder (15 mg). LCMS (Method: B): m/z=579.0; tR=4.13 mins.

Example 9

CRF$_1$ Receptor Antagonist Activity

As reported in Fleck et al. (*J. Pharmacology and Experimental Therapeutics*, 341(2):518-531, 2012) (hereinafter "Fleck et al." and incorporated by reference in it's entirely) the activity of a CRF$_1$ receptor antagonists may be expressed as the kinetically derived affinity ($K_i$) calculated from the association ($k_1$) and dissociation ($k_{-1}$) rate constants by the following equation:

$$K_i = k_{-1}/k_1$$

Compound 1 was evaluated according to these procedures, and the kinetic $K_i$ was determined to be 1.14.

Example 10

Dissociation Half-Life ($t_{1/2}$) of Representative Compound

The dissociation half-life ($t_{1/2}$) of Compound 1 was also evaluated by the technique described in Fleck et al. As described therein, the dissociation rate constant for labeled and unlabeled ligands is denoted as $k_{-1}$, while the half-life of drug dissociation from the receptor ($t_{1/2}$), which is equal to the median residence time, is calculated from the dissociation rate constant ($k_{-1}$) by the following equation:

$$t_{1/2} = 0.693/k_{-1}.$$

Compound 1 was evaluated according to these procedures, and the dissociation half-life ($t_{1/2}$) was determined to be 63 minutes.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

INCORPORATION BY REFERENCE

Various references such as patents, patent applications, and publications are cited herein, the disclosures of which are hereby incorporated by reference herein in their entireties.

We claim the following:
1. A pharmaceutical composition comprising a compound of formula (IIa):

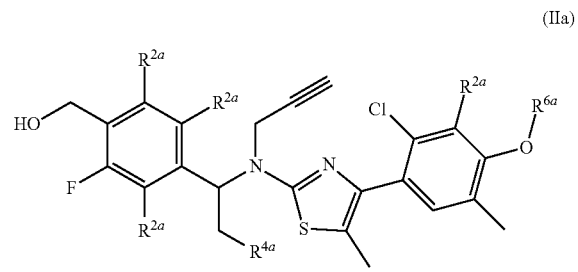

(IIa)

or a pharmaceutically acceptable salt thereof and at least one pharmaceutically acceptable excipient, wherein:
each $R^{2a}$ is independently hydrogen or deuterium;
$R^{4a}$ is

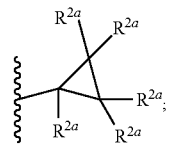

$R^{6a}$ is $C(R^A)_3$; and
each $R^A$ is independently hydrogen or deuterium.
2. The pharmaceutical composition of claim 1, wherein the compound of formula (IIa) is a compound of formula:

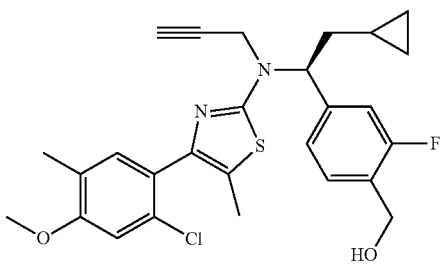 [SMILES: C#CCN(c1nc(-c2cc(C)c(OC)cc2Cl)c(C)s1)[C@@H](CC1CC1)c1ccc(CO)c(F)c1]

or a pharmaceutically acceptable salt thereof.
3. A method of treating congenital adrenal hyperplasia in a subject in need thereof comprising administering to the subject a therapeutically effective amount of a compound of formula (IIa):

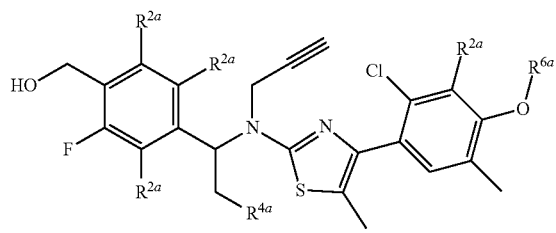
(IIa)
or a pharmaceutically acceptable salt thereof, wherein:
each $R^{2a}$ is independently hydrogen or deuterium;
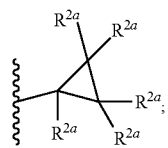
$R^{4a}$ is
$R^{6a}$ is $C(R^A)_3$; and
each $R^A$ is independently hydrogen or deuterium.
4. The method of claim 3, wherein the compound of formula (IIa) is a compound of formula:
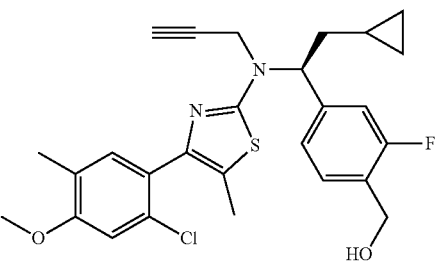 [SMILES: C#CCN(c1nc(-c2cc(C)c(OC)cc2Cl)c(C)s1)[C@@H](CC1CC1)c1ccc(CO)c(F)c1]
or a pharmaceutically acceptable salt thereof.
* * * * *